(12) United States Patent
Leung et al.

(10) Patent No.: US 11,344,050 B2
(45) Date of Patent: May 31, 2022

(54) APPARATUSES AND SYSTEMS FOR PREPARING A MEAT PRODUCT

(71) Applicant: Upside Foods, Inc., Berkeley, CA (US)

(72) Inventors: Matthew Leung, Richmond, CA (US); Michelle Warner, Redwood City, CA (US); Ryan Edward Vanderpol, Oakland, CA (US); Thomas Pei-Ja Hsiu, Palo Alto, CA (US); Kathleen Carswell, San Francisco, CA (US)

(73) Assignee: Upside Foods, Inc., Berkeley, CA (US)

( * ) Notice: Subject to any disclaimer, the term of this patent is extended or adjusted under 35 U.S.C. 154(b) by 0 days.

(21) Appl. No.: 17/469,687

(22) Filed: Sep. 8, 2021

(65) Prior Publication Data

US 2022/0000154 A1     Jan. 6, 2022

Related U.S. Application Data

(63) Continuation of application No. 17/100,705, filed on Nov. 20, 2020, now Pat. No. 11,147,300.
(Continued)

(51) Int. Cl.
| | |
|---|---|
| *C12N 5/00* | (2006.01) |
| *A23L 13/00* | (2016.01) |
| *C12M 3/00* | (2006.01) |
| *C12M 1/12* | (2006.01) |
| *C12M 1/00* | (2006.01) |

(Continued)

(52) U.S. Cl.
CPC ............ *A23L 13/00* (2016.08); *C12M 21/08* (2013.01); *C12M 23/06* (2013.01); *C12M 29/06* (2013.01); *C12M 33/00* (2013.01); *C12N 5/0602* (2013.01); *C12N 5/0697* (2013.01); *A23V 2002/00* (2013.01)

(58) Field of Classification Search
CPC .................................................... C12N 5/0068
See application file for complete search history.

(56) References Cited

U.S. PATENT DOCUMENTS

| | | |
|---|---|---|
| 7,875,448 B2 | 1/2011 | Furey |
| 8,294,632 B2 | 10/2012 | Skarp |

(Continued)

FOREIGN PATENT DOCUMENTS

| | | |
|---|---|---|
| EP | 2 736 357 B1 | 6/2014 |
| KR | 10-2018-0026792 A | 3/2018 |

(Continued)

OTHER PUBLICATIONS

Office Action as received in European application 20745342.4 dated Dec. 9, 2021.
(Continued)

*Primary Examiner* — Rosanne Kosson
(74) *Attorney, Agent, or Firm* — Keller Preece PLLC

(57) ABSTRACT

The apparatuses described herein relate to preparation of a meat product. Apparatuses, systems comprising the apparatuses, and methods of making and use the systems and apparatuses are described herein. These are useful for controlling one or more of growth on and separation of a meat product from an enclosed substrate. The apparatuses and systems are configured to receive fluid and grow the meat product and/or separate the meat product from the substrate in a scalable manner.

19 Claims, 33 Drawing Sheets
(7 of 33 Drawing Sheet(s) Filed in Color)

Related U.S. Application Data

(60) Provisional application No. 62/938,087, filed on Nov. 20, 2019.

(51) Int. Cl.
   *C12M 1/26* (2006.01)
   *C12N 5/071* (2010.01)

(56) References Cited

U.S. PATENT DOCUMENTS

| | | | |
|---|---|---|---|
| 9,023,642 | B2 | 5/2015 | Kleis et al. |
| 9,249,383 | B2 | 2/2016 | Yu et al. |
| 9,657,266 | B2 | 5/2017 | Kasuto et al. |
| 9,994,812 | B2 | 6/2018 | Kim et al. |
| 11,147,300 | B2 | 10/2021 | Leung et al. |
| 2005/0084958 | A1 | 4/2005 | Vein |
| 2008/0009063 | A1* | 1/2008 | Okano ............... C12M 25/06 435/402 |
| 2008/0208351 | A1 | 8/2008 | Besenbacher et al. |
| 2010/0216242 | A1 | 8/2010 | Shimizu et al. |
| 2011/0212493 | A1 | 9/2011 | Hirschel et al. |
| 2013/0029008 | A1 | 1/2013 | Forgacs et al. |
| 2014/0093618 | A1 | 4/2014 | Forgacs et al. |
| 2015/0125952 | A1 | 5/2015 | Kim et al. |
| 2016/0227830 | A1 | 8/2016 | Genovese et al. |
| 2016/0251625 | A1 | 9/2016 | Genovese et al. |
| 2017/0253849 | A1 | 9/2017 | Miller |
| 2019/0024079 | A1 | 1/2019 | Genovese et al. |
| 2020/0165569 | A1 | 5/2020 | Genovese et al. |
| 2021/0106032 | A1 | 4/2021 | Leung et al. |
| 2021/0145031 | A1 | 5/2021 | Leung et al. |
| 2021/0171912 | A1 | 6/2021 | Genovese et al. |

FOREIGN PATENT DOCUMENTS

| | | |
|---|---|---|
| WO | WO 99/31222 | 6/1999 |
| WO | WO 2006/041429 A2 | 4/2006 |
| WO | WO 2014/036187 A1 | 3/2014 |
| WO | WO 2018/011805 A2 | 1/2018 |
| WO | WO 2019/014652 A1 | 1/2019 |
| WO | WO 2019/122239 A1 | 6/2019 |
| WO | WO 2020/243324 A1 | 12/2020 |

OTHER PUBLICATIONS

International Search Report and Written Opinion dated Nov. 9, 2020, in International Application No. PCT/US2020/034949, 15 pages.
International Search Report and Written Opinion dated Mar. 12, 2021, in International Application No. PCT/US2020/061676, 13 pages.
Acevedo et al., "Micropatterning Technology to Design an Edible Film for In Vitro Meat Production", Food and Bioprocess Technology, vol. 11, No. 7, Mar. 25, 2018, pp. 1267-1273.
Bhat et al., Prospectus of cultured meat-advancing meat alternatives, Journal of Food Science and Technology, vol. 48, No. 2, Dec. 30, 2010, pp. 125-140.
Brunette, "Fibroblasts on micromachined substrata orient hierarchically to grooves of different dimensions," Exp Cell Res. 1986; 164(1):11-26.
Brunette, "Spreading and orientation of epithelial cells on grooved substrata," Exp Cell Res. 1986; 167(1):203-217.
Clark et al., "Topographical control of cell behaviour: II. multiple grooved substrata," Development 108, 635-644 (1990).
Datar et al., "Possibilities for an in vitro meat production system," Innovative Food Science and Emerging Technologies, vol. 11, No. 1, Jan. 1, 2010, pp. 13-22.
Gaydhane et al., "Cultured meat: state of the art and future," Biomanufacturing Reviews, vol. 3, No. 1, Mar. 19, 2018.
Karuri et al., "Biological length scale topography enhances cell-substratum adhesion of human corneal epithelial cells," J Cell Sci. 2004; 117: 3153-3164.
Lam et al., "Microfeature guided skeletal muscle tissue engineering for highly organized 3-dimensional free-standing constructs", Biomaterials, vol. 30, No. 6, Feb. 1, 2009, pp. 1150-1155.
Ostrovidov et al., "Skeletal Muscle Tissue Engineering: Methods to Form Skeletal Myotubes and Their Applications" Tissue Engineering: Part B, vol. 20, No. 5, Oct. 1, 2014 (Oct. 1, 2014), pp. 403-436.
Riboldi et al., "Electrospun degradable polyesterurethane membranes: potential scaffolds for skeletal muscle tissue engineering," Biomaterials, vol. 26, No. 22, Aug. 1, 2005, pp. 4606-4615.
Hosseini et al. "Engineered contractile skeletal muscle tissue on a microgrooved methacrylated gelatin substrate." Tissue Eng Part A. Dec. 2012;18(23-24):2453-65. (Year: 2012).
Bajaj et al. "Patterning the differentiation of C2C12 skeletal nnyoblasts."Integrative Biology, vol. 3, Issue 9, Sep. 2011, pp. 897-909 (Year: 2011).
Cha et al. "Study of myoblast differentiation using multi-dimensional scaffolds consisting of nano and micropatterns."Biomater Res .Jan. 11, 2017;21:1. (Year: 2017).
Charest et al. "Myoblast alignment and differentiation on cell culture substrates with microscale topography and model chemistries." Biomaterials.Apr. 2007;28(13):2202-10. (Year: 2007).
Zeng et al. "A minimally invasive method for retrieving single adherent cells of different types from cultures"Sci Rep .Jun. 24, 2014;4:5424. (Year: 2014).
U.S. Appl. No. 17/131,514, dated Mar. 3, 2021, Office Action.
U.S. Appl. No. 17/131,514, dated Jun. 16, 2021, Office Action.
U.S. Appl. No. 17/100,705, dated Apr. 21, 2021, Office Action.
U.S. Appl. No. 17/100,705, dated Aug, 10, 2021, Notice of Allowance.
Willem Vesser et al. "Quantifying Cell Adhesion through Impingement of a Controlled Microjet."Biophys J. Jan. 6, 2015; 108(1): 23-31. (Year: 2015).
"What is Fluid Mechanics." Mechanical Engineering. Penn state College of Egineering. Retrieved on Dec. 1, 2021. Retrieved from https://www.rne.psu.eduicinnbala/Learning/Fluid/Introductory/what is fluid rnechanics.htrn (Year: 2021).
U.S. Appl. No. 17/131,514, dated Dec. 6, 2021, Office Action.
U.S. Appl. No. 17/131,514, dated Mar. 29, 2022, Notice of Allowance.
U.S. Appl. No. 17/469,680, dated Apr. 15, 2022, Office Action.

* cited by examiner

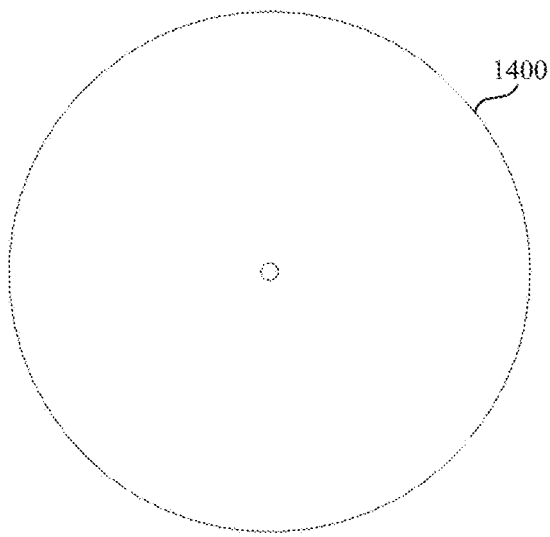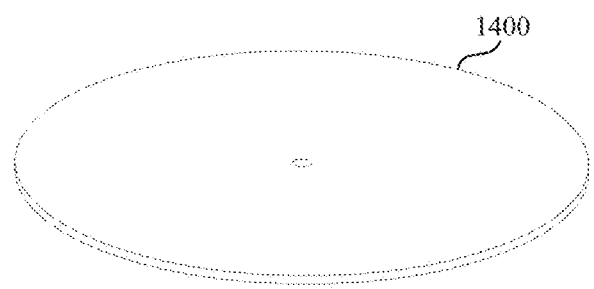
FIG. 14A             FIG. 14B
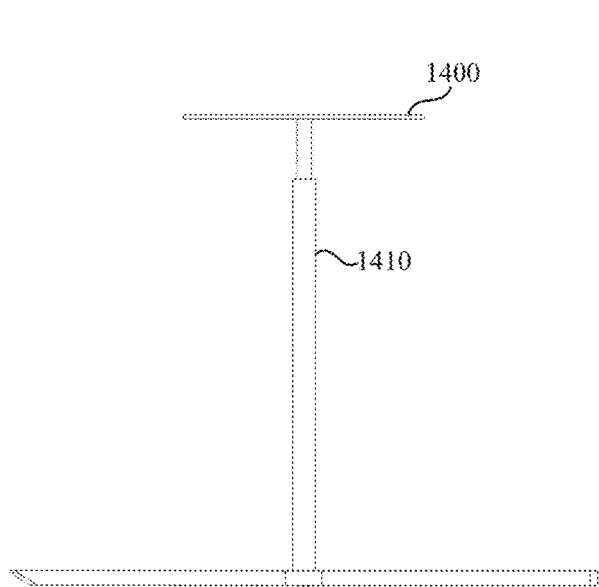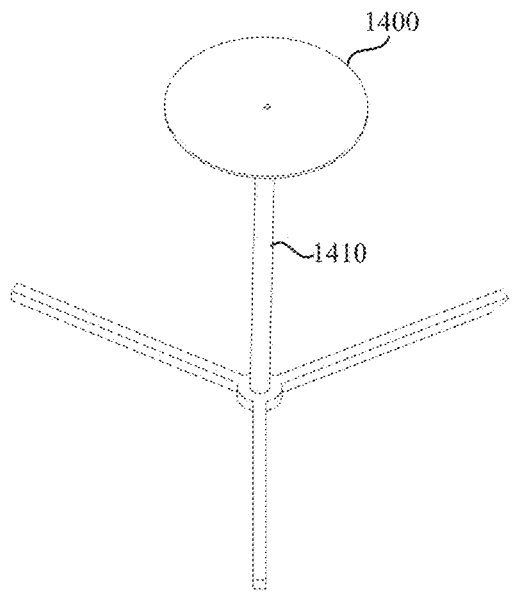
FIG. 14C             FIG. 14D

APPARATUSES AND SYSTEMS FOR PREPARING A MEAT PRODUCT

CROSS-REFERENCE TO RELATED APPLICATIONS

This application is a continuation of U.S. patent application Ser. No. 17/100,705, filed Nov. 20, 2020, which claims the benefit of U.S. Provisional Application No. 62/938,087, filed Nov. 20, 2019, the contents of each of which are hereby incorporated by reference in their entirety.

BACKGROUND

Apparatuses built to support proliferation and differentiation of cells in culture are typically designed to recover a product of the cells secreted in media (e.g. antibodies) while the cells themselves are merely unrecovered byproducts. Furthermore, these conventional apparatuses are not designed to support the growth of continuous cell sheets (e.g., a cell-based meat product) on a practical scale suitable for consumption. Therefore, systems, apparatuses, and methods for preparing a meat product are desirable.

SUMMARY

Described herein are apparatuses and systems for preparing a meat product, and methods of using thereof. Generally, the apparatuses, systems, and methods described herein grow a meat product on one or more enclosed substrates. For example, an apparatus for preparing a meat product may comprise an enclosure comprising a cavity, and a substrate arranged within the cavity and comprising a plurality of nested surfaces curved around a longitudinal axis and a surface configured to support growth of the meat product. The substrate may be configured to receive a fluid substantially parallel to the longitudinal axis.

In some embodiments, the enclosure may be configured to be placed on a ground surface, wherein the longitudinal axis is at an acute angle relative to the ground surface. In some embodiments, the acute angle may be at least about 85 degrees. In some embodiments, a separator may be configured to separate the meat product from the substrate in a continuous sheet of cells held together by one or more of cell-to-cell interactions and extracellular matrix generated by the cells. In some embodiments, the separator may comprise one or more fluid nozzles configured to direct the fluid towards the substrate at a predetermined angle. In some embodiments, the separator may be configured to rotate about a predetermined axis when the fluid is directed at the meat product. In some embodiments, the fluid may comprise a linear velocity between about 0.003 m/sec and about 3.0 m/sec.

Also described here are apparatuses for preparing a meat product that may comprise an enclosure defining a cavity, a substrate arranged within the cavity and configured to support growth of the meat product, and a fluid diffuser coupled to the enclosure and configured to distribute fluid to the substrate in a predetermined flow pattern. A ratio of a diameter of the fluid diffuser to a diameter of the substrate may be between about 3:4 and about 1:1

In some embodiments, the fluid diffuser may be configured to enable a substantially uniform or laminar flow across a surface of the substrate. The fluid diffuser may comprise one or more openings. The cavity may comprise a headspace, and the fluid diffuser may be disposed within the headspace of the enclosure.

In some embodiments, the fluid diffuser may comprise a tapered surface configured to distribute fluid to the substrate in a predetermined flow pattern. In some embodiments, the tapered surface comprises one or more of a concave shape, conical shape, frustum shape, stepped shape, and flared shape. In some embodiments, the tapered surface may be angled up to about 80 degrees relative to the substrate.

In some embodiments, the fluid diffuser may comprise a bicone comprising a first surface and a second surface opposing the first surface. The first surface may be configured to receive the fluid and the second surface may be configured to receive the fluid from the first surface and distribute the fluid to the substrate.

Also described herein are methods of preparing a comestible meat product that may comprise growing the comestible meat product on a substrate of an apparatus, and separating the comestible meat product from the substrate in a continuous sheet of cells held together by one or more of cell-to-cell interactions and extracellular matrix generated by the cells.

In some embodiments, separating the comestible meat product comprises directing a fluid at a predetermined angle relative to the spiral substrate. In some embodiments, the predetermined angle may be between about 0 degrees and about 10 degrees relative to the substrate. In some embodiments, the spiral substrate may be disposed into a cavity of the apparatus. In some embodiments, the fluid may be removed from the apparatus prior to separating the comestible meat product from the substrate. In some embodiments, the substrate may comprise a spiral shape.

In some embodiments, an apparatus for preparing a meat product may comprise an enclosure defining a cavity and a fluid diffuser coupled to the enclosure. The fluid diffuser may comprise a plurality of openings comprising a total area of at least about 700 $\mu m^2$. A plurality of substrates are configured to grow the meat product. The substrates may be disposed within the cavity and coupled to the fluid diffuser.

In some embodiments, the fluid diffuser may comprise at least a first portion and a second portion. The first portion may be angled relative to the second portion between about 90 degrees and about 170 degrees. In some embodiments, each of the first portion and the second portion are angled relative to the plurality of substrates up to about 80 degrees.

In some embodiments, the plurality of openings of the fluid diffuser are substantially equally spaced apart. In some embodiments, each of the plurality of openings comprises a diameter of at least about 30 $\mu m$. In some embodiments, the fluid diffuser comprises an interface between the first portion and the second portion, wherein the interface comprises one or more of the plurality of openings. In some embodiments, the fluid diffuser is coupled to a proximal end of the plurality of substrates.

In some embodiments, the fluid diffuser comprises one or more of stainless steel, a ceramic, and a polymer. In some embodiments, the first portion and the second portion are substantially flat. In some embodiments, the enclosure and the fluid diffuser are substantially circular and each comprise an inner diameter and an outer diameter. The outer diameter of the fluid diffuser is substantially equal to the inner diameter of the enclosure.

In some embodiments, the fluid diffuser is configured to output a substantially uniform and laminar flow to the plurality of substrates. In some embodiments, the fluid diffuser is configured to releasably engage to the enclosure. In some embodiments, the fluid diffuser is at least partially disposed in the cavity.

In some embodiments, the apparatus comprises a plurality of fluid channels. In some embodiments, at least one of the fluid channels is associated with at least one of the plurality of substrates. In some embodiments, one or more of the fluid channels is planar. In some embodiments, each of the fluid channels is between adjacent substrates. In some embodiments, fluid is configured to flow in one direction through the plurality of fluid channels. In some embodiments, the plurality of fluid channels are substantially parallel to each other. In some embodiments, the fluid channel comprises a space between adjacent substrates between about 0.3 mm and about 5.0 cm.

In some embodiments, the plurality of substrates are parallel to each other. In some embodiments, one or more of the substrates are planar. In some embodiments, one or more of the substrates are non-planar. In some embodiments, the plurality of substrates comprise one or more of stainless steel, a ceramic, and a polymer. In some embodiments, the apparatus comprises up to about 10,000,000 substrates. In some embodiments, the plurality of substrates comprises one or more of a plate, rectangle, rod, bead, and disk shape. In some embodiments, each substrate comprises a width between about 10 cm and about 400 cm. In some embodiments, each substrate comprises an area between about 430 $cm^2$ and about 8,000 $cm^2$. In some embodiments, the plurality of substrates are configured to releasably engage to the enclosure. In some embodiments, one or more of the substrates are configured to grow the meat product on opposite sides of the substrate.

In some embodiments, at least one collector coupled to the enclosure. In some embodiments, the collector comprises a plurality of openings comprising a total area of at least about 25 $\mu m^2$. In some embodiments, the collector is coupled to a distal end of the plurality of substrates. In some embodiments, the collector comprises one or more of stainless steel, a ceramic, and a polymer. In some embodiments, the collector is configured to receive the meat product separated from the plurality of substrates. In some embodiments, the collector is configured to releasably engage to the enclosure.

In some embodiments, the enclosure comprises one or more inlets configured to receive fluid. In some embodiments, the enclosure comprises one or more outlets configured to output the fluid. In some embodiments, the one or more inlets are disposed on a first side of the enclosure, and the one or more outlets are disposed on a second side of the enclosure, opposite the first side of the enclosure. In some embodiments, the enclosure comprises a volume between about 25 L and about 20,000 L.

In some embodiments, the one or more outlets comprise a diameter configured to output a meat product separated from the plurality of substrates. In some embodiments, the enclosure comprises a substantially cylindrical shape. In some embodiments, a rotator is coupled to the enclosure and configured to rotate the enclosure about a lateral axis of the enclosure.

Also described here are systems for preparing a meat product comprising an apparatus comprising a plurality of substrates, a fluid pump coupled to the apparatus, a fluid source coupled to the fluid pump, and a controller coupled to the fluid pump. The controller is configured to generate a first fluid pump signal to grow the meat product on the substrates and generate a second fluid pump signal to separate the meat product from the substrates.

In some embodiments, the first fluid pump signal is configured to provide a substantially uniform and laminar flow of the fluid to the plurality of substrates using the fluid pump. In some embodiments, the first fluid pump signal comprises a first flow rate and the second fluid pump signal comprises a second flow rate higher than the first flow rate.

In some embodiments, one or more sensors configured to measure one or more parameters of the fluid. In some embodiments, the first fluid pump signal comprises a flow rate of up to about 3.0 meters per second. In some embodiments, the second fluid pump signal corresponds to a linear velocity within the apparatus of up to about 10 meters per second. In some embodiments, the fluid source comprises growth media. In some embodiments, the growth media comprises cells. In some embodiments, the system is configured to grow the meat on the substrate for at least about 1 day.

Also described here are methods for preparing a meat product comprising applying a plurality of non-human cells to at least one substrate of an apparatus, culturing the cells on the substrate using a first fluid comprising growth media thereby generating the meat product, and separating the meat product from the substrate using the first fluid or a second fluid flowing through the apparatus.

In some embodiments, culturing the cells comprises providing a substantially uniform and laminar first fluid to the substrate. In some embodiments, about 5,000 cells/$cm^2$ and about 100,000 cells/$cm^2$ are applied to the cells.

In some embodiments, the first fluid is recirculated in the apparatus at a rate between about 0.0001 meters per second and about 3.0 meters per second. In some embodiments, the first fluid flows through the apparatus from a first elevation to a second elevation lower than the first elevation. In some embodiments, the cells are cultured on the substrate for at least 1 day. In some embodiments, the first fluid comprises a planar flow over the substrate. In some embodiments, the meat product is held together by an extracellular matrix secreted by the cells and/or cell-to-cell interactions.

In some embodiments, the cells comprise one or more of myoblasts, mesangioblasts, myofibroblasts, mesenchymal stem cells, hepatocytes, fibroblasts, pericytes, adipocytes, epithelial, chondrocytes, osteoblasts, osteoclasts, pluripotent cells, somatic stem cells, and endothelial cells.

In some embodiments, the cells comprise one or more cells from livestock, poultry, game, and aquatic animal species. In some embodiments, culturing the cells comprises aligning the substrate substantially perpendicular to a ground surface. In some embodiments, applying the one or more cells to the substrate comprises rotating the apparatus such that the substrate is parallel to ground.

In some embodiments, the separated meat product is received in a collector. In some embodiments, the collector is disposed in a cavity of the apparatus. In some embodiments, the collector is coupled externally to the apparatus. In some embodiments, the meat product of the substrate comprises a volume between about 0.0001 $m^3$ and about 0.1 $m^3$. In some embodiments, the substrate is sterilized after separating the meat product. In some embodiments, another meat product is cultured and separated after sterilizing the substrate. In some embodiments, sterilizing the substrate comprises steaming the apparatus. In some embodiments, at least one of the substrates is detached from the apparatus.

Also described are methods of preparing a meat product comprising any of the apparatuses and systems described herein. In some embodiments, the fluid diffuser is detached from the apparatus. In some embodiments, the collector is detached from the apparatus. Also described here are meat products generated by the methods described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The present application can be understood by reference to the following description taking in conjunction with the accompanying figures.

FIG. 14A is an illustrative plan view of an exemplary embodiment of a fluid diffuser. FIG. 14B is an illustrative perspective view of the fluid diffuser shown in FIG. 14A. FIG. 14C is an illustrative side view of an exemplary embodiment of a fluid diffuser and holder. FIG. 14D is an illustrative perspective view of the fluid diffuser and holder shown in FIG. 14C.

DETAILED DESCRIPTION

Figure 1:
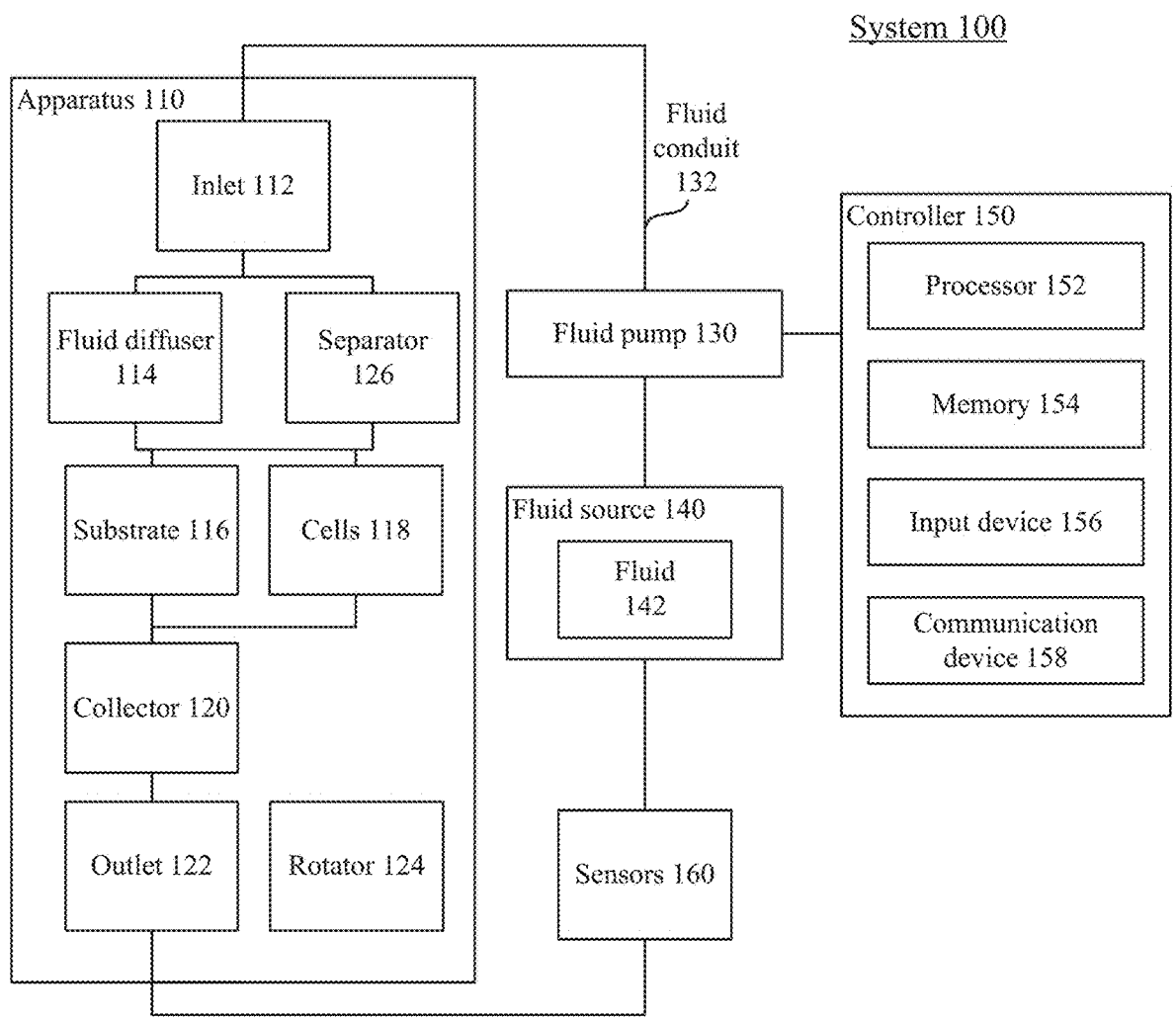
FIG. 1 is an illustrative block diagram of an exemplary embodiment of a system for preparing a meat product.

The systems, apparatuses, and methods provided herein are useful to control the characteristics of growth, adhesion, release, and/or retention of cultured cells (e.g., cell sheets) to prepare a meat product. Generally, the systems, apparatuses, and methods described herein grow and adhere a population of cells to one or more substrates for a predetermined amount of time to generate a meat product. In some embodiments, the number and/or size of the substrates may be scaled to generate a predetermined volume of meat product (e.g., as part of a commercial-scale process to form a cell-based meat product, interchangeably referred to herein as comestible tissue).

Large-scale cell growth for edible meat production faces particular challenges, addressed by the systems, apparatus, and methods provided herein. Conventional apparatuses such as cell culture vessels and bioreactors are not suited for meat production since they are utilized for culturing cells in suspension culture, and are not capable of sustained growth of cell sheets. Other conventional apparatuses that are designed for growth of adherent cells are limited in size, and incorporate a tortuous fluid flow path to accommodate their size constraints. By contrast, the apparatuses described herein may cost-effectively scale to grow cells of sufficient physical dimensions (e.g., cell sheets) to generate a meat product. For example, in some embodiments, growth of one or more cell sheets in an apparatus of the disclosure may require sufficient time where the cells remain adhered to a substrate for a predetermined time period (e.g., growth period) and/or cell state (e.g., observed metabolic signature or cell differentiation change). One or more fluids (e.g., growth media, culture media, liquid) may flow through the apparatus in a predetermined flow pattern to perfuse the cells and promote cell growth/differentiation/adherence on one or more substrates. However, providing a predetermined fluid flow over large surface areas is challenging. As described herein, a fluid diffuser may be configured to receive and distribute the fluid to one or more substrates with a substantially uniform and laminar flow to promote consistent cell growth across the surface area of the one or more substrates.

Once the cells are grown into a cell sheet (e.g. production of a meat product) on one or more of the substrates, then it may be desirable to recover the grown meat product from the apparatus in a substantially intact and/or contemporaneous manner for further processing, optimally in predetermined dimensions. In some embodiments, recovery of one or more cell sheets is aided by a fluidic release mechanism (e.g., fluid-based shear stress) thereby allowing controlled and scalable production and collection of an edible meat product. In some embodiments, a fluid other than the one used for the growth of the cells may be used to separate a produced cell sheet from the substrate as an end product for collection. For example, a separator may be configured to receive and distribute another fluid to one or more substrates in a predetermined flow pattern sufficient to separate the grown meat product from the substrates. Thus, the apparatuses described herein provide significant improvements to one or more of growth, adhesion, retention, and separation of cell sheets in an apparatus over conventional systems and techniques. Moreover, the apparatus may be configured to be disassembled, sterilized, and reused to reduce waste and cost, and improve production efficiency.

As used herein, a cell sheet may be either a monolayer of cells or a multi-cell layer. The cell sheet may include an extracellular matrix (ECM). In some embodiments, a cell sheet may be held together by an ECM generated by the cells and/or the cells may form a sheet via cell-to-cell binding proteins to form a substantially continuous unit. For example, the secretion of sufficient ECM proteins can allow constituent cells to stick together as a substantially continuous cell sheet via a combination of cell-to-cell and cell-to-ECM interactions. In some embodiments, a cell sheet is held together by an endogenously produced scaffold such as an ECM. In other embodiments, the ECM is exogenously provided.

In some embodiments, a method of preparing a meat product may comprise applying a plurality of non-human cells to a substrate of an apparatus, culturing the cells on the substrate using a first fluid comprising growth media, thereby generating the meat product (e.g. cell sheet), and separating the meat product from the substrate using a second fluid flowing through the apparatus (e.g., through one or more separators).

I. APPARATUSES

Provided herein are apparatuses for controlling one or more of the growth of a cell sheet (a meat product) on, and separation of a meat product from, an enclosed substrate.

An apparatus of the disclosure for preparing a meat product includes: (a) an enclosure (e.g., chamber, housing, container) defining a cavity; (b) a fluid diffuser coupled to the enclosure comprising a plurality of openings; and (c) a plurality of substrates configured to grow the meat product, the substrates disposed within the cavity, and coupled to the fluid diffuser. In some embodiments, the apparatus may further include a separator configured to separate the meat product from one or more of the substrates, and a collector coupled to the enclosure to collect the meat product.

The components of the apparatus (e.g., enclosure, fluid diffuser, substrates, separator, collector) may be composed of a material including, but not limited to, one or more of polychlorotrifluoroethylene, polyetherimide, polysulfone, polystyrene, polycarbonate, polypropylene, silicone, polyetheretherketone, polymethylmethacrylate, nylon, acrylic, polyvinylchloride, vinyl, phenolic resin, petroleum-derived polymers, glass, polyethylene, terephthalate, stainless steel, titanium, aluminum, cobalt-chromium, chrome, silicates, glass, alloys, ceramics, carbohydrate polymer, mineraloid matter, and combinations or composites thereof.

These components are described in turn herein, in further detail. Non-limiting exemplary embodiments of the apparatus are illustrated and described in more detail with respect to FIGS. 1, 3A-3D, 7A-7D, 8A-8C, 10A-10C, and 17A-17C. FIGS. 2A-9B and 17A-17C depict a first exemplary embodiment of an apparatus for preparing a meat product. FIGS. 2A-2E, 10A-12B, and 17A-17C describe a second exemplary embodiment of an apparatus for preparing a meat product. FIGS. 2A-2E and 13-17C depict a third exemplary embodiment of an apparatus for preparing a meat product.

A. Enclosure

Generally, the enclosure of an apparatus may be configured to provide a sealed chamber to allow for the sterile growth of a meat product. The enclosure may comprise one or more inlets configured to receive fluid and one or more outlets configured to output the fluid. In some embodiments, one or more inlets may be disposed on a first side of the enclosure, and the one or more outlets may be disposed on a second side of the enclosure, opposite the first side of the enclosure.

In some embodiments, the apparatus may comprise dimensions comprising an internal cavity volume of at least about 1 L. For example, the apparatus may comprise an internal volume between about 25 L and about 200 L, between about 100 L and about 500 L, between about 500 L and about 1,000 L, and between about 1,000 L and about 40,000 L, including all values and sub-ranges in-between. In some embodiments, the cavity may comprise a headspace. A fluid diffuser may be disposed within the headspace of the enclosure.

Non-limiting exemplary embodiments of the enclosure are illustrated and described in more detail with respect to FIGS. 2A-2E, 3A, 7A-7D, 8A-8C, 9A, 13A-13C, 13E-13F, and 18A-18E.

B. Fluid Diffuser

The apparatuses of the disclosure comprise one or more fluid diffusers (referred to interchangeably herein as a flow conditioner or a flow regulator) configured to receive fluid and provide a predetermined fluid flow to one or more of the substrates. For example, the fluid diffuser may be configured to receive and distribute the fluid to a plurality of substrates in a predetermined fluid flow pattern such as a substantially uniform and laminar flow to promote consistent cell growth across the surface of one or more of the substrates. For example, the fluid diffuser may be configured to receive fluid from the inlet and provide linear fluid flow to one or more substrates. In this manner, fluid may be introduced into a cavity of an enclosure through a relatively narrow inlet port, and evenly distributed across one or more substrates comprising a relatively wide dimension (e.g., diameter, length width).

In some embodiments, the fluid flow through the fluid diffuser may be assisted by gravity. In some embodiments, the apparatus may comprise an inlet configured to receive fluid and one or more outlets configured to output the fluid. Accordingly, in such embodiments, the fluid diffuser may be coupled between the inlet and the one or more substrates. In some embodiments, the fluid diffuser may be a separate component from, or integrated with, the inlet. The fluid diffuser may be disposed within a headspace of an enclosure.

In some embodiments, the fluid diffuser may have a dimension (e.g., diameter) that is less than a dimension of substrate. In some embodiments, the fluid diffuser may comprise a ratio of a dimension of the fluid diffuser to a dimension (e.g., diameter, length, width) of the substrate is between about 3:4 and about 1:1.

In some embodiments, the fluid diffuser may comprise a tapered surface configured to distribute fluid to the substrate in a predetermined flow pattern (e.g., to distribute fluid substantially evenly across a diameter of the substrate). The tapered surface may comprise one or more of a concave shape, conical shape, frustum shape, steps, and flared shape. For example, the tapered surface may be angled up to about 80 degrees relative to the substrate.

In some embodiments, the fluid diffuser may comprise a bicone. For example, the bicone may comprise a first surface and a second surface opposing the first surface. The first surface may be configured to receive the fluid and the second surface may be configured to receive the fluid from the first surface and distribute the fluid to the substrate. The fluid diffuser may be configured to enable a substantially uniform or laminar flow across a diameter of the substrate.

In some embodiments, the fluid diffuser may be radially symmetric. In some embodiments, a longitudinal axis of the fluid diffuser may be substantially perpendicular to the substrate. In some embodiments, the fluid diffuser and the substrate comprise a predetermined spacing of up to about 20 cm. For example, the fluid diffuser may be arranged at a higher elevation (e.g., above) relative to the substrate such that fluid may flow downward from the fluid diffuser to the substrate. For a substrate comprising a spiral (e.g., rolled) configuration, fluid may flow through each turn in parallel in a height-wise direction of the substrate.

In some embodiments, the fluid diffuser may comprise a plurality of openings. In some embodiments, the openings may comprise a total area of at least about 700 $\mu m^2$. The openings may be of any shape (e.g. circular, polygonal, slits, and combinations thereof). In some embodiments, the shape of the openings may be roughly circular, and each opening may comprise a diameter of about 30 $\mu m$, thus allowing the passage of growth media through the fluid diffuser. In other embodiments, the diameter of a circular opening may be between about 30 $\mu m$ and about 10 cm, or between about 0.5 cm and about 3 cm, including all values and sub-ranges in-between. In some embodiments, the plurality of openings of the fluid diffuser may be substantially equally spaced apart. In some embodiments, one or more of the size and frequency of the openings may change as a function of distance from the center of the fluid diffuser.

In some embodiments, the fluid diffuser may comprise only one portion. In other embodiments, the fluid diffuser may comprise more than one portion (e.g., at least a first portion and section portion). In some embodiments, one or more portions of the fluid diffuser may be substantially flat. In other embodiments, a first and second portion may be adjacent to each other, and these adjacent portions of the fluid diffuser are angled relative to each other, e.g., between about 90 degrees and about 170 degrees, including all values and sub-ranges in-between. For example, a larger angle between portions allows the fluid diffuser to have a smaller height. Furthermore, the aforementioned portions of the fluid diffuser may be angled relative to the plurality of substrates by up to about 80 degrees. In some embodiments, the fluid diffuser comprises an interface between the adjacent portions, e.g. the interface constituting a third portion. The interface may optionally comprise openings.

In some embodiments, the fluid diffuser may be configured to releasably engage to the enclosure and may be at least partially disposed in the cavity. For example, the fluid diffuser may be disposed within a headspace (e.g., empty space above the substrate) of an enclosure.

In some embodiments, an apparatus may comprise a plurality of fluid diffusers. In some embodiments, a fluid diffuser may be disposed above and/or below the substrate. For example, a fluid diffuser disposed above a substrate may distribute fluid downward over the substrate via gravity while a fluid diffuser disposed below a substrate may distribute fluid upward over the substrate against gravity.

Non-limiting exemplary embodiments of the fluid diffuser are illustrated and described in more detail with respect to FIGS. 1, 3A-3D, 4A-4C, 7A-7B, 9A, 10A-10C, 11A-11C, 13A-13F, 14A-14D, 15A-15D, and 18A-18E.

C. Substrates

The plurality of substrates in the apparatuses of the disclosure allow for high-density growth of meat products. For example, the substrates may comprise a surface configured to promote the adhesion, differentiation, and/or growth of cells to form a comestible meat product. Once grown to a predetermined size, the grown meat product may be separated from its respective substrate described in more detail herein. The substrates of the disclosure can be of any predetermined size.

In some embodiments, a substrate disposed within the cavity may be rolled about an axis (e.g., longitudinal axis of the enclosure or the substrate) to allow for high-density tissue growth and to increase structural rigidity of the substrate relative to a flat substrate. Increased rigidity due to the curvature of the substrate may enable a corresponding reduction in a thickness of the substrate, thereby further increasing a volume available for supporting a growth of a meat product. For example, a substrate may be arranged within the cavity and comprise a plurality of nested surfaces (e.g., spiral shape, rolled substrate) curved around a longitudinal axis and having a surface configured to support growth of the meat product. For example, the nested surfaces may comprise a tube within at least one other tube (e.g., inner tube, outer tube). A spiral substrate may be rotated around the longitudinal axis. In some embodiments, a rolled substrate may comprise an outer diameter of at least about 1 cm. In some embodiments, the substrate may comprise a thickness of at least about 1 $\mu m$.

In some embodiments, a rolled substrate may comprise more than one rotation about a predetermined axis. For example, the substrate may comprise a plurality of turns about an axis. That is, the substrate may wrap around itself a plurality of times to form a generally spiral shape. Each turn may comprise a complete rotation of the substrate around itself (e.g., relative to an innermost end of the substrate). In some embodiments, the substrate may be curved more than 360 degrees about an axis (e.g., to form more than one rotation or turn). In some embodiments, the substrate may be curved around a longitudinal axis of the enclosure or of the substrate.

In some embodiments, adjacent turns (e.g., layers, surfaces) of the substrate may comprise a predetermined spacing therebetween configured to support fluid flow and growth of the meat product. For example, the space between each turn of the substrate may allow fluid flow and the growth of the meat product on a surface of the substrate. That is, a fluid channel may form between adjacent turns.

In some embodiments, the substrate may comprise a first substrate portion and a second substrate portion formed separately from the first substrate portion. An end of the first substrate portion may be proximate to an end of the second substrate portion. In some embodiments, the end of the first substrate portion may be coupled to the end of the second substrate portion (e.g., coupled in an end-to-end configuration). In some embodiments, the end of first substrate portion may be overlapped with the end of the second substrate portion. In some of these embodiments, the substrate may comprise more than two substrate portions coupled in any combination.

In some embodiments, a rolled substrate (e.g., spiral substrate) may be configured to self-space in that the turns have a predetermined spacing relative to each other. For example, the substrate may be formed with a predetermined curvature that will naturally form a spiral shape. One or more protrusions on a surface of the substrate may ensure that each turn of the substrate is generally separated by a predetermined spacing. In some embodiments, the surface of the substrate may comprise one or more protrusions comprising a height of at least about 0.5 mm. Adjacent (e.g., proximate) protrusions may comprise a predetermined spacing along the surface of the substrate of up to about 20 cm. The predetermined spacing may be based on a radius of the substrate. For example, the predetermined spacing may increase from an innermost portion to the outermost portion of the substrate or vice versa. One or more of the protrusions may comprise a linear or non-linear shape. In some embodiments, one or more protrusions may be stamped into the surface of the substrate.

In some embodiments, the substrate may be angled (e.g., tilted) relative to ground (e.g., a ground surface). An angled substrate may promote growth of a meat product on a surface of the substrate relative to a substrate disposed perpendicular to ground. For example, the surface of the substrate facing away from ground may be configured to support adhesion, differentiation, and growth of the meat product. In some embodiments, the substrate and the enclosure may be angled relative to ground. In some embodiments, the enclosure may be configured to be placed on a ground surface. The substrate may define a longitudinal axis at an acute angle relative to the ground surface. In some embodiments, the acute angle may be at least about 85 degrees and include 90 degrees.

In some embodiments, each substrate may comprise dimensions including a width between about 10 cm and about 400 cm, including all values and sub-ranges in-between. In some embodiments, a plurality of substrates may include up to about 10,000,000 substrates, including all values and sub-ranges in-between.

In some embodiments, a spacing between adjacent (e.g., proximate) substrates may be between about 0.3 mm and about 5.0 cm, including all values and sub-ranges in-between.

In some embodiments, each substrate may comprise an area up to about 150,000,000 $cm^2$, including all values and sub-ranges in-between.

The substrates described herein may be sized and shaped to be placed into and/or integral with the apparatus. In some embodiments, a plurality of substrates may be used in a predetermined arrangement. In other embodiments, the plurality of substrates may be arranged in a parallel plate configuration (e.g., adjacent to each other) that allow multi-layered cell sheets to be formed in the apparatus. For example, the parallel plate configuration allows for fluid (e.g., growth media, nutrients) perfusion between the plates. In some embodiments, a shape of the fluid channel (described further below) may comprise the space between adjacent substrates.

In some embodiments, the substrates may be substantially planar. Additionally or alternatively, one or more substrates may be non-planar. For example, each substrate may comprise one or more of a rectangle, rod, bead, disk, spiral, coil, helix, corrugated, and sinusoidal shape (e.g., Raschig super rings). For example, a plurality of spherical beads configured to fill a cavity of the enclosure may have both a high density and a large surface area for growth of a meat product. Corresponding spaces between the spherical beads constitute the fluid channels of the apparatus. The substrates need not be parallel to one another, and may be angled and/or intersect relative to one another. A surface of the substrates may comprise one or more channels, grooves, and recesses configured as a fluid channel. In some embodiments, a substrate may extend across one or more dimensions (e.g., length, width, diameter) of the enclosure to better utilize an internal volume of the enclosure.

In some embodiments, the substrates may be disposed in an ordered or non-ordered arrangement. For example, a plurality of rod substrates may be arranged in a random pattern. The plurality of substrates may comprise a plurality of shapes (e.g., plates and rods, beads and coils). One or more of the substrates may be disposed in a symmetric or non-symmetric arrangement.

In some embodiments, the substrates may be configured to grow the meat product on opposite sides of the substrate. This may increase a volume of meat product grown on the substrate.

The substrates described herein support growth and retention of cells including, but not limited to, cells comprising one or more of endoderm, mesoderm, ectoderm, and combinations thereof. In some embodiments, cells comprise one or more cells from livestock (e.g. bovine, porcine, ovine, caprine), poultry (e.g. avian), game, aquatic animal species, and the like. In some embodiments, cells comprise one or more of myoblasts, mesangioblasts, myofibroblasts, mesenchymal stem cells, hepatocytes, fibroblasts, pericytes, adipocytes, epithelial, chondrocytes, osteoblasts, osteoclasts, pericytes, pluripotent stem cells, somatic stem cells, and endothelial cells. The cell types described herein further encompass any of their states of differentiation. For example, the cells include a myoblast, myotube, mature skeletal muscle, fibroblasts, tissue that includes cells and secreted extracellular matrix, adipocytes, adipose tissue, epithelial cells, epithelial tissue, vascular endothelium, combinations thereof, and the like. In some embodiments, cells may comprise vertebrate cells or non-vertebrate cells. In some embodiments, cells may comprise non-mammalian cells (e.g., insect cells, avian cells, fish cells, reptile cells, invertebrate cells). In some embodiments, cells may be genetically altered from their native state (e.g., genetic insertion, deletion or recombination). Examples of genetic alterations include cells that are engineered to overexpress a myogenic transcription factor. The cells may exist in different ratios, for example. In some embodiments, the apparatuses, systems, and methods disclosed herein may comprise the description in International Publication No. WO 2015/066377, filed on Oct. 30, 2014, International Publication No. WO 2017/124100, filed on Jan. 17, 2017, International Publication No. WO 2018/208628, filed on May 5, 2018, International Publication No. WO 2019/014652, filed on Jul. 13, 2018, International Application Serial No. PCT/US2020/034949, filed May 28, 2020, and U.S. Patent Application Ser. No. 62/938,087, filed Nov. 20, 2019, the contents of each of which are hereby incorporated by reference in its entirety.

In other embodiments, the substrates may be arranged in and/or are in conjunction with a three-dimensional lattice-like configuration that is exogenously provided (e.g., scaffold), (e.g., include three-dimensional, porous and/or lattice-like structures).

In other embodiments, the substrates do not comprise an exogenous scaffold, and are scaffold-less (e.g., exclude three-dimensional, porous and/or lattice-like structures that are not endogenously generated by the cells). Accordingly, in such embodiments, the cell sheets may be grown in the absence of an exogenous non-naturally secreted scaffold structure (but can, for example, be grown in the presence of a naturally secreted endogenously produced extracellular matrix (ECM)).

The substrates described herein may be composed of one or more of a solid material and a semi-solid material (e.g., hydrogel).

In some embodiments, the substrates may comprise textured surfaces to promote the adhesion, differentiation, and growth of the cells/cell sheets. In some embodiments, one or more substrates may be manipulated to enhance one or more characteristics (e.g., coated to improve adhesion).

Non-limiting exemplary embodiments of the substrates are illustrated and described in more detail with respect to FIGS. 1, 3A-3D, 5A-5B, 7A-7D, 8A-8C, 9A-9B, 10A-10C, 12A-12D, 13A-13F, 16A-16F, and 18A-18E.

D. Fluid Channels

Generally, the apparatuses of the disclosure comprise a plurality of fluid channels. At least one of the fluid channels is associated with at least one of the plurality of substrates. Fluid may be configured to flow in one direction through the plurality of fluid channels. For example, fluid may flow from a higher elevation to a lower elevation along a predetermined path (e.g. linear path). In some embodiments, a fluid channel may form between adjacent substrates or between adjacent turns (e.g., rotations, layers, surfaces) of a rolled substrate. For example, a spiral substrate may comprise a spiral fluid channel. In some embodiments, the substrate may comprise one or more spacing features (e.g., protrusions) configured to maintain a predetermined width of a fluid channel. The plurality of fluid channel may have the same or different shape and/or dimensions.

In some embodiments, each fluid channel may have a width between about 0.3 mm and about 5.0 cm, including all values and sub-ranges in-between.

In some embodiments, one or more of the fluid channels may be planar. In some embodiments, each of the fluid channels may be between adjacent substrates. In some embodiments, the plurality of fluid channels may be substantially parallel to each other.

Non-limiting exemplary embodiments of the fluid channels are illustrated and described in more detail with respect to FIGS. 1, 3A-3D, 5A-5B, 7A-7D, 8A-8C, 9A-9B, 10A-10C, 12A-12D, 13A-13F, 16A-16F, and 18A-E.

E. Separator

In some embodiments, the apparatus may include one or more separators configured to separate the meat product from the plurality of substrates in a predetermined manner. For example, a separator such as a fluid nozzle may be configured to receive and distribute a fluid (e.g., liquid, water) to one or more substrates in a predetermined flow pattern to separate a grown meat product from the substrate such that the meat product may be recovered in portions comprising a predetermined size. For example, the meat product may be separated and recovered from the apparatus as a continuous tissue sheet (e.g., maintaining integrity of the tissue sheet) to maintain a desired shape or texture, rather than a set of unconnected collection of cells. For example, the continuous tissue sheet may slide off the substrate for recovery. In some embodiments, sterility of the system may be maintained while separating tissue from the substrate which may increase efficiency and decrease run times. For example, the separator may be configured to operate without opening the enclosure.

In some embodiments, one or more of the separators may be integral or distinct from the enclosure of the apparatus. For example, a first separator may be disposed within a sidewall of the enclosure, and a second separator may be disposed within a cavity of the enclosure. For example, the second separator may be coupled (e.g., fastened) to one or more of a fluid diffuser, substrate, or other component arranged within the apparatus. One or more separators may be configured to translate and/or rotate relative to the substrates to aid a meat separation process. For example, a separator may be configured to translate radially between a center and periphery of the enclosure to distribute fluid across a greater volume of the substrate. Additionally or alternatively, a separator may be configured to rotate to distribute fluid in a predetermined (e.g., periodic) pattern to separate meat across a greater volume of the substrate.

Figure 17A:
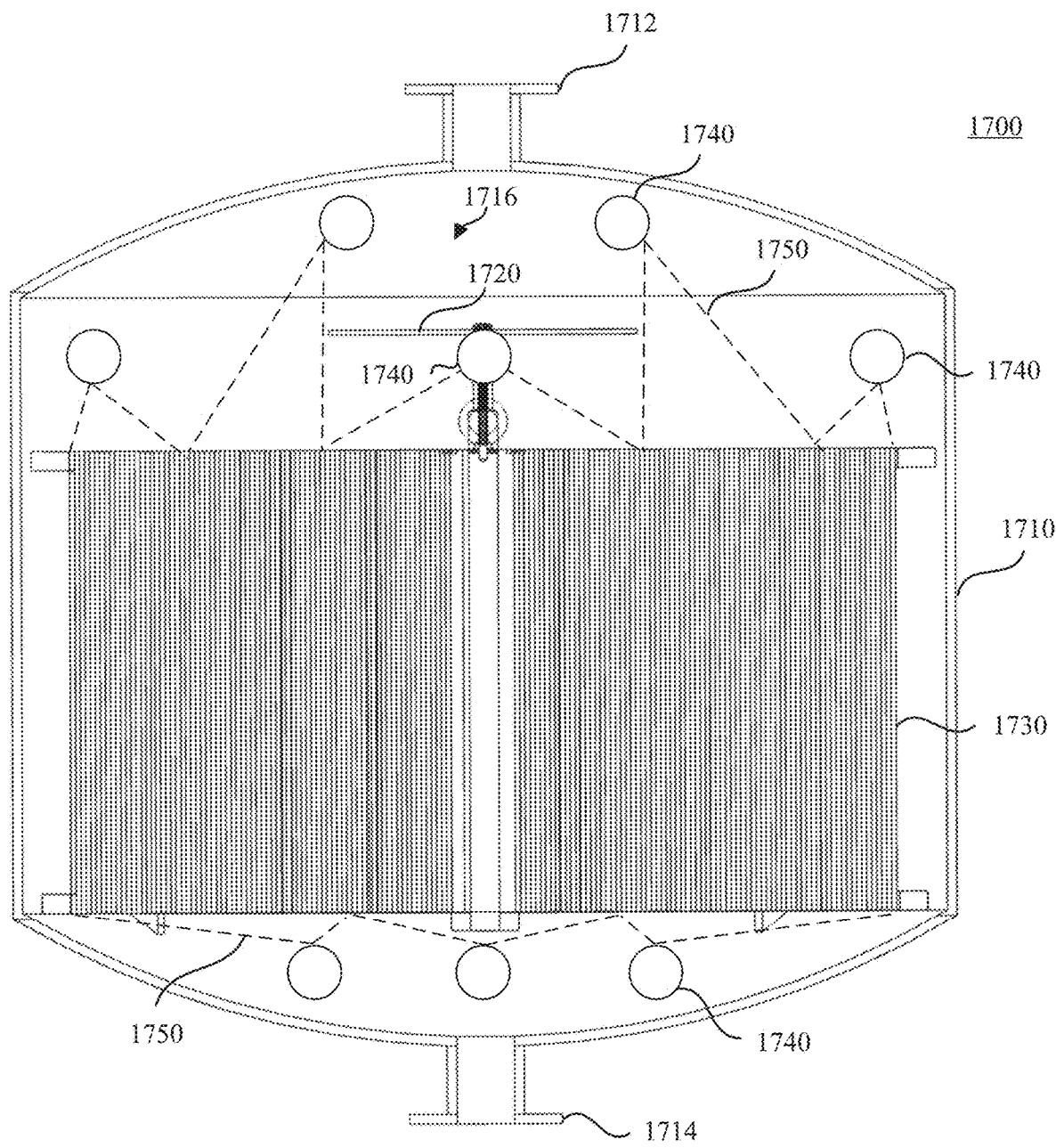
FIG. 17A is an illustrative schematic diagram of an exemplary embodiment of a separator of an apparatus for preparing a meat product.

FIG. 17A is a schematic diagram of an apparatus (1700) comprising a plurality of separators (1740). The apparatus (1700) may comprise an enclosure (1710) comprising an inlet (1712), an outlet (1714), and further defines a cavity (1716). Disposed within the cavity (1716) may be a fluid diffuser (1720), and at least one substrate (1730). In some embodiments, one or more of the separators (1750) (e.g., fluid nozzles) may be coupled to an inner wall of the enclosure (1710). For example, the separators (1750) may be integrated with and project from the enclosure (1710) and into the cavity (1716). The separators (1750) may be configured to distribute fluid to the substrate (1730) in a predetermined fluid flow pattern (1750). In some embodiments, a fluid flow pattern may comprise one or more of a fan, spray, jet, column, solid stream, full cone, hollow cone, mist, intermittent, droplet, rotary, or static pattern. For example, the fluid flow pattern may comprise a small diameter (e.g., concentrated stream) having a relatively high pressure or a large diameter (e.g., diffuse spay) having a relatively low pressure. In some variations, the fluid flow may comprise a pressure between about 0 PSI and about 50 PSI. For the sake of illustration, FIG. 17A depicts a separator (1740) comprising a fluid flow pattern (1750) including a fan pattern. For example, fluid (1750) may be directed in parallel and/or perpendicular to an interface between the meat product and the substrate (1730) as described in more detail with respect to FIGS. 17B and 17C. In some embodiments, a separator (1750) may be disposed within one or more of a side wall, top, bottom, lid, headspace (e.g., empty space above the substrate (1730)), etc. of the enclosure (1710).

The fluid diffuser (1720) may be disposed between the inlet (1712) and at least one substrate (1730). For example, the fluid diffuser (1720) may be disposed within a headspace of the enclosure (1710). Any of the fluid diffuser (1720), substrate (1730), and separator (1740) may be removable or fixed to the enclosure (1710). In some embodiments, one or more fluids (e.g., liquid, growth media, gas) may be configured to flow in a direction from the inlet (1712) to the outlet (1714). The fluid diffuser (1720) may be configured to receive and distribute the fluid in a predetermined flow pattern to one or more substrates (1730). In some embodiments, an enclosure (1710) may comprise a plurality of inlets, outlets, and separators (1740).

Fluid distributed from a separator (1750) may be configured to flow in any predetermined direction and/or pattern. For example, a first separator may be configured to distribute fluid to an innermost portion of the substrate (1730) (e.g., center of FIG. 17A) from a higher elevation to a lower elevation (e.g., downward), a second separator may be configured to distribute fluid to an outermost portion of the substrate (1730) from the side (e.g., from a sidewall of enclosure (1710), and so forth.

Figure 17B:
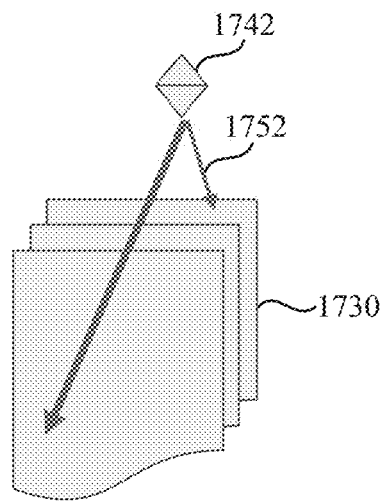
FIGS. 17B and 17C are illustrative schematic diagrams of exemplary embodiments of separator and substrate configurations.
Figure 17C:
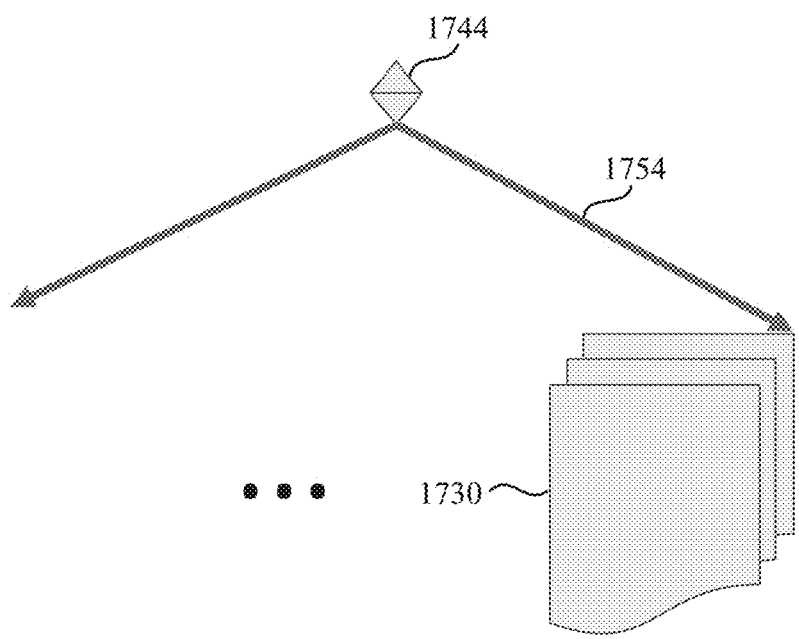

FIGS. 17B and 17C are schematic perspective views of separator configurations relative to a substrate. In particular, FIG. 17B depicts a separator (1742) (e.g., fluid nozzle) configured to distribute a fan-like fluid flow pattern (1752) perpendicular to the substrate (1730) (e.g., across a thickness of the substrate (1730)). For example, the perpendicular flow pattern (1752) forms a flat fan spray pattern (e.g., fluid sheet) that intersects each of the parallel plates (or turns) of the substrate (1730). In some embodiments, the separator may be configured to direct fluid towards the substrate at a predetermined angle that may be up to about 10 degrees relative to the substrate. For example, a portion of the substrate (1730) directly beneath the separator (1742) may receive fluid at 0 degrees and other portions of the substrate (1730) may receive fluid at a predetermined angle. In some embodiments, the separator (1742) may be pitched and/or traversed relative to the substrate (1730) to distribute the spray pattern across a larger surface area of the substrate (1730). A separator (1742) in the perpendicular configuration depicted in FIG. 17B may be configured to separate tissue on opposite sides of a substrate. For example, tissue that does not directly receive fluid flow from the nozzle may separate from the substrate (1730) through indirect fluid flow.

FIG. 17C depicts a separator (1744) (e.g., fluid nozzle) configured to distribute a fan-like fluid flow pattern (1754) parallel to the substrate (1730). For example, the parallel flow pattern (1754) forms a flat fan spray pattern (e.g., fluid sheet) that intersects one of the parallel plates (or turns) of the substrate (1730) (e.g., rearward most plate in FIG. 17C). In FIG. 17C, a portion of the substrate (1730) directly beneath the separator (1744) may receive fluid at 0 degrees. In some embodiments, the separator (1744) may be rolled and/or traversed perpendicularly relative to the substrate (1730) to distribute the spray pattern across each of the plates (or turns) of the substrate (1730).

In some embodiments, the fluid flow pattern may comprise an angle of up to about 120 degrees. For example, the fluid may comprise a fluid stream in a fan shape having an angle of up to about 120 degrees. In some embodiments, in order to reduce fluid stream velocities, the substrates may not be immersed in fluid (e.g., flooded) when receiving the fluid stream having the predetermined fluid flow pattern. That is, the enclosure may be at least partially drained of fluid prior to tissue separation. In some embodiments, the substrates may receive a column of fluid (e.g., having a circular cross-section) in parallel to the substrate. In some embodiments, the fluid may comprise a linear velocity between about 0.003 m/sec and about 0.3 m/sec, between about 0.03 m/sec and about 0.3 m/sec, between about 0.03 m/sec and about 3.0 m/sec, and between about 0.3 m/sec and about 3.0 m/sec, including all values and sub-ranges in-between. In some embodiments, the separator may be configured to rotate (e.g., pitch, yaw, roll) about a predetermined axis when the fluid is directed at the meat product and substrate. In some embodiments, a separator may be separated from a substrate by up to about 10 cm, up to about 15 cm, up to about 30 cm, and up to about 50 cm, including all values and sub-ranges in-between. In some embodiments, tissue may be separated from the substrate via indirect contact with the fluid stream. For example, a fluid stream redirected from a sidewall of an enclosure may comprise sufficient energy to separate tissue from a substrate.

Non-limiting exemplary embodiments of the separator are illustrated and described in more detail with respect to FIGS. 17A-17C. Any of the embodiments systems and apparatuses described herein may comprise one or more separators.

F. Collector

In some embodiments, the apparatus may further include one or more collectors coupled to the enclosure of the apparatus receive and collect the meat product from the plurality of substrates.

In some embodiments, the collector of the disclosure may comprise a plurality of openings, e.g. comprising a total area of at least about 25 $\mu m^2$. For example, each opening may comprise a diameter of between about 30 $\mu m$ and about 2.5 cm, including all values and sub-ranges in-between.

In some embodiments, the collector may be a separate component from, or integrated with, the enclosure. In some embodiments, the collector may be configured to releasably engage to the enclosure and is coupled to a distal end of the plurality of substrates. In some embodiments, where the collector is external to the enclosure, the collector comprises one or more openings comprising an area of at least about 20 $\mu m^2$.

Non-limiting exemplary embodiments of the collector are illustrated and described in more detail with respect to FIGS. 1, 3A-3D, and 6A-6C.

II. SYSTEMS

Described herein are systems that include one or more of the components necessary to generate a meat product using the apparatuses described herein. For example, the systems described herein may support, grow, separate, and recover one or more cell sheets cultured on a substrate of an apparatus. Generally, the systems described herein include one or more of an apparatus of the disclosure, a fluid pump, a fluid source, and a controller (including memory, a processor, and computer instructions).

In some embodiments, an apparatus for preparing a meat product may comprise an enclosure comprising a cavity and a substrate arranged within the cavity. The substrate may comprise a spiral and a surface configured to support growth of the meat product. A fluid diffuser may be coupled to the enclosure and configured to distribute fluid to the substrate in a predetermined flow pattern. In some embodiments, a ratio of a dimension of the fluid diffuser to a dimension of the substrate may be between about 3:4 and about 1:1.

In some embodiments, an apparatus for preparing a meat product may comprise an enclosure defining a cavity and a substrate arranged within the cavity. The substrate may be configured to support growth of the meat product. A fluid diffuser comprising a tapered surface may be configured to distribute fluid to the substrate in a predetermined flow pattern.

Generally, a system for preparing a meat product comprises: (a) an apparatus comprising one or more substrates;

(b) a fluid pump coupled to the apparatus; (c) a fluid source coupled to the fluid pump; (d) a controller coupled to the fluid pump, wherein the controller is configured to generate a first fluid pump signal to generate the meat product on the substrates and generate a second fluid pump signal to separate the meat product from the substrates. For example, the fluid pump is configured to provide fluid flow of growth media (e.g., culture media) to the apparatus. The controller is configured to control the fluid flow rate and other conditions within the apparatus (e.g., temperature, pressure).

In some embodiments, a first fluid pump signal may be configured to provide a substantially uniform and laminar flow of the fluid to the plurality of substrates using the fluid pump. In exemplary embodiments, a first fluid pump signal comprises a first flow rate and the second fluid pump signal comprises a second flow rate higher than the first flow rate. In some of these embodiments, the first fluid pump signal comprises a flow rate of up to about 3.0 meters per second and the second fluid pump signal corresponds to a linear velocity within the apparatus of up to about 10 meters per second. The fluid source typically comprises growth media and/or cells. The system is configured to grow the meat on the substrate for at least about 1 day, but depending on the nature of the cells being grown, this can be extended out to 3, 5, or more days; for example, meat may be grown for one or more weeks. Optionally, one or more sensors of the system are configured to measure one or more parameters of the fluid and cell sheet state.

FIG. 1 is an illustrative block diagram of an embodiment of a system (100) comprising an apparatus (110), fluid pump (130), fluid source (140), controller (150), and sensors (160). In some embodiments, the apparatus (110) comprises one or more of an inlet (112), fluid diffuser (114), substrate (116), cells (118), collector (120), outlet (122), rotator (124), and separator (126). One or more fluid pumps (130) may be in fluid communication with the apparatus (110) and a fluid source (140). The fluid source (140) (e.g., fluid reservoir) is configured to store fluid (142) (e.g., growth media, cells, liquid, and combinations thereof). The fluid pump (130) is configured to pump and/or recirculate the fluid (142) through a set of fluid conduits (132) forming a closed circuit (closed loop path) of the system (100). The system (100) may comprise one or more fluid sources (140) and fluids (142). For example, growth media may be used to grow a meat product in the apparatus (110) while a separation fluid (e.g., water) may be used to separate the grown meat product from a substrate (116).

A. Fluid

As used herein, the fluid that may circulate throughout the system may comprise one or more of a growth media (e.g. cell culture media), nutrients, metabolites, signaling factors, liquid, water, gas, and compositions configured for meat product growth. In some embodiments, the fluid may further comprise cells used to seed the substrates that grow the comestible meat product. In some embodiments, a fluid may comprise an additive comprising one or more of an amino acid, anti-foaming agent, sheer protectant, and protein.

In some embodiments, cell culture media may comprise liquid cell culture media or dehydrated cell culture media. Dehydrated cell culture media or dry powder media (DPM) may comprise a mixture of amino acids, salts, glucose and other chemicals necessary for the growth of cells. DPM may be hydrated with a liquid such as purified water to form liquid cell culture media.

In some embodiments, the cell culture media may comprise a complete composition sufficient to grow cells by itself without any other additions. That is, complete cell culture media contains all components necessary for the growth of cells being grown in the bioreactor. In some embodiments, a complete cell culture media may comprise one or more of water, buffer, and nutrients that support cell growth. In some embodiments, the cell culture media may comprise an incomplete composition configured to grow cells with the addition of at least one other composition. For example, an incomplete cell culture media composition may be formed without components sensitive to oxidation. In some variations, the pH of the incomplete cell culture media may be different than the pH of the complete cell culture media.

B. Fluid Pump

In some embodiments, one or more fluid pumps may be coupled to a fluid conduit in fluid communication with the apparatus to generate a predetermined fluid flow rate through the apparatus to aid one or more of growth of a meat product and separation of the meat product from a substrate. In some embodiments, a fluid pump may comprise one or more of a positive displacement pump (e.g., peristaltic pump), centrifugal pump, combinations thereof, and the like. One or more fluid sources may be coupled to the fluid pump.

In some embodiments, the fluid pump may be configured to output a first fluid flow that may be regulated by a fluid diffuser to provide a substantially uniform and laminar flow of the fluid to a plurality of substrates, and output a second fluid flow configured to separate a meat product from the substrate. In some embodiments, the second fluid flow may comprise a flow rate of up to about 10 meters per second. The fluid pump may be configured to operate over extended periods of time (e.g., days, weeks). For example, the fluid pump may be configured to pump fluid for at least 1 day (e.g., 3, 5, 10, 15, 20, 25, 30 days).

C. Fluid Source

In some embodiments, one or more fluid sources (e.g., fluid reservoir, gas generator) may be coupled to one or more fluid pumps and apparatuses for preparing a meat product. The fluid source may be configured to store fluid. The fluid source may comprise growth media comprising one or more cells. For example, the fluid source may be configured to store different fluid compositions for different growth stages of a meat product. The fluid source may be configured to store recirculated media and separately store fresh media. In some embodiments, one or more sensors may be coupled to the fluid source to measure one or more parameters of the fluid such as pH, dissolved gas concentration, osmolality, turbidity, hydration, conductivity, absorbance, nutrient concentration, waste concentration, ion concentration, oxygen concentration, temperature, and the like.

In some embodiments, the fluid source may be configured to hold air bubbles generated by the fluid pump and thus prohibit formation of an air bubble through a fluid conduit. That is, air bubbles may be held in a fluid source upstream of a conduit. For example, the fluid source may contain a cavity configured to hold a volume of fluid where the fluid fills the cavity up to a predetermined height that is above an inlet height and outlet height of the fluid source. The space above the predetermined height in the cavity of the fluid source may contain air. During use, operation of the pump may generate one or more air bubbles that may be passed into the fluid source. When the air bubble passes into the fluid source, the air within the bubble may be held within the fluid source such that fluid without air bubbles may be output from an outlet of the fluid source and into the apparatus. Thus, air bubbles may be prohibited from forming in the conduits of the apparatus and may promote uniform and laminar flow of fluid though an apparatus.

D. Controller

Generally, the systems described herein may include at least one apparatus for preparing a meat product and corresponding controller coupled to a fluid pump and sensors. In some embodiments, a sensor may be configured to generate signal data. The signal data may be received by a controller and used to generate fluid pump signals to control the fluid pump.

Referring to FIG. 1, in some embodiments, a controller (150) may be coupled to one or more of apparatus (110), fluid pump (130), fluid source (140), and sensors (160). The controller (150) may comprise one or more of a processor (152), memory (154), input device (156), and communication device (158). In some embodiments, the controller (150) may be configured to receive data from one or more of the apparatus (110), fluid pump (130), fluid source (140), and sensors (160). In some embodiments, the sensors (160) may comprise one or more of a flow sensor, temperature sensor, pH sensor, dissolved gas sensor, pressure sensor, optical sensor, turbidity sensor, and the like. In some embodiments, the data generated by the sensors (160) may be processed and used to monitor and/or control one or more components of the system (100).

The controller (150) may accordingly monitor and/or control preparation and/or recovery (e.g., separation) of a comestible meat product. As described in more detail herein, the controller (150) may be coupled to one or more networks using a communication device (158). The controller (150) may include a processor (152) and memory (154) coupled to an input device (156).

The controller (150) may include computer instructions for operation thereon to cause the processor (152) to perform one or more of the steps described herein. In some embodiments, the computer instructions may be configured to cause the processor to receive signal data from the sensors, generate fluid pump signals, and output data a user. The controller (150) may include one or more processors (152) and one or more machine-readable memories (154) in communication with the one or more processors (152). The processor (152) may incorporate data received from memory (154) and user input to control the system (100). The memory (154) may further store instructions to cause the processor (152) to execute modules, processes, and/or functions associated with the system (100). The controller (150) may be connected to and control one or more of sensor (160), fluid pump (130), communication device (158), and the like by wired and/or wireless communication channels.

The controller (150) may be implemented consistent with numerous general purpose or special purpose computing systems or configurations. Various exemplary computing systems, environments, and/or configurations that may be suitable for use with the systems and apparatuses disclosed herein may include, but are not limited to software or other components within or embodied on a server or server computing devices such as routing/connectivity components, multiprocessor systems, microprocessor-based systems, distributed computing networks, personal computing devices, network appliances, portable (e.g., hand-held) or laptop devices. Examples of portable computing devices include smartphones, personal digital assistants (PDAs), cell phones, tablet PCs, wearable computers taking the form of smartwatches and the like, and portable or wearable augmented reality devices that interface with the patient's environment through sensors and may use head-mounted displays for visualization, eye gaze tracking, and user input.

The processor (152) may be any suitable processing device configured to run and/or execute a set of instructions or code and may include one or more data processors, image processors, graphics processing units, physics processing units, digital signal processors, and/or central processing units. The processor (152) may be, for example, a general purpose processor, Field Programmable Gate Array (FPGA), an Application Specific Integrated Circuit (ASIC), combinations thereof, and the like. The processor (152) may be configured to run and/or execute application processes and/or other modules, processes and/or functions associated with the system and/or a network associated therewith. The underlying device technologies may be provided in a variety of component types including metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, combinations thereof, and the like.

In some embodiments, the memory (154) may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, combinations thereof, and the like. As used herein, database refers to a data storage resource. The memory (154) may store instructions to cause the processor (152) to execute modules, processes, and/or functions associated with the controller (150), such as calibration, signal processing, sensor analysis, notification, communication, authentication, user settings, combinations thereof, and the like. In some embodiments, storage may be network-based and accessible for one or more authorized users. Network-based storage may be referred to as remote data storage or cloud data storage. Signal data and analysis stored in cloud data storage (e.g., database) may be accessible to authorized users via a network, such as the Internet. In some embodiments, database may be a cloud-based FPGA.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for a specific purpose or purposes.

Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs); holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other embodiments described herein relate to a computer program product, which may include, for example, the instructions and/or computer code disclosed herein.

The systems, apparatuses, and methods described herein may be performed by software (executed on hardware), hardware, or a combination thereof. Hardware modules may include, for example, a general-purpose processor (or microprocessor or microcontroller), a field programmable gate array (FPGA), an application specific integrated circuit (ASIC), combinations thereof, and the like. Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

The input device (156) may permit a user to interact with and/or control the system (100) directly and/or remotely. For example, the input device (156) may be configured for a user to input commands and an output device for a user and/or other users (e.g., technicians) to receive output (e.g., view system data on a display device) related to operation of the system (100). In some embodiments, a communication device (158) may permit the controller (150) to communicate with one or more of a network (e.g., Internet), remote server, and database as described in more detail herein.

The input device (156) may serve as a communication interface between a user (e.g., operator) and the controller (150). In some embodiments, the input device (156) may include an output device (e.g., touch screen and display) and be configured to receive input data and output data from one or more sensors, input device, output device, network, database, and server. For example, signal data generated by a sensor may be processed by processor (152) and memory (154), and output visually by one or more output devices (e.g., display). Signal data, sensor data, and/or meat product data may be received by controller (150) and output visually, audibly, and/or through haptic feedback through one or more output devices. As another example, user control of an input device (e.g., joystick, keyboard, touch screen) may be received by input device (156) and then processed by processor (152) and memory (154) to output a control signal to one or more components of the system (100). In some embodiments, the input device (156) may function as both an input and output device (e.g., a handheld controller configured to generate a control signal while also providing haptic feedback to a user).

An output device may output data and may include one or more of a display device, audio device, and haptic device. The display device may be configured to display a graphical user interface (GUI). The input device (156) may include an integrated display and/or video output that may be connected to output to one or more generic displays, including remote displays accessible via the internet or network. The output data may also be encrypted to ensure privacy and all or portions of the output data may be saved to a server or database. A display device may permit a user to view signal data, calibration data, tissue data, image data, cell sample data, system data, fluid data, patient data, and/or other data processed by the controller (150). In some embodiments, an output device may include a display device including at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, holographic display, combinations thereof, and the like.

An audio device may audibly output sensor data, meat product data, fluid data, pump data, system data, alarms and/or warnings. For example, the audio device may output an audible warning upon malfunction of a fluid pump and/or sensor. In some embodiments, an audio device may include at least one of a speaker, piezoelectric audio device, magnetostrictive speaker, and/or digital speaker. In some embodiments, a user may communicate with other users using the audio device and a communication channel.

A haptic device may be incorporated into one or more of the input and output devices to provide additional sensory output (e.g., force feedback) to the user. For example, a haptic device may generate a tactile response (e.g., vibration) to confirm user input to an input device (e.g., joystick, keyboard, touch surface). In some embodiments, the haptic device may include a vibrational motor configured to provide haptic tactile feedback to a user. Additionally or alternatively, haptic feedback may notify a user of an error such as pump malfunction and/or fluid disconnection. This may prevent potential harm to the system.

Some embodiments of an input device may include at least one switch configured to generate a control signal. For example, the input device may be configured to control one or more pumps to control fluid flow rate. In some embodiments, the input device may include a wired and/or wireless transmitter configured to transmit a control signal to a wired and/or wireless receiver of a controller (150). For example, an input device may include a touch surface for a user to provide input (e.g., finger contact to the touch surface) corresponding to a control signal. An input device including a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In embodiments of an input device including at least one switch, a switch may include, for example, at least one of a button (e.g., hard key, soft key), touch surface, keyboard, analog stick (e.g., joystick), directional pad, pointing device (e.g., mouse), trackball, jog dial, step switch, rocker switch, pointer device (e.g., stylus), motion sensor, image sensor, and microphone. A motion sensor may receive user movement data from an optical sensor and classify a user gesture as a control signal. A microphone may receive audio and recognize a user voice as a control signal.

In some embodiments, the controller (150) may be in communication with other devices via one or more wired and/or wireless networks. The communication device (156) may facilitate communication with other devices over one or more external ports (e.g., Universal Serial Bus (USB), multi-pin connector) configured to couple directly to other devices or indirectly over a network (e.g., the Internet, wireless LAN).

In some embodiments, the communication device (156) may include a radiofrequency receiver, transmitter, and/or optical (e.g., infrared) receiver and transmitter configured to communicate with one or more devices and/or networks. The communication device (156) may communicate by wires and/or wirelessly. In some embodiments, the communication device (156) may include radiofrequency (RF) circuitry (e.g., RF transceiver) including one or more of a receiver, transmitter, and/or optical (e.g., infrared) receiver and transmitter configured to communicate with one or more devices and/or networks. RF circuitry may receive and transmit RF signals (e.g., electromagnetic signals). The RF circuitry converts electrical signals to/from electromagnetic signals and communicates with communications networks and other communications devices via the electromagnetic signals. The RF circuitry may include one or more of an antenna system, an RF transceiver, one or more amplifiers, a tuner, one or more oscillators, a digital signal processor, a CODEC chipset, a subscriber identity module (SIM) card, memory, and the like. A wireless network may refer to any type of digital network that is not connected by cables of any kind.

Examples of wireless communication in a wireless network include, but are not limited to cellular, radio, satellite, and microwave communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, near-field communication (NFC), radio-frequency identification (RFID), Wireless Fidelity (Wi-Fi) (e.g., IEEE 802.11a, IEEE 802.11b, IEEE 802.11g, IEEE 802.11n), Voice over Internet Protocol (VoIP), Wi-MAX, a protocol for email (e.g., Internet Message Access Protocol (IMAP), Post Office Protocol (POP)), instant messaging (e.g., eXtensible Messaging and Presence Protocol (XMPP), Session Initiation Protocol for Instant Messaging, Presence Leveraging Extensions (SIMPLE), Instant Messaging and Presence Service (IMPS)), Short Message Service (SMS), or any other suitable communication protocol. Some wireless network deployments combine networks from multiple cellular networks or use a mix of cellular, Wi-Fi, and satellite communication.

In some embodiments, a wireless network may connect to a wired network in order to interface with the Internet, other carrier voice and data networks, business networks, and personal networks. A wired network is typically carried over copper twisted pair, coaxial cable, and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, wireless personal area networks (PAN) (e.g., Bluetooth, Bluetooth Low Energy), and virtual private networks (VPN). As used herein, network refers to any combination of wireless, wired, public, and private data networks that are typically interconnected through the Internet, to provide a unified networking and information access system.

E. Exemplary Embodiments

Exemplary embodiments of the apparatus and system will be described with respect to the figures. As shown in FIG. 1, an embodiment of an apparatus (110) comprises one or more of an inlet (112), fluid diffuser (114), substrate (116), collector (120), outlet (122), an optional rotator (124), and separator (126). In some embodiments, the apparatus is rotatable about a rotation axis (e.g., rotation axis parallel to ground). The apparatus (110) may be configured for large-scale production of cell sheets that form a meat product. In some embodiments, the apparatus comprises dimensions comprising an internal cavity volume of at least 1 L. For example, the apparatus (110) may comprise an internal volume between about 25 L and about 200 L, between about 100 L and about 500 L, between about 500 L and about 1,000 L, and between about 1,000 L and about 20,000 L, including all values and sub-ranges in-between.

In some embodiments, the apparatus (110) is coupled to one or more fluid pumps (130), fluid conduits (132), fluid sources (140), and sensors (160). For example, different fluid conduits (132) coupled to respective fluid pumps (130) and fluid reservoirs (140) may be configured to circulate separate fluids (142) (e.g., different growth media compositions, liquids, gas) to the cells (118) in the apparatus (110) to aid efficient cell growth over a plurality of meat product growth stages. In some embodiments, the apparatus (110) is coupled to at least one controller (150). For example, optional sensors (160) may be coupled to respective sensor controllers.

In some embodiments, one or more portions of the apparatus (110) may be designed to be reusable (e.g., used multiple times, sterilized and re-used) such as the enclosure, fluid diffuser (114), substrate (116), collector (120), and separator (126). Additionally or alternatively, one or more components of the apparatus (110) may be designed to be disposed after a predetermined number of uses. In some embodiments, any of the components of the apparatus may be substantially non-degradable.

As described herein, the apparatuses and systems as described herein may generate a variety of mechanical and fluid dynamic forces such as interstitial flow during long-term growth of a meat product (e.g., days, weeks, months) in a sealed three-dimensional environment.

FIGS. 2A-9B depict an apparatus for preparing a meat product. FIGS. 2A-2E depict respective perspective and side views of respective apparatuses (200, 250) for preparing a meat product. The apparatus (200) may comprise an enclosure (210) defining a cavity therein. The enclosure (210) may comprise at least one inlet (220) configured to receive fluid from, for example, a fluid conduit coupled to a fluid source (not shown), and at least one outlet (230) configured to output one or more of the fluid and a meat product (e.g., cell sheets). For example, the outlet (230) may comprise a sufficient size to output a meat product separated from one or more substrates within the enclosure (210). In some embodiments, the inlet (210) is disposed on a first side of the enclosure (210) and the outlet (230) is disposed on a second side of the enclosure (210) opposite the first side. In some embodiments, at least one inlet (220) may be configured to both receive and output fluid. Similarly, at least one outlet (230) may be configured to both receive and output fluid. For example, fluid flow may begin in a first direction (e.g., inlet (220) to outlet (230)) and may reverse (e.g., outlet (230) to inlet (220)) during one or more steps of a method of preparing a meat product. As shown in FIGS. 2A-2E, the enclosure (210, 260) may have a generally cylindrical shape, although the enclosure (210, 260) is not limited by any particular shape. In some embodiments, the enclosure (210, 260) may comprise a volume of at least 25 L. For example, the enclosure (210, 260) may comprise a volume between about 100 L and about 500 L.

In some embodiments, an apparatus (200) may comprise one or more inlets (220) configured to receive fluid such as a growth media, liquid, and/or gas. For example, a fluid pump may be configured to be in fluid communication with one or more of the inlets (220) of the apparatus (200) via respective fluid conduits. In some embodiments, an enclosure (210) of an apparatus (200) may define the inlet (220) along an upper surface (e.g., top) of the apparatus (200) relative to a ground surface. This allows fluid flow through the apparatus (200) from a first elevation (e.g., height of an inlet (220)) to a second elevation (e.g., height of an outlet (230)) lower than the first elevation. This configuration may promote drainage and complete circulation of fluid through the apparatus (200).

In some embodiments, the inlet (220) may comprise a valve (not shown) configured to, for example, control fluid flow and prevent backflow of fluid into a fluid conduit. In some embodiments, the inlet (220) may be disposed on one or more sides (e.g., sidewalls) of the apparatus (200). In some embodiments, respective inlets (220) may be configured for different steps of a meat production process (e.g., sterilization, seeding, growth, separation). For example, different inlets may be configured to receive sterilization fluid, growth media, and separation fluid to optimize fluid distribution throughout the vessel for different stages of a meat production process. For instance, different inlets may receive growth media having different states (e.g., metabolite adjusted, re-oxygenated). In some embodiments, one or more inlets (220) of the apparatus (200) may be configured for access to one or more of the substrates disposed within a cavity of the enclosure (210). For example, an inlet (210) may be configured to receive fluid comprising cells used to seed one or more substrates. In some embodiments, the inlet (220) may comprise a connector (e.g., adapter, fitting) configured to couple to one or more of the fluid conduits and fluid diffuser. In some embodiments, the outlet (230) may comprise a connector (e.g., adapter, fitting) configured to couple to one or more of the fluid conduits and collector.

Similar to the apparatus (200) of FIGS. 2A and 2B, FIGS. 2C-2E depict an apparatus (250) comprising an enclosure (260), inlet (270), and outlet (280). In some embodiments, the apparatus (250) may be provided at an angle (e.g., off-axis) relative to an axis (290) perpendicular to ground when preparing a meat product. That is, the apparatus (250) may be tilted during use. In some embodiments, the apparatus (250) may be angled up to about 5 degrees relative to the axis (290) or at least about 85 degrees relative to a ground surface. Growing a continuous tissue sheet at a non-perpendicular or non-parallel angle relative to ground may improve adhesion of a cell culture to the substrate while also allowing gravity to assist in fluid flow over a substrate. This may also enable the enclosure to be scaled vertically in size, thereby optimizing a physical footprint of the apparatus (250). In some embodiments, a longitudinal axis of the internal components of the apparatus (250) may be tilted at an angle relative to the axis (290) while a longitudinal axis of the enclosure (250) itself may be parallel to the axis (290). For example, a longitudinal axis of one or more substrates and/or a fluid diffuser may be tilted relative to the axis (290) while each of the inlet (270) and outlet (280) may be parallel to the axis (290). In some embodiments, the enclosure may be configured to be placed on a ground surface. The longitudinal axis (290) may be at an acute angle relative to the ground surface. In some embodiments, the acute angle is at least about 85 degrees. In some embodiments, the surface of the substrate facing away from the ground surface is configured to support growth of the meat product. Any of the apparatuses described herein may be oriented and used at an angle relative to an axis perpendicular to ground.

Figure 3A:
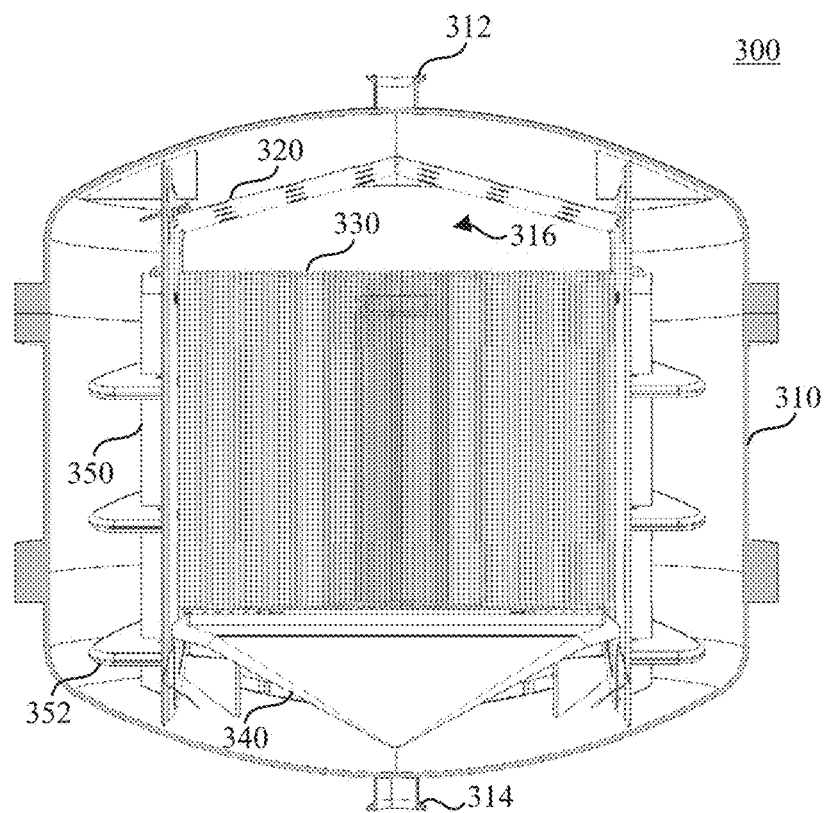
FIG. 3A is an illustrative cross-sectional side view of an exemplary embodiment of an apparatus for preparing a meat product.

FIG. 3A is a cross-sectional side view of an apparatus (300) for preparing a meat product. The apparatus (300) comprises an enclosure comprising an inlet (312), an outlet (314), and further defines a cavity (316). Disposed within the cavity (316) are a fluid diffuser (320), a plurality of substrates (330), a collector (340), and a holder (350). In some embodiments, the holder (350) may be configured to releasably engage (e.g., hold) one or more of the fluid diffuser (320), plurality of substrates (330), and collector (340). The holder (350) may be coupled to an inner wall of the enclosure (310) via one or more supports (352). In some embodiments, the holder (350) may be integrated into the inner wall of the enclosure (310). The fluid diffuser (320) may be disposed between the inlet (312) and the plurality of substrates (330), and the collector (340) may be disposed between the plurality of substrates (330) and the outlet (314). Any of the fluid diffuser (320), substrates (330), and collector (340) may be removable or fixed to the enclosure (310). In some embodiments, fluid (e.g., growth media) may be configured to flow in a direction from the inlet (312) to the outlet (314). In some embodiments, fluid (e.g., growth media) may be configured to flow in a direction from the outlet (314) to the inlet (312). In some embodiments, fluid flow may be configured to change direction through the inlet (312) and outlet (314) during use.

Figure 3B:
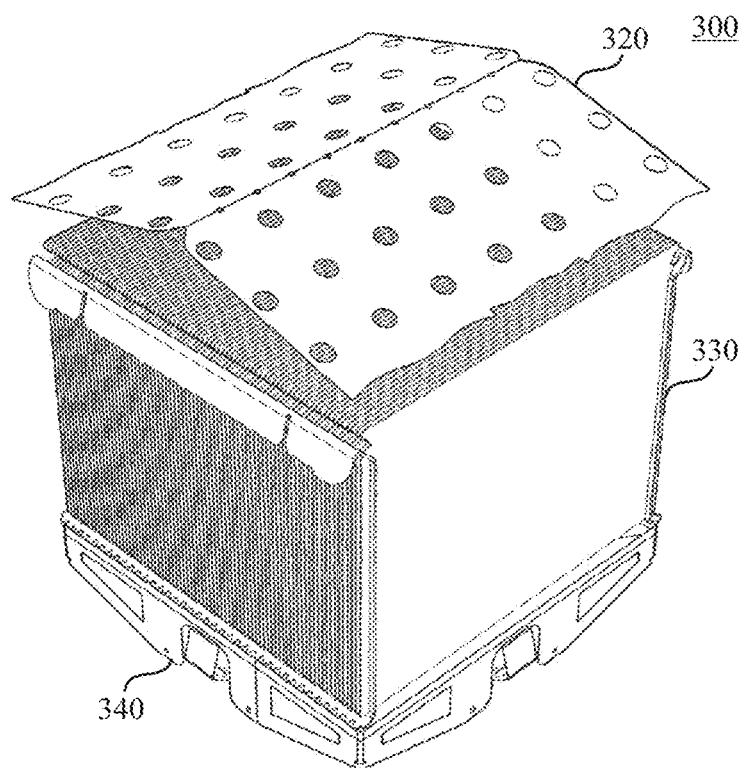
FIG. 3B is an illustrative perspective view of a set of internal components of the apparatus shown in FIG. 3A.
Figure 3C:
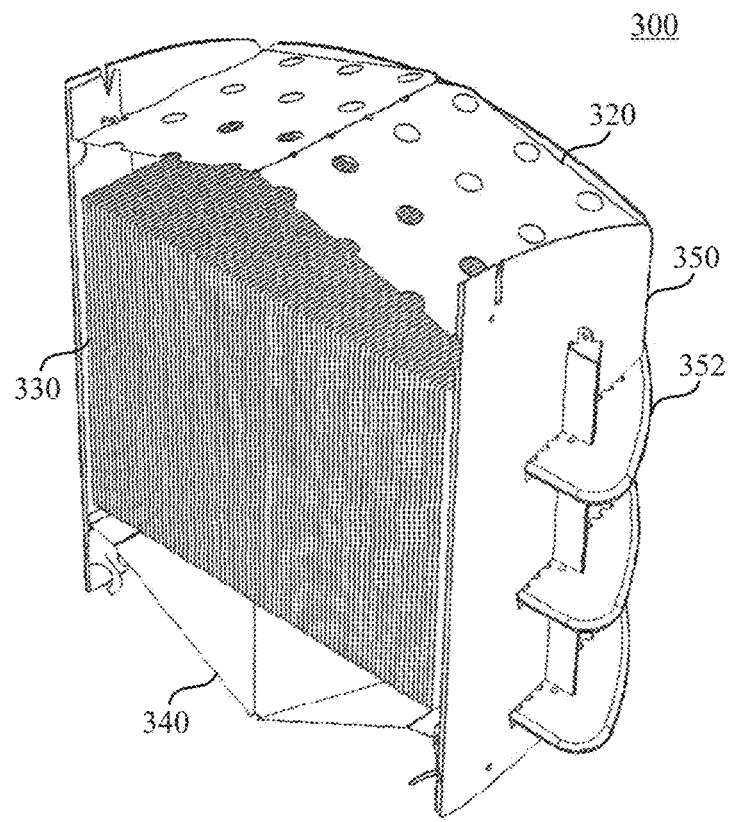
FIG. 3C is an illustrative cross-sectional perspective view of the internal components of the apparatus shown in FIG. 3B.
Figure 3D:
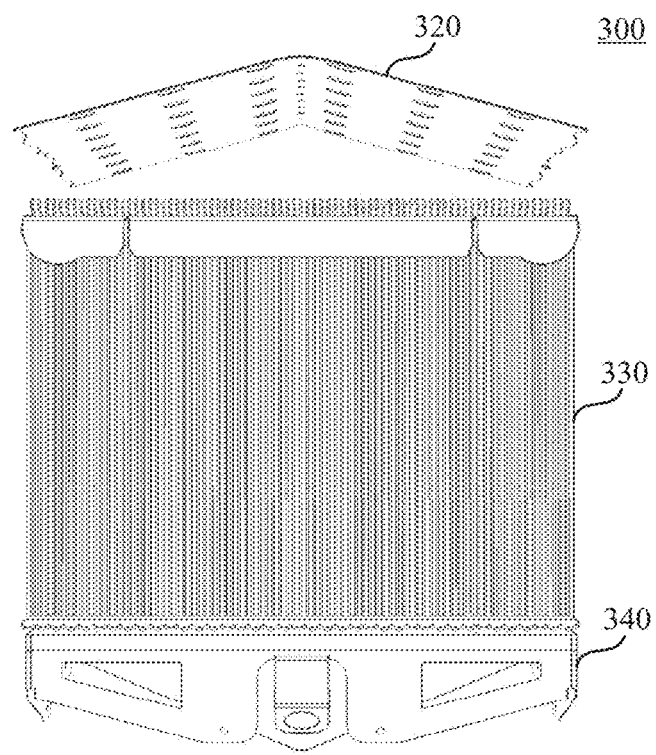
FIG. 3D is an illustrative side view of the internal components of the apparatus shown in FIG. 3B.

FIG. 3B is a perspective view of a set of internal components of the apparatus (300) with the enclosure (310) and holder (350) removed. FIG. 3C is a cross-sectional perspective view of the internal components of the apparatus (300). FIG. 3D is a side view of the internal components of the apparatus (300). The fluid diffuser (320) may be configured to distribute received fluid flow across each substrate of the plurality of substrates (330). The fluid diffuser (320) may be coupled to a proximal end of the plurality of substrates (330). In some embodiments, the fluid diffuser (320) may be configured to releasably engage to the enclosure and may be at least partially disposed in the cavity (316). For example, the fluid diffuser (320) may be slidably and releasably engaged to the holder (350) without any tools or fasteners, thereby aiding maintenance and sterilization of the apparatus (300). The collector (340) may be configured to receive a meat product and fluid from each substrate of the plurality of substrates (330). In some embodiments, the collector (340) is coupled to a distal end of the plurality of substrates (330). Additionally or alternatively, a collector may be disposed externally of the enclosure (310). For example, a collector may receive an output of the outlet (314).

In some embodiments, the plurality of substrates (330) may be configured to releasably engage to the enclosure (330). For example, the plurality of substrates (330) may be slidably and releasably engaged to the holder (350) without any tools or fasteners, thereby aiding maintenance and sterilization of the plurality of substrates (330). In some embodiments, the plurality of substrates (330) may be disposed in a vertical orientation relative to a ground surface such that fluid may be configured to flow downward in the spaces between the substrates.

Figure 4A:
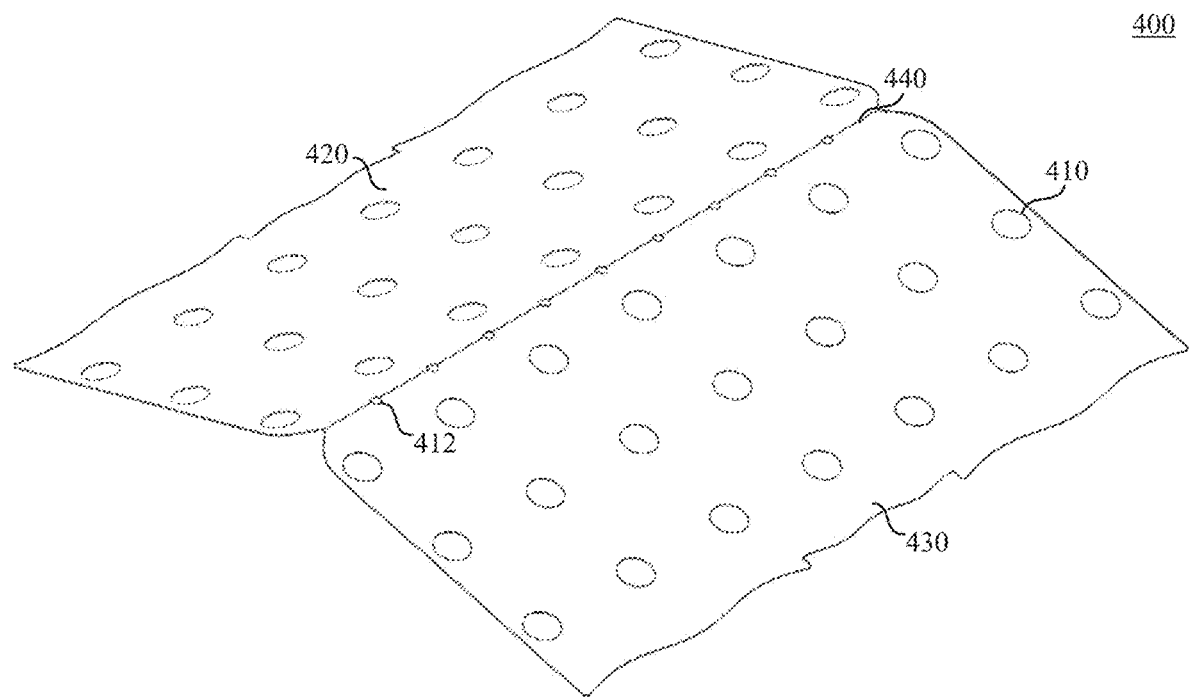
FIG. 4A is an illustrative perspective view of an exemplary embodiment of a fluid diffuser.

In some embodiments, a fluid diffuser may be configured to regulate a fluid flow rate over one or more substrates of an apparatus. For example, a fluid diffuser may be configured to receive a fluid and output a substantially uniform and laminar flow to each substrate of the plurality of substrates. FIG. 4A is a perspective view of a fluid diffuser (400) comprising a first portion (420) and a second portion (430). The fluid diffuser may comprise a plurality of openings (410). The fluid diffuser (400) may comprise an interface (440) of the first portion (420) and the second portion (430). The first portion (420) and the second portion (430) may bend relative to each other at the interface (440). In some of these embodiments, the interface (440) may comprise one or more of the plurality of openings (412). The interface (440) may be linear or non-linear.

The first portion (420) may be angled relative to the second portion (430) between about 90 degrees and about 170 degrees, including all values and sub-ranges in-between. For example, FIG. 4D is a side view of the fluid diffuser (400) where the first portion (420) may be angled relative to the second portion (430) by about 150 degrees. A larger angle between the first portion (420) and the second portion (430) allows the fluid diffuser (400) to have a smaller height, and thus may reduce a volume of empty space between an inlet and a plurality of substrates.

The first portion (420) and the second portion (430) may be angled relative to the plurality of substrates by up to about 80 degrees. In some embodiments, the plurality of openings comprise an area of at least about 700 µm². For example, each opening may comprise a diameter of about 30 µm, thus allowing the passage of growth media through the fluid diffuser (400).

Figure 4B:
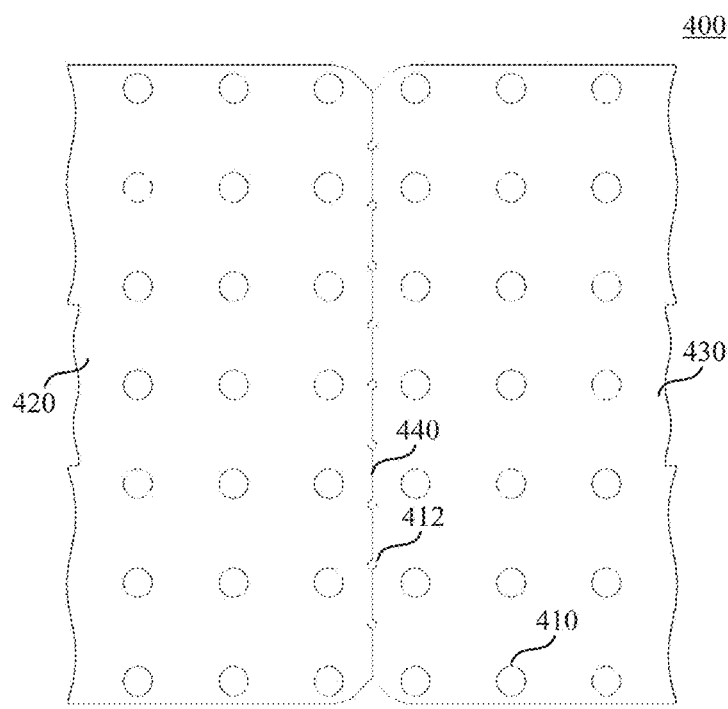
FIG. 4B is an illustrative plan view of the fluid diffuser shown in FIG. 4A.
Figure 4C:
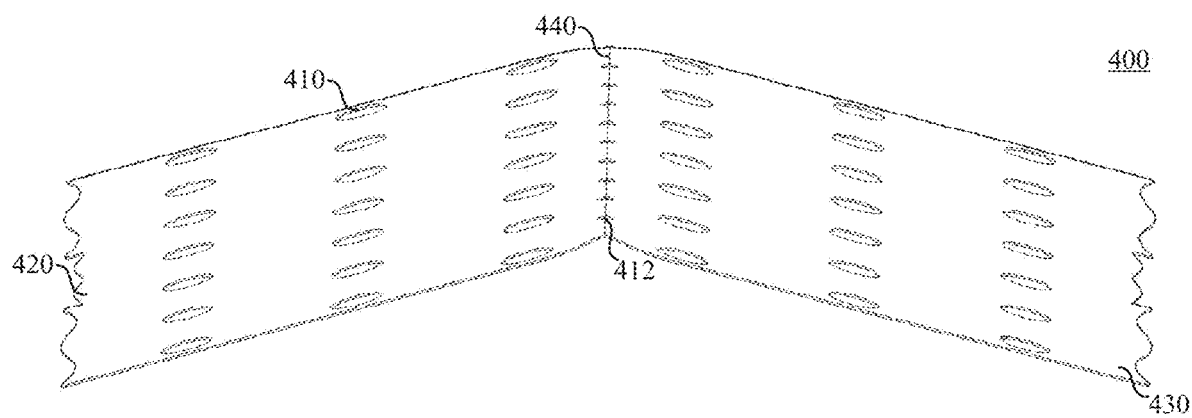
FIG. 4C is another illustrative perspective view of the fluid diffuser shown in FIG. 4A.
Figure 4D:
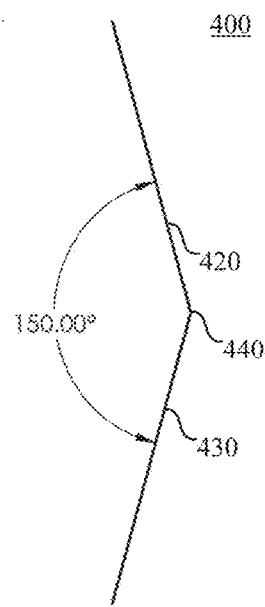
FIG. 4D is an illustrative side view of the fluid diffuser shown in FIG. 4A.

FIG. 4B is a plan view of the fluid diffuser (400). In some embodiments, the plurality of openings are substantially equally spaced apart. In some embodiments, each opening (410, 412) of the plurality of openings comprise a diameter of at least about 30 µm. For example, the diameter of an opening (410, 412) may be between about 30 µm and about 10 cm, and between about 0.5 cm and about 3 cm, including all values and sub-ranges in-between. FIG. 4C is another perspective view of the fluid diffuser (400). As shown in FIG. 4D, the first portion (420) and the second portion (430) are substantially flat with minimal thickness. The configuration of the fluid diffuser (400) may reduce material build-up, fouling due to clogging, and aid sterilization while configured to output a substantially uniform and laminar flow to a plurality of substrates. The shape of the openings (410, 412) is circular in FIGS. 4A-4D, but may be any shape.

Figure 5A:
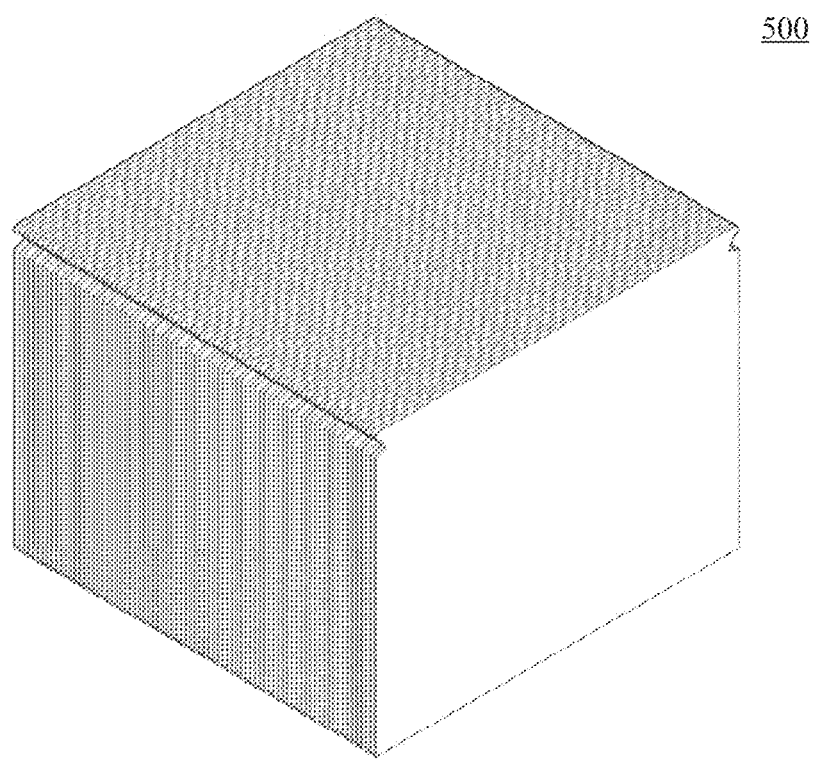
FIG. 5A is an illustrative perspective view of an exemplary embodiment of a plurality of substrates.
Figure 5B:
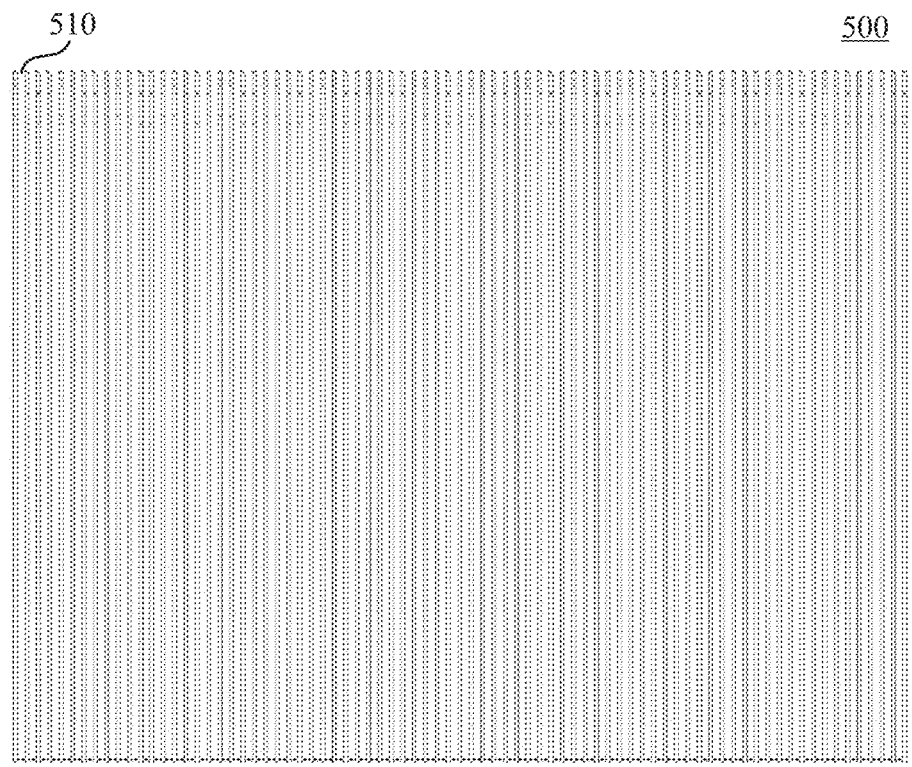
FIG. 5B is an illustrative side view of the substrates shown in FIG. 5A.

The amount of meat product prepared by the apparatuses described herein corresponds to the number and surface area of the substrates of an apparatus. For example, a plurality of parallel substrates may be configured to generate a commercial-scale quantity of edible meat product. FIGS. 5A and 5B are respective perspective and side views of a plurality of substrates (500). In some embodiments, an apparatus for preparing a meat product comprises one or more substrates (500) configured to culture one or more cells on a surface thereon to form a meat product. In some embodiments, one or more of the substrates (500) are removable from the apparatus such that they may be cleaned or maintained and re-used. As shown in FIG. 5A, the plurality of substrates (500) are planar and are substantially parallel to each other. In some embodiments, the apparatus comprises a single substrate or a plurality of substantially parallel substrates (e.g., parallel plate configuration). A parallel plate configuration allows for increased surface area for adherent tissue sheets. In some embodiments, the parallel plates are aligned in the direction of the fluid flow. For example, the plates and corresponding fluid channels are oriented perpendicular to a ground surface.

In some embodiments, the apparatus may comprise a plurality of fluid channels (510). For example, the plurality of substrates (500) may define the plurality of fluid channels (510). Each fluid channel (510) may be associated with at least one of the plurality of substrates (500) in that a fluid channel (510) comprises the space between adjacent substrates (500). Where the plurality of substrates (500) are planar, the fluid channel (510) may be planar. With respect to FIG. 5B, fluid may be configured to flow in one direction through the plurality of fluid channels (510). For example, a plurality of planar substrates may be separated by a predetermined gap (e.g., vertical gap where the substrate is perpendicular to ground) through which fluid may be perfused such that the meat product may be grown on the plurality of substrates. In some embodiments, the plurality of fluid channels are substantially parallel to each other. In some embodiments, each fluid channel may have a width between about 0.3 mm and about 5.0 cm, including all values and sub-ranges in-between.

A plurality of substrates (500) may allow for high-density growth of meat products. For example, the substrates (500) are configured to grow the meat product on opposite sides of the substrate. In some embodiments, each substrate (500) comprises dimensions including a width between about 10 cm and about 400 cm, and a length between about 10 cm and about 200 cm. In some embodiments, a plurality of substrates (500) may include up to about 10,000,000 substrates, including all values and sub-ranges in-between.

In some embodiments where the substrate comprises a spiral (e.g., coiled) shape, the substrate may comprise a thickness between about 0.1 mm and about 10 mm, a length between about 10 cm and about 300 cm, a width between about 10 cm and about 200 m, and a spacing between adjacent spirals between about 1 mm and about 10 mm, including all values and sub-ranges in-between. For example, the spiral substrate may comprise a thickness of about 2 mm, a width of about 128 m, and a spacing between adjacent spirals of about 3 mm. In some embodiments, a spacing between adjacent (e.g., proximate) substrates may be between about 0.3 mm and about 5.0 cm, including all values and sub-ranges in-between. In some embodiments, each substrate comprises an area between about 430 cm² and about 100,000,000 cm², including all values and sub-ranges in-between.

Figure 9A:
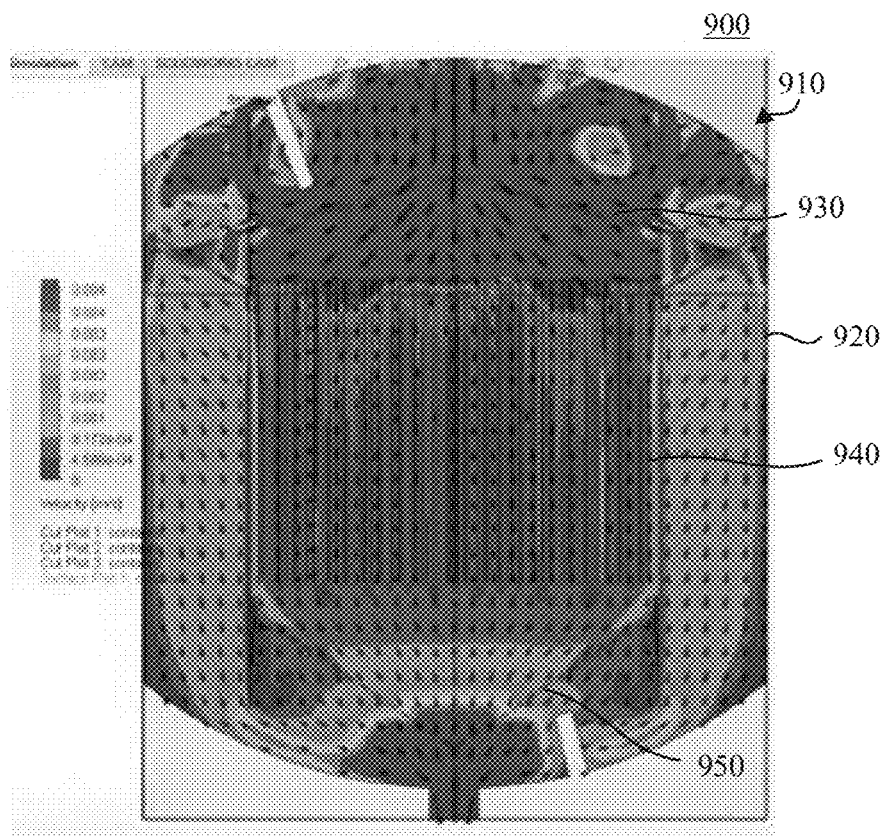
FIGS. 9A and 9B are illustrative cross-sectional side views of fluid flow through an exemplary embodiment of an apparatus for preparing a meat product.
Figure 9B:
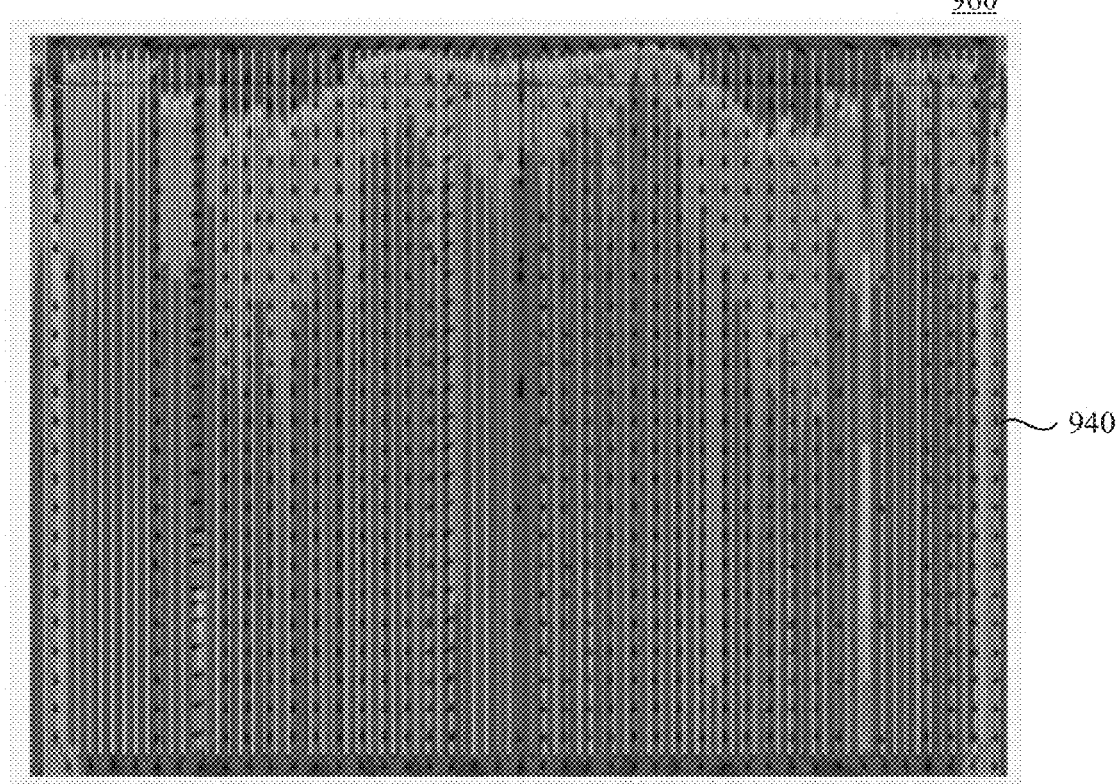

FIGS. 9A and 9B are cross-sectional side views of fluid flow vector diagram (900, 960) through an apparatus for preparing a meat product as described herein. FIG. 9A illustrates fluid flow velocity (900) for a cross-sectional image of an apparatus (910) comprising an enclosure (920), fluid diffuser (930), plurality of substrates (940), and collector (950). Fluid enters into the apparatus (910) from a top of the enclosure (920) at a relatively high velocity in a non-uniform and non-laminar manner. The fluid diffuser (930) receives the fluid and diffuses (e.g., regulates, conditions) the flow such that the plurality of substrates (940) receive a substantially uniform and laminar fluid flow, thereby allowing consistent cell growth across each of the plurality of substrates. FIG. 9B is a detailed cross-sectional image of fluid flow velocity (960) of the plurality of substrates depicting substantially uniform and laminar fluid flow therethrough. Fluid flow is generally regular and symmetrically dispersed across the plurality of substrates (940). The fluid passes through the fluid channels between adjacent substrates to the collector (950) and an outlet of the enclosure (920). The collector (950) may be configured to maintain a flow rate sufficient to reduce back pressure in the apparatus (910). For example, the collector (950) may be configured to maintain a flow rate sufficient to prevent fluid from backing up into the plurality of substrates.

Figure 6A:
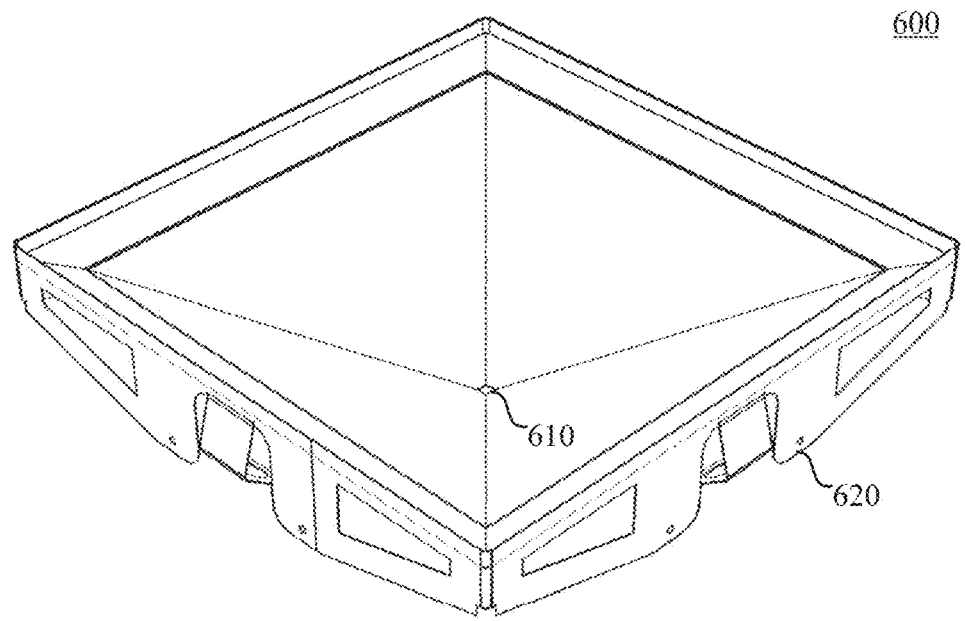
FIG. 6A is an illustrative perspective view of an exemplary embodiment of a collector.
Figure 6B:
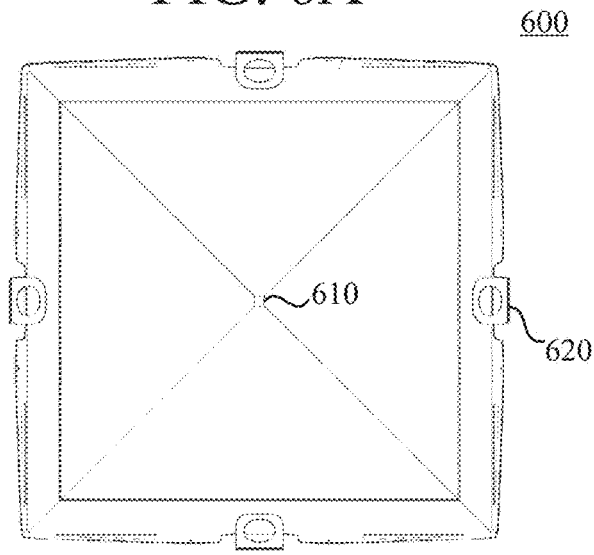
FIG. 6B is an illustrative plan view of the collector shown in FIG. 6A.
Figure 6C:
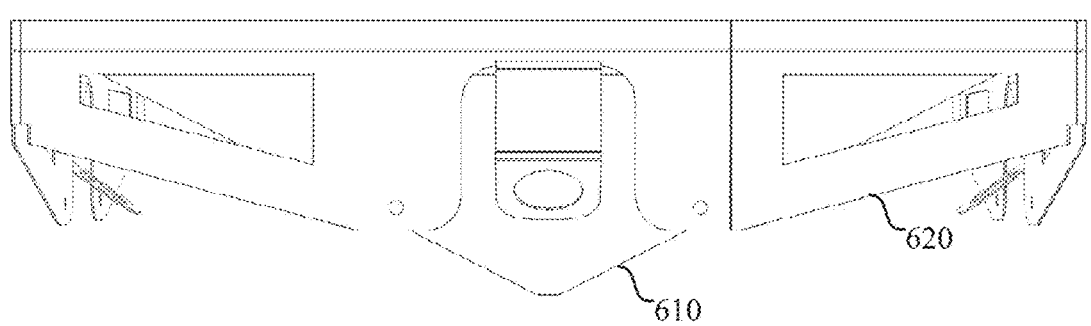
FIG. 6C is an illustrative side view of the collector shown in FIG. 6A.

FIGS. 6A-6C are illustrative views of an exemplary embodiment of a collector (600) comprising one or more openings (610) and connector (620) configured to releasably engage the collector (600) to the apparatus. In some embodiments, the collector (600) may be configured to receive fluid and the meat product (e.g., one or more cell sheets) from one or more substrates. The fluid may pass through the collector (600) and out of the apparatus through an outlet while the meat product may be held in the collector (600) until retrieval. For example, the collector (600) may be configured to receive the meat product grown on a substrate after the meat product is separated from the substrate using fluid flow. In some embodiments, the meat product may fall by gravity into the collector (600). For example, the collector (600) may be disposed beneath one or more substrates such that the collector (600) catches and holds the falling meat product.

In some embodiments, the collector (600) may be disposed in a cavity of an apparatus. Additionally or alternatively, a collector may be coupled externally to the apparatus. In some embodiments, the collector (600) may comprise one or more openings comprising an area of at least about 700 µm². For example, each opening may comprise a diameter of between about 30 µm and about 2.5 cm, including all values and sub-ranges in-between. In some embodiments, the collector (600) may be a separate component from, or integrated with, the enclosure. In some embodiments, where the collector (600) is external to the enclosure, the collector may comprise one or more openings comprising an area of at least about 20 µm²

Figure 7A:
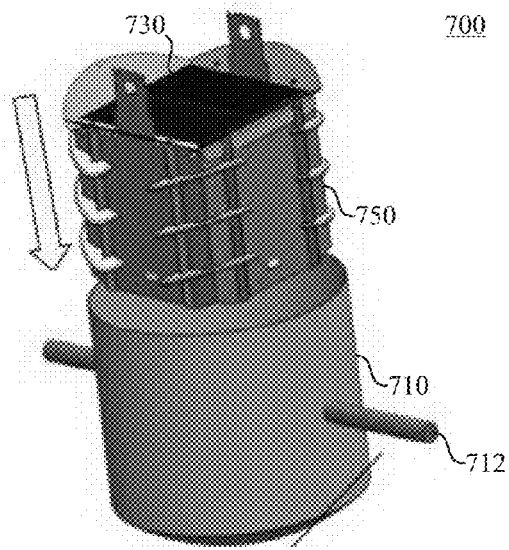
FIGS. 7A, 7B, 7C, and 7D are illustrative perspective views of an exemplary embodiment of an assembly process for an apparatus for preparing a meat product.
Figure 7B:
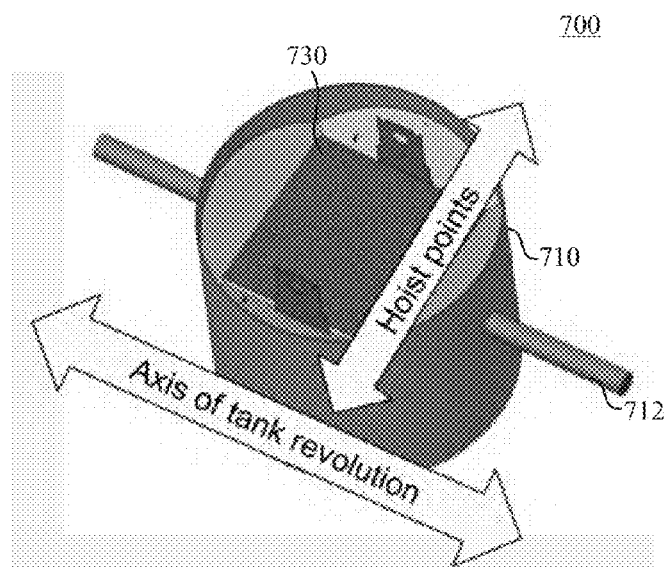
Figure 7C:
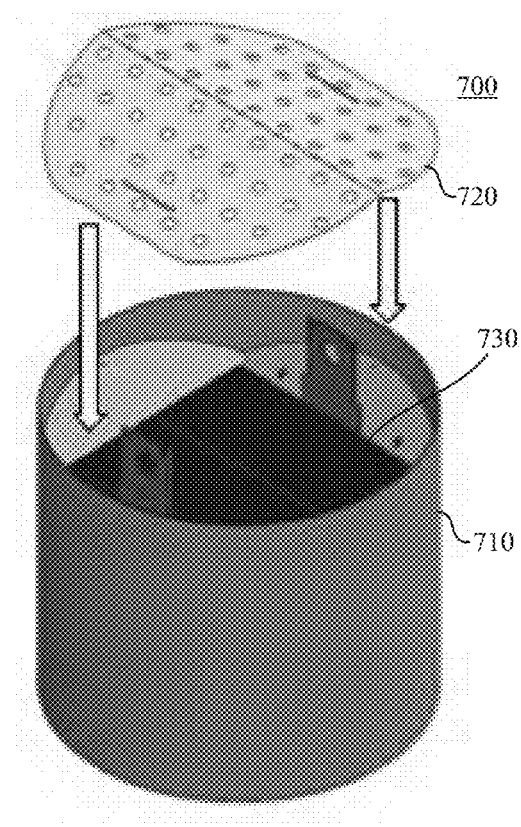
Figure 7D:
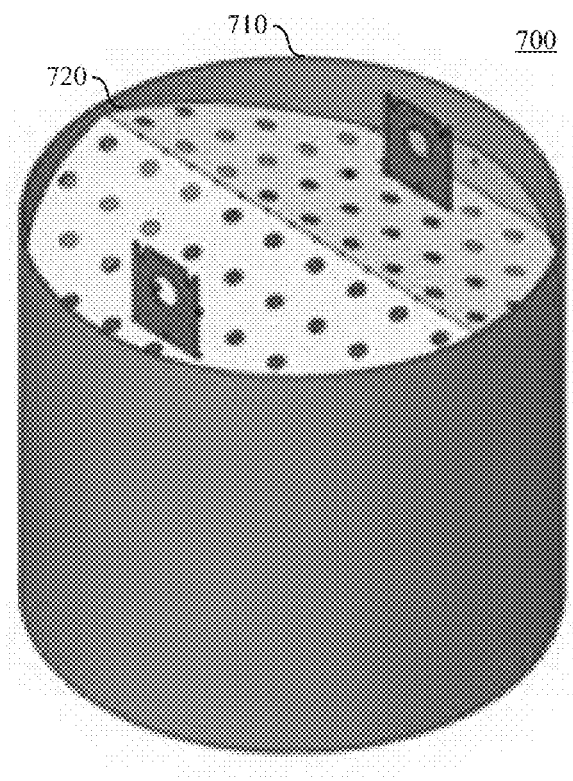

FIGS. 7A, 7B, 7C, and 7D are illustrative perspective views of an assembly process for an apparatus (700) for preparing a meat product. In some embodiments, a plurality of substrates (730) coupled to a holder (750) may be inserted into an enclosure (710). A rotation axis (712) of the enclosure (710) is depicted in FIGS. 7A and 7B. The enclosure (710) may be rotated about the rotation axis (712) to aid seeding of the plurality of substrates (730) as described in more detail herein. FIG. 7B depicts the plurality of substrates (730) disposed within a cavity of the enclosure (710). FIG. 7C depicts a fluid diffuser (720) being inserted into the cavity (710) above the plurality of substrates (730). The enclosure (710) may further comprise a lid (not shown) configured to seal an open end of the enclosure (710) to promote a sterile environment within the apparatus (700). Once the apparatus (700) is assembled, a plurality of cells may be applied to the plurality of substrates (730).

Figures 8A, 8B, 8C:
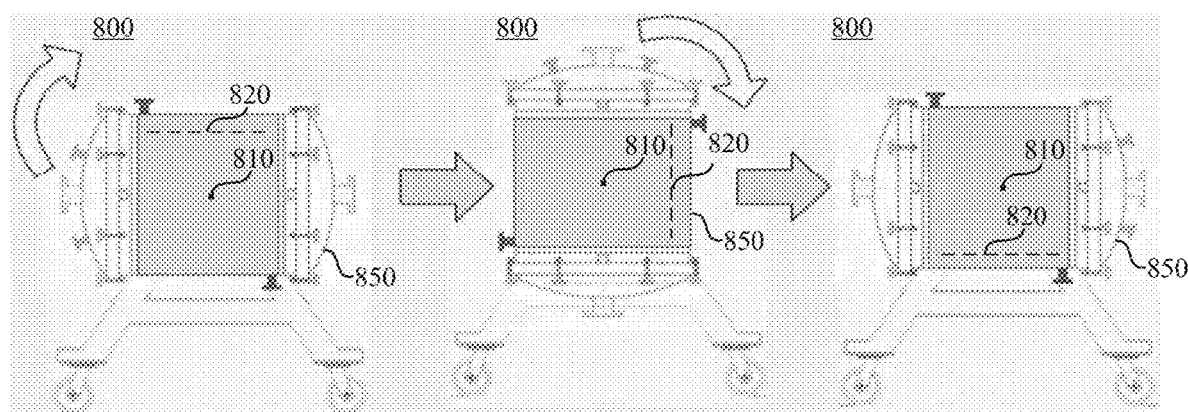
FIGS. 8A, 8B, and 8C are illustrative side views of an exemplary embodiment of a rotation process for an apparatus for preparing a meat product.

In some variations, a rotator (e.g., rotation mechanism) coupled to the enclosure may be configured to rotate the apparatus to aid cell seeding. FIGS. 8A, 8B, and 8C are illustrative side views of an exemplary embodiment or a rotation process (800) for an apparatus (850) for preparing a meat product. The apparatus may be rotated about a rotation axis (810) having a rotator (not shown). A substrate (810) may be disposed lengthwise within the enclosure (850) along a length of the enclosure (850). The substrate (810) within the enclosure (850) may be rotated about the rotation axis (810) as the apparatus (850) may be rotated. As shown in FIGS. 8A and 8C, rotation of the apparatus (850) about the rotation axis (810) allows for either side of the substrate (820) to be held upwards, allowing for cell settling by gravity. The apparatus (850) may be rotated upright as shown in FIG. 8B to orient the substrate (820) perpendicularly to a ground surface and allow fluid to flow from top to bottom of the apparatus (850).

Figure 10A:
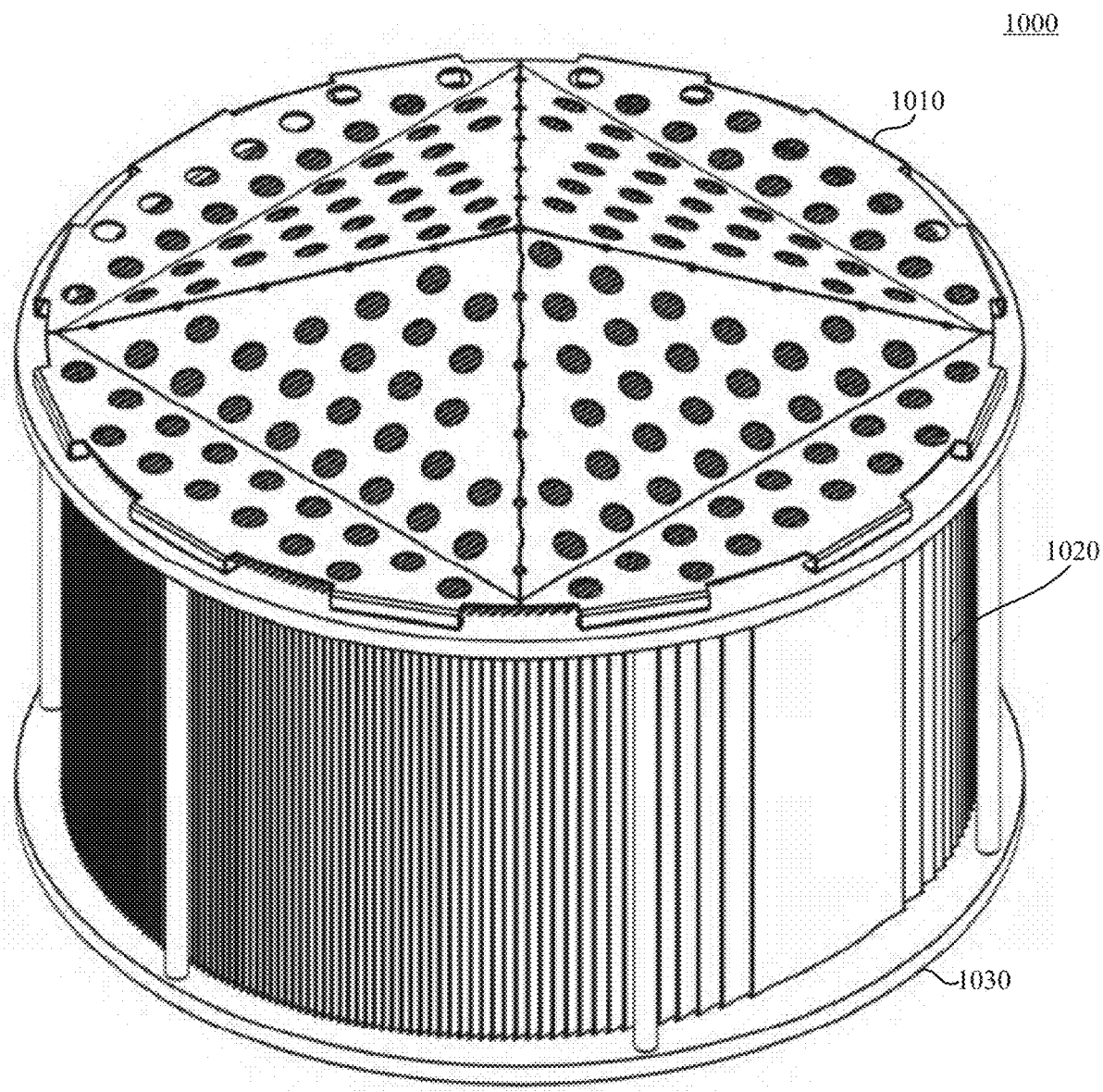
FIG. 10A is an illustrative perspective view of an exemplary embodiment of an apparatus for preparing a meat product.
Figure 10B:
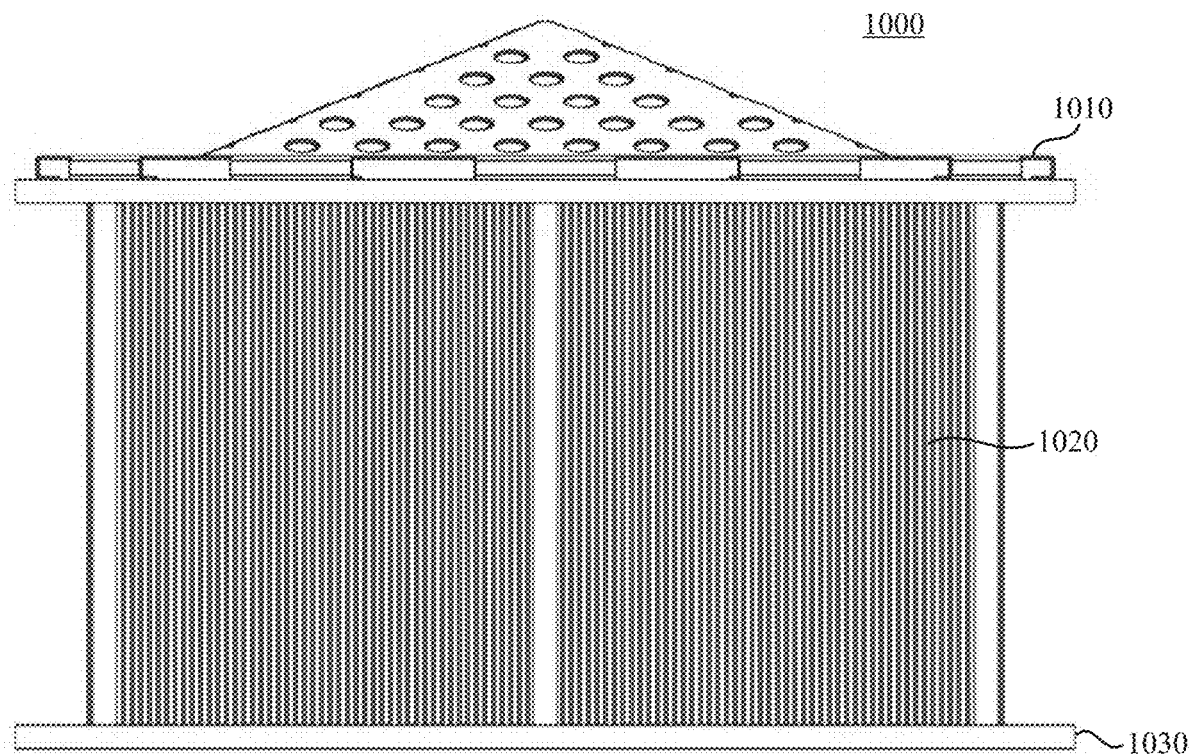
FIG. 10B is an illustrative front view of the apparatus shown in FIG. 10A.
Figure 10C:
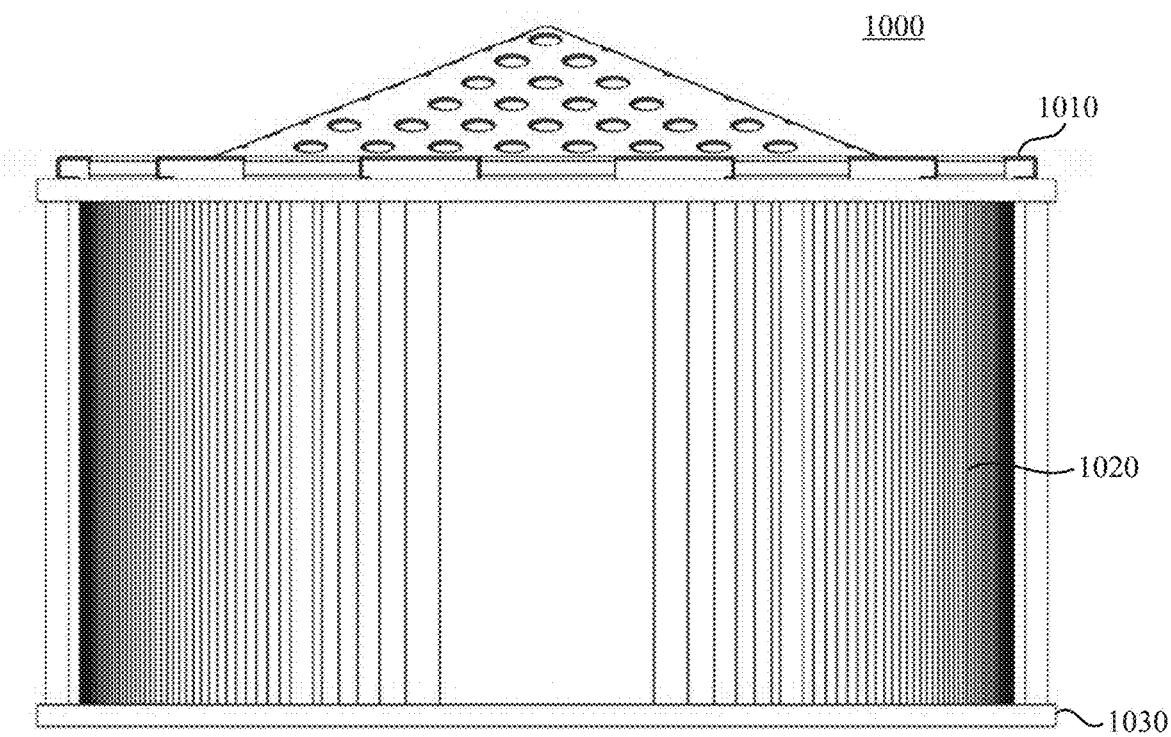
FIG. 10C is an illustrative side view of the internal components of the apparatus shown in FIG. 10B.

FIGS. 10A-12D describe a second exemplary embodiment of an apparatus for preparing a meat product. FIG. 10A is a perspective view of an embodiment of an apparatus (1000) for preparing a meat product without an enclosure (for the sake of clarity). FIG. 10B is a front view of the apparatus (1000) and FIG. 10C is a side view of the internal components of the apparatus (1000). The apparatus (1000) shown in FIG. 10A comprises a fluid diffuser (1010), a plurality of substrates (1020), and a holder (1030). In some embodiments, the holder (1030) may be configured to releasably engage (e.g., hold) one or more of the fluid diffuser (1010) and plurality of substrates (1020). In some embodiments, the holder (1030) may be integrated into an inner wall of an enclosure of the apparatus. The fluid diffuser (1010) may be disposed one a proximal side (e.g., top side) of the plurality of substrates (1020), and a collector (not shown) may be disposed on a distal side (e.g., bottom side) of the plurality of substrates (1020). Any of the fluid diffuser (1010), substrates (1020), and holder (1030) may be removable or fixed to the enclosure. In some embodiments, fluid (e.g., growth media) may be configured to flow in a direction from the fluid diffuser (1010) to the substrates (1020) (e.g., proximal to distal, top to bottom).

The fluid diffuser (1010) may be configured to distribute received fluid flow across each substrate of the plurality of substrates (1020). The fluid diffuser (1010) may be coupled to a proximal end of the plurality of substrates (1020). In some embodiments, the fluid diffuser (1010) may be slidably and releasably engaged to the holder (1030) without any tools or fasteners, thereby aiding maintenance and sterilization of the apparatus. A collector (not shown) may be configured to receive a meat product and fluid from each substrate of the plurality of substrates (1020). In some embodiments, the collector may be coupled to a distal end of the plurality of substrates (1020). Additionally or alternatively, a collector may be disposed externally of the apparatus (1000). For example, a collector may receive an output of an enclosure.

In some embodiments, the plurality of substrates (1010) are configured to releasably engage to the holder (1030). For example, the plurality of substrates (1020) may be slidably and releasably engaged to the holder (1030) without any tools or fasteners, thereby aiding maintenance and sterilization of the plurality of substrates (1020). In some embodiments, the plurality of substrates (1020) may be disposed in a substantially vertical orientation relative to a ground surface such that fluid may be configured to flow downward in the spaces between the substrates. In some embodiments, the plurality of substrates (1020) may be disposed in a substantially horizontal orientation relative to a ground surface during one or more steps of a method of preparing a meat product. For example, the meat product may be grown on the plurality of substrates (1020) for one or more days in the substantially horizontal orientation.

Figure 11A:
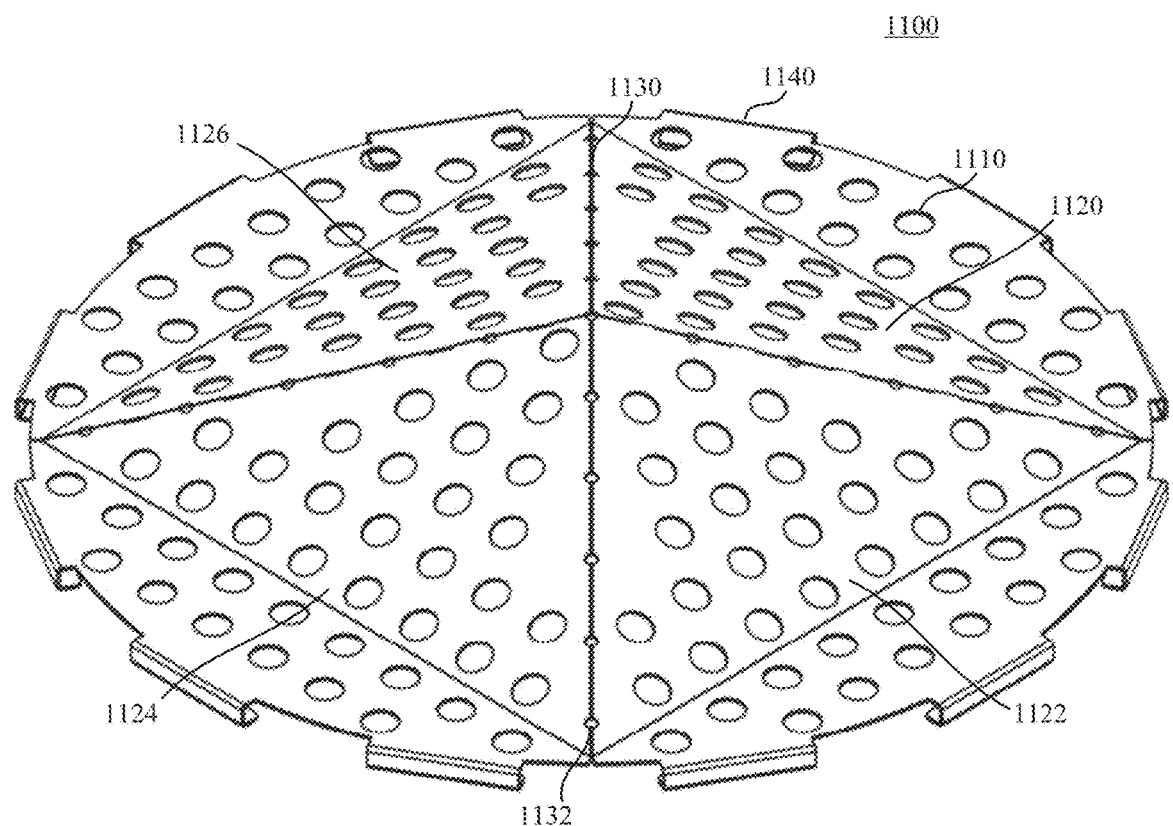
FIG. 11A is an illustrative perspective view of an exemplary embodiment of a fluid diffuser.

FIG. 11A is a perspective view of a fluid diffuser (1100) comprising a first portion (1120), second portion (1122), third portion (1124), and fourth portion (1126). The fluid diffuser (1100) may comprise a plurality of openings (1110). In some embodiments, the plurality of openings comprise an area of at least about 700 µm². For example, each opening may comprise a diameter of about 30 µm, thus allowing the passage of growth media through the fluid diffuser (1100). The fluid diffuser (1100) may comprise an interface (1130) between adjacent portions where the portions bend relative to each other. In some of these embodiments, the interface (1130) may comprise one or more of the plurality of openings (1132). The interfaces (1130) may be linear or non-linear. In some embodiments, the fluid diffuser (1100) may further comprise a connector (1140).

Figure 11B:
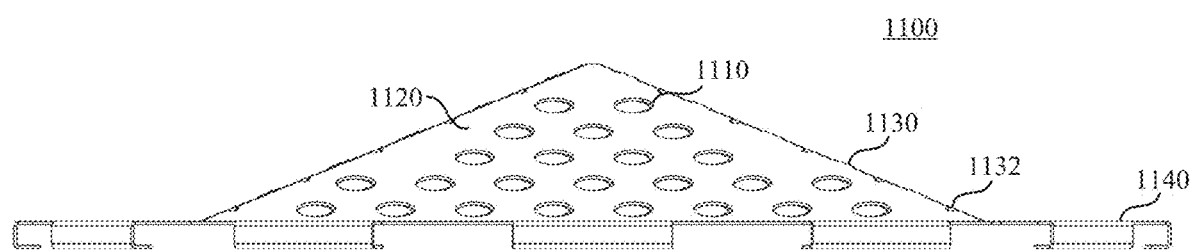
FIG. 11B is an illustrative side view of the fluid diffuser shown in FIG. 11A.

FIG. 11B is a side view of the fluid diffuser (1100). Opposing portions may be angled relative to each other between about 90 degrees and about 170 degrees, including all values and sub-ranges in-between. For example, the first portion (1120) may be angled relative to the third portion (1124) by about 150 degrees, and the second portion (1122) may be angled relative to the fourth portion (1126). A larger angle between the portions allow the fluid diffuser (1100) to have a smaller height, and thus may reduce a volume of empty space between an inlet and a plurality of substrates.

Each of the portions of the fluid diffuser (1100) may be angled relative to the plurality of substrates by up to about 80 degrees.

Figure 11C:
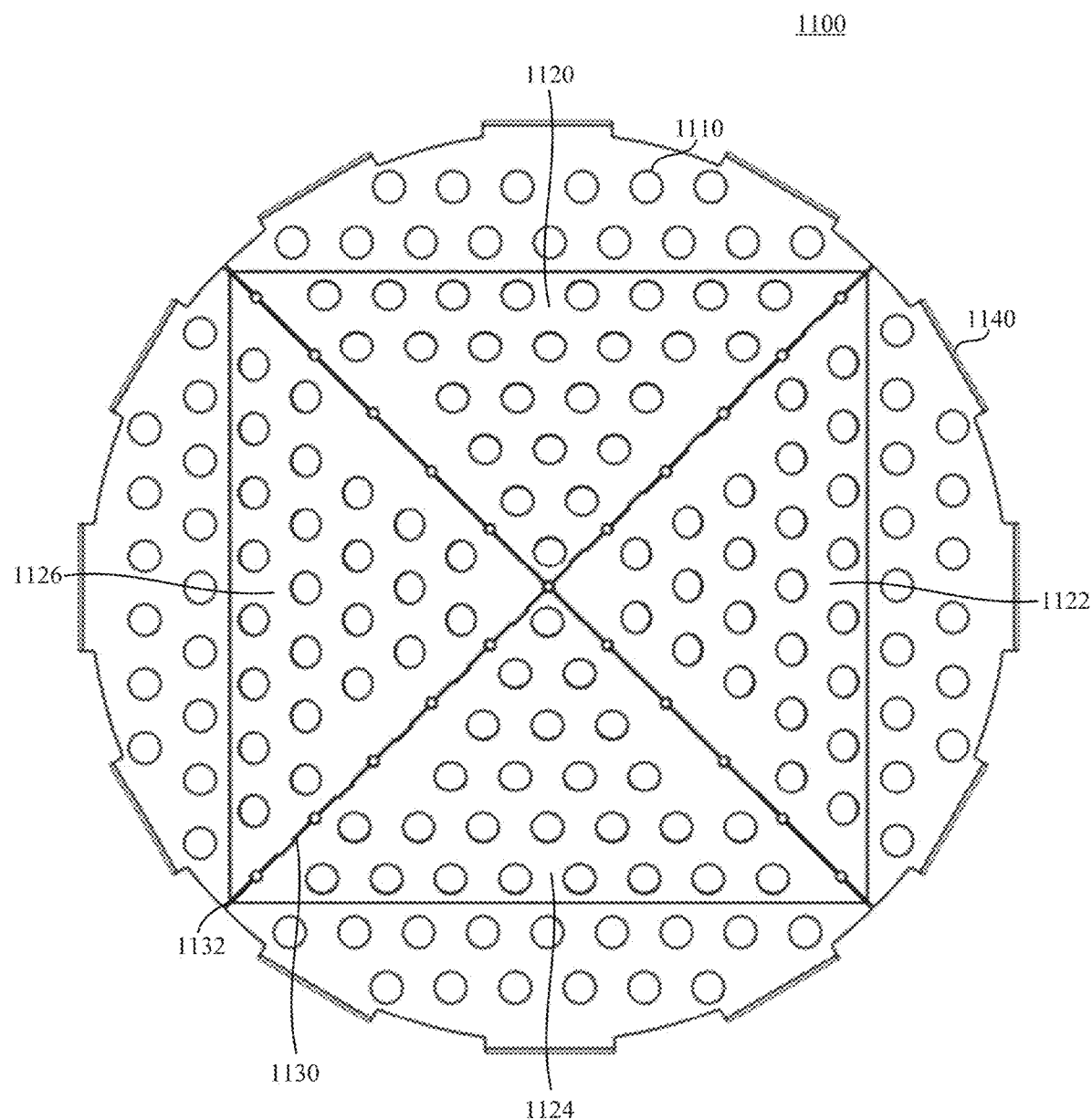
FIG. 11C is an illustrative plan view of the fluid diffuser shown in FIG. 11A.

FIG. 11C is a plan view of the fluid diffuser (1100). In some embodiments, the plurality of openings are substantially equally spaced apart. In some embodiments, each opening (1110, 1132) of the plurality of openings comprise a diameter of at least about 30 μm. For example, the diameter of an opening (1110, 1132) may be between about 30 μm and about 10 cm, and between about 0.5 cm and about 3 cm, including all values and sub-ranges in-between. The configuration of the fluid diffuser (1100) may reduce material build-up, fouling due to clogging, and aid sterilization while configured to output a substantially uniform and laminar flow to a plurality of substrates. The shape of the openings (1110, 1132) is circular in FIGS. 11A-11C, but may be any shape.

Figure 12A:
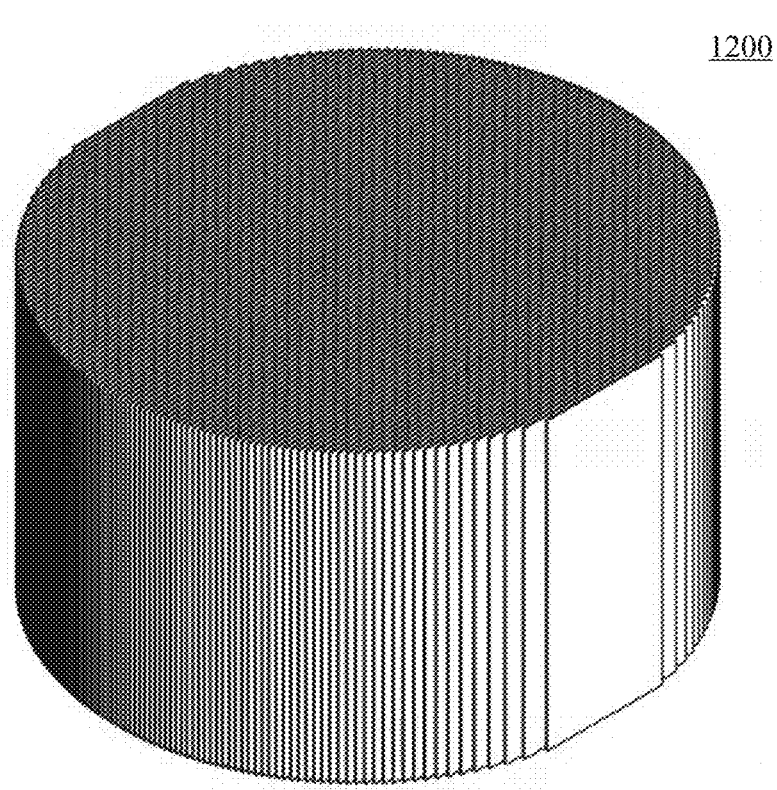
FIG. 12A is an illustrative perspective view of an exemplary embodiment of a plurality of substrates.
Figure 12B:
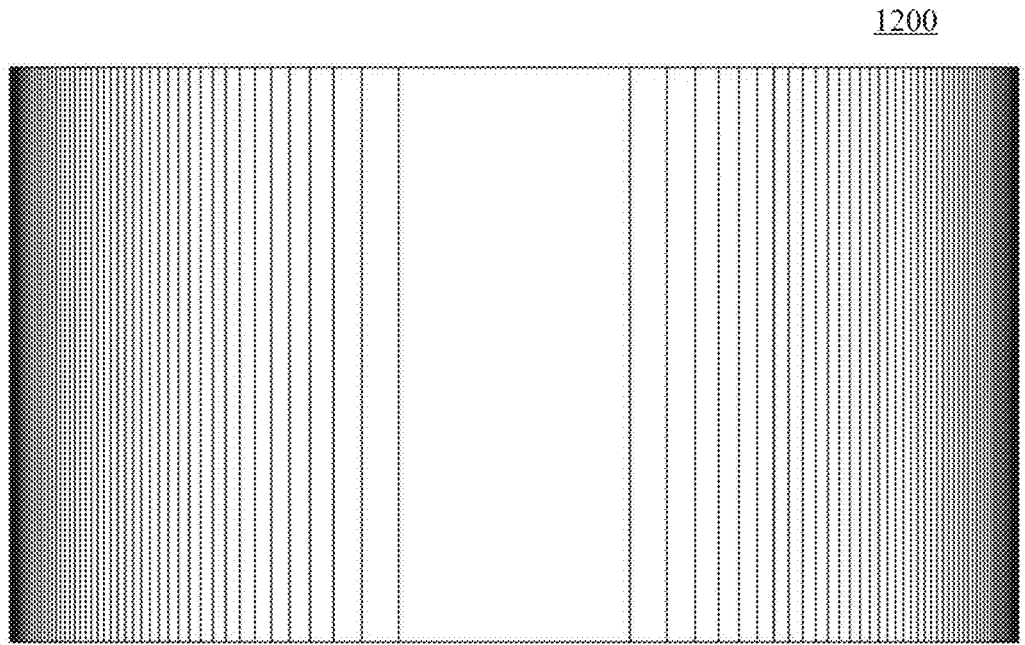
FIG. 12B is an illustrative side view of the substrates shown in FIG. 12A.
Figure 12C:
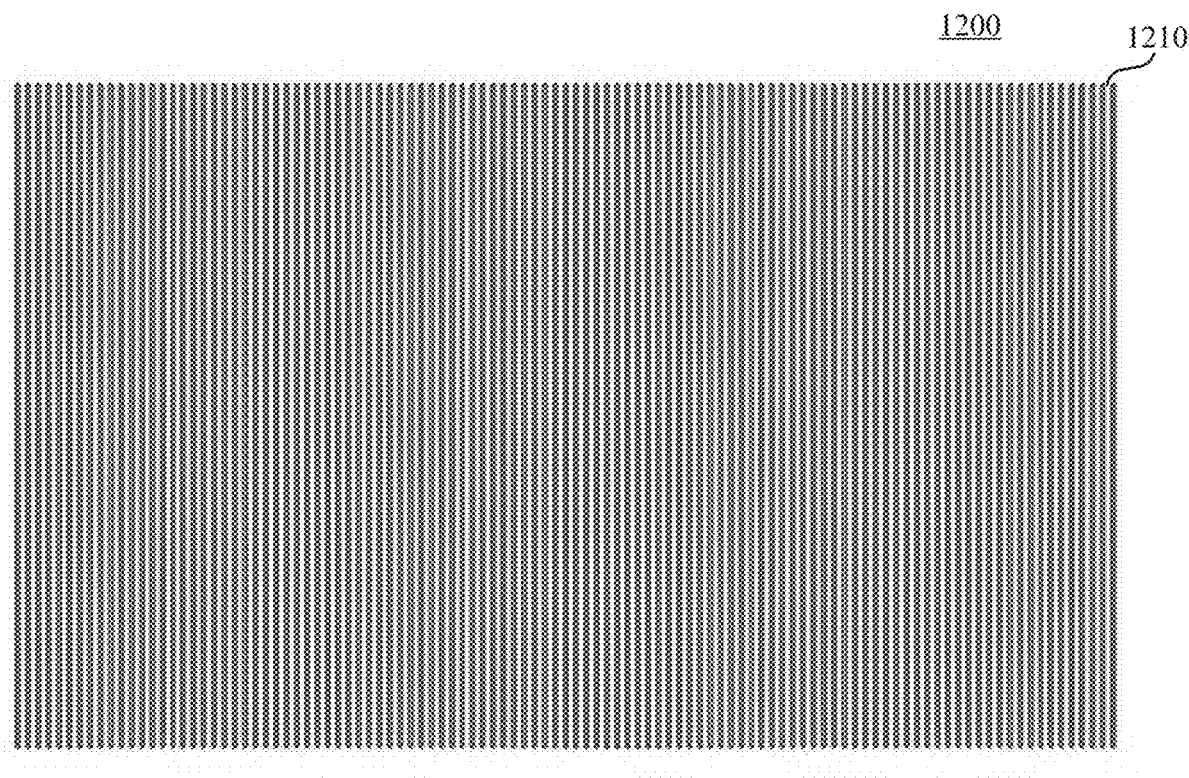
FIG. 12C is an illustrative front view of the substrates shown in FIG. 12A.
Figure 12D:
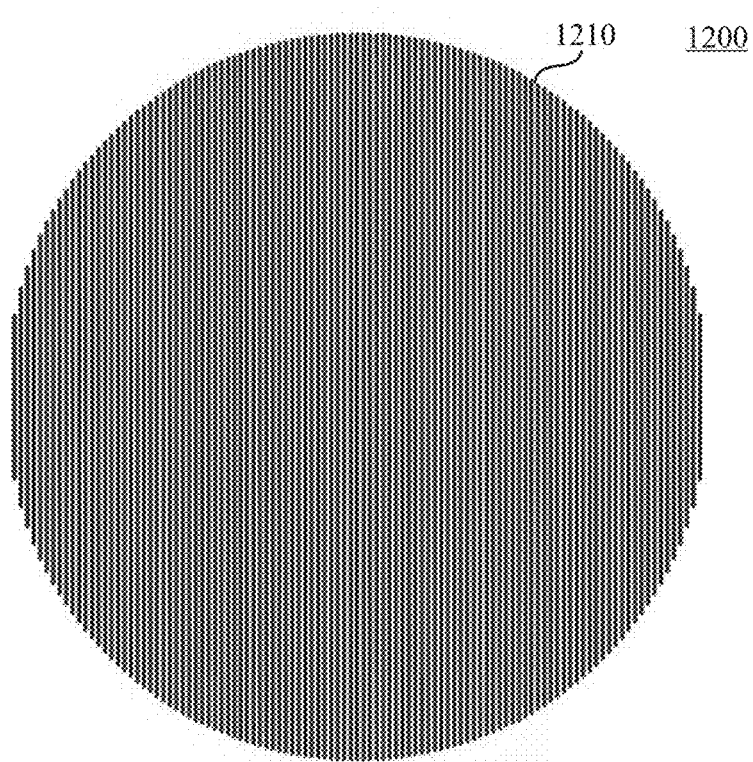
FIG. 12D is an illustrative plan view of the substrates shown in FIG. 12A.

FIG. 12A is a perspective view of a plurality of substrates (1200). FIG. 12B is a side view of the substrates (1200). The plurality of substrates (1200) may, as a whole, form a generally cylindrical shape that fits within a corresponding generally cylindrical enclosure (not shown). In some embodiments, each of the substrates may comprise substantially the same thickness and height as shown in FIG. 12C, while having different widths as shown in FIGS. 12A and 12B. In some embodiments, a plurality of fluid channels (1210) comprise a space between adjacent substrates (1200). For example, the fluid channels (1210) may comprise a width between about 0.3 mm and about 5.0 cm, including all values and sub-ranges in-between. The fluid channels (1210) are planar and conform to the planar surfaces of the substrates (1200).

In some embodiments, one or more of the substrates (1200) are removable from the apparatus such that they may be cleaned, maintained, and re-used. As shown in FIG. 12C, the plurality of substrates (1200) are planar and are substantially parallel to each other. In some embodiments, the apparatus comprises a single substrate or a plurality of substantially parallel substrates (e.g., parallel plate configuration). In some embodiments, the parallel plates are aligned in the direction of the fluid flow. For example, the plates and corresponding fluid channels are oriented perpendicular to a ground surface. A plurality of planar substrates may be separated by a predetermined gap (e.g., vertical gap where the substrate is perpendicular to ground) through which fluid may be perfused such that the meat product may be grown on the plurality of substrates. In some embodiments, the plurality of fluid channels are substantially parallel to each other. In some embodiments, each fluid channel may have a width between about 0.3 mm and about 5.0 cm.

A plurality of substrates (1200) may allow for high-density growth of meat products. For example, the substrates (1200) are configured to grow the meat product on opposite sides of the substrate. In some embodiments, each substrate (1200) comprises dimensions including a width between about 10 cm and about 400 cm, and a length between about 10 cm and about 200 cm, including all values and sub-ranges in-between. In some embodiments, a plurality of substrates (1200) may include up to about 1000 substrates, including all values and sub-ranges in-between. In some embodiments, a spacing between adjacent (e.g., proximate) substrates may be between about 0.3 mm and about 5.0 cm, including all values and sub-ranges in-between. In some embodiments, each substrate comprises an area up to about 140,000 $cm^2$, including all values and sub-ranges in-between. In some embodiments, each substrate comprises an area up to about 4,000 $cm^2$. In some embodiments, each substrate comprises an area between about 430 $cm^2$ and about 8,000 $cm^2$.

Figure 13A:
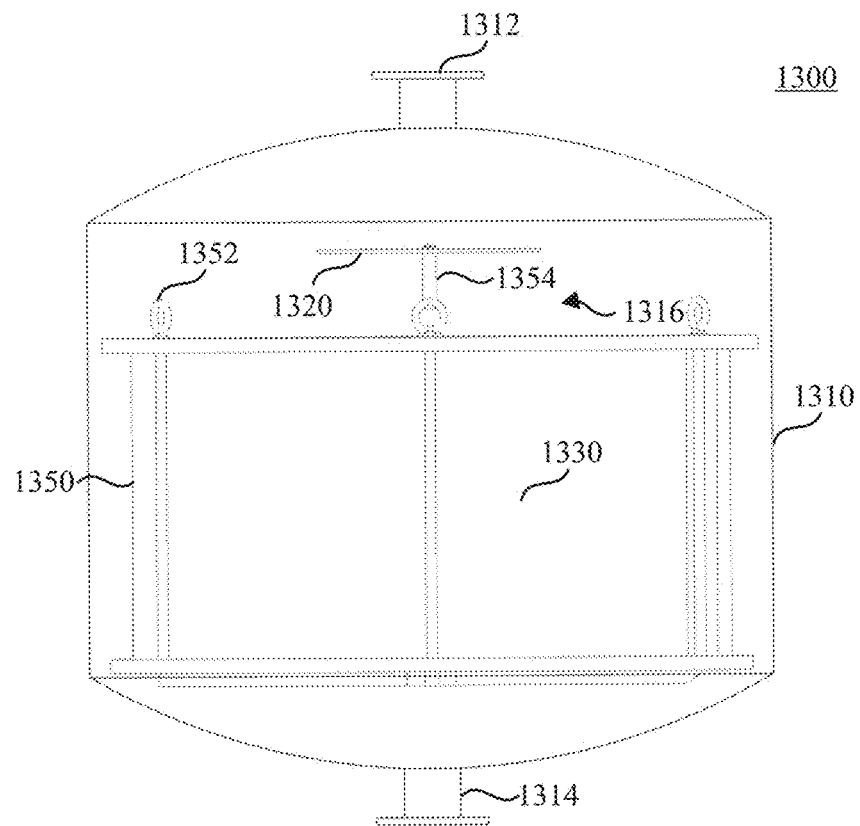
FIG. 13A is an illustrative cross-sectional side view of an exemplary embodiment of an apparatus for preparing a meat product.

FIGS. 13A-17C describe a third exemplary embodiment of an apparatus for preparing a meat product. FIG. 13A is a cross-sectional side view of an apparatus (1300) for preparing a meat product. The apparatus (1300) may comprise an enclosure (1310) comprising an inlet (1312), an outlet (1314), and further defines a cavity (1316). Disposed within the cavity (1316) may be a fluid diffuser (1320), at least one substrate (1330), and a holder (1350). In some embodiments, the holder (1350) may be configured to releasably engage (e.g., hold) one or more of the fluid diffuser (1320) and at least one substrate (1330). The holder (1350) may be coupled to an inner wall of the enclosure (1310). In some embodiments, the holder (1350) may be integrated into the inner wall of the enclosure (1310). The fluid diffuser (1320) may be disposed between the inlet (1312) and at least one substrate (1330). For example, the fluid diffuser (1320) may be disposed within a headspace (e.g., empty space above the substrate) of the enclosure (1310). Any of the fluid diffuser (1320) and substrate (1330) may be removable or fixed to the enclosure (1310). In some embodiments, fluid (e.g., liquid, growth media, gas) may be configured to flow in a direction from the inlet (1312) to the outlet (1314). For example, fluid may flow from a higher elevation (e.g., inlet (1312)) to a lower elevation (e.g., outlet (1314)). In some embodiments, fluid (e.g., growth media) may be configured to flow in a direction from the outlet (1314) to the inlet (1312). In some embodiments, fluid flow may be configured to change direction through the inlet (1312) and outlet (1314) during use. In some embodiments, an enclosure (1310) may comprise a plurality of inlets and outlets (e.g., growth media inlet, gas inlet, gas outlet).

Figure 13B:
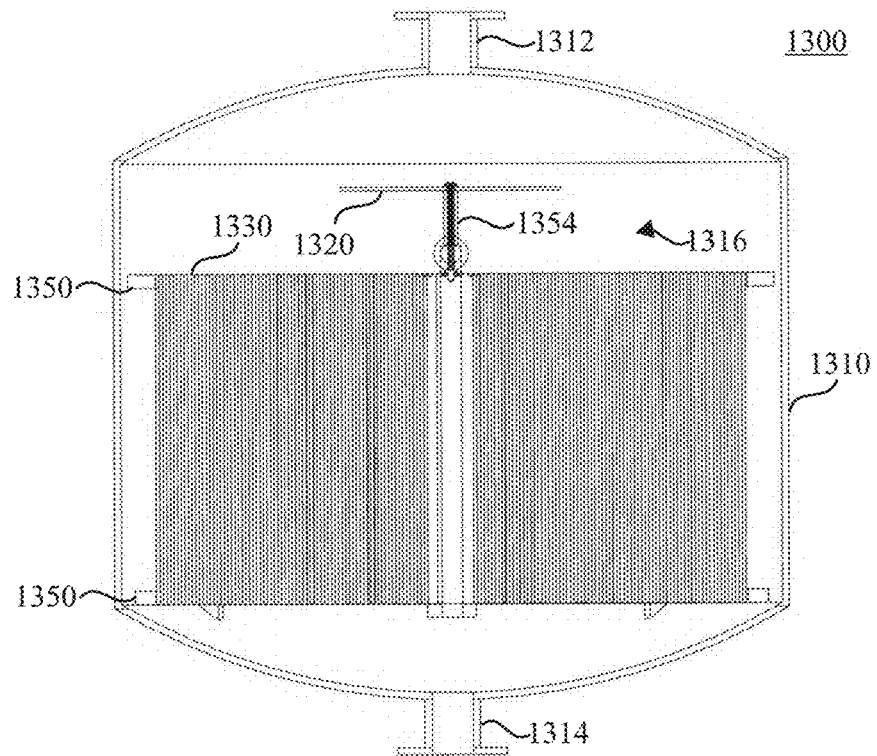
FIG. 13B is another illustrative side view of the apparatus shown in FIG. 13A.
Figure 13C:
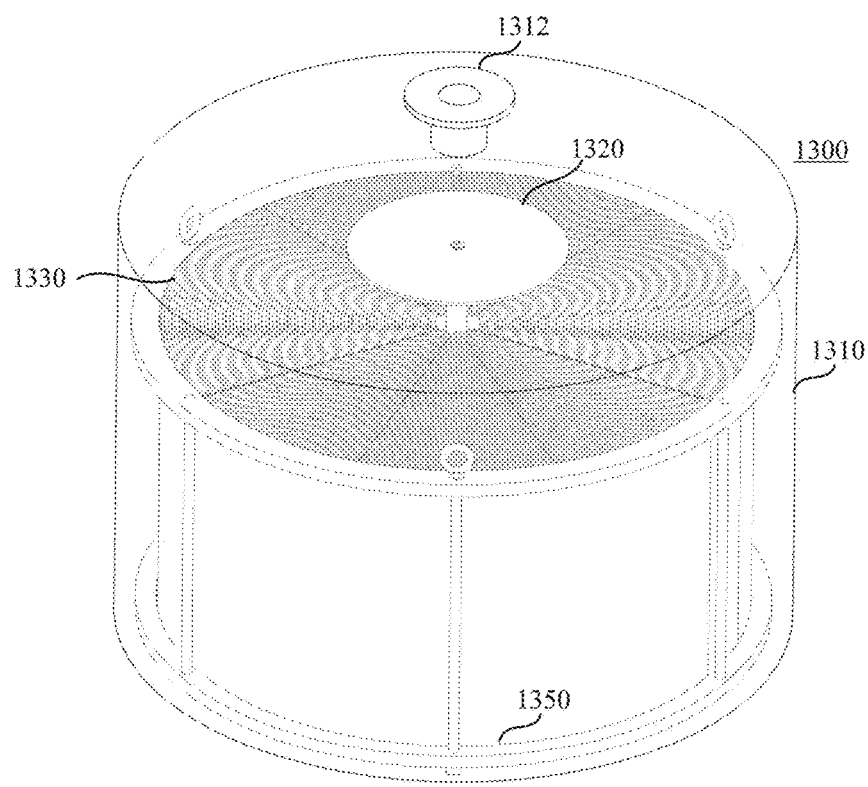
FIG. 13C is an illustrative perspective view of the apparatus shown in FIG. 13A.

FIG. 13A is a cross-sectional side view of the apparatus (1300) comprising a rolled (e.g., spiral shaped) substrate (1330). FIG. 13B is another cross-sectional side view of the apparatus (1300) depicted in FIG. 13A where the substrate (1330) may be rolled so as to comprise a plurality of turns as described in more detail with respect to FIGS. 16A-16F. FIG. 13C is a perspective view of the apparatus (1300). In some embodiments, the apparatus may comprise a plurality of fluid diffusers (1320) disposed in a headspace of the enclosure (1310). For example, the fluid diffuser (1310) may be positioned a predetermined distance from the substrate (1330). In some embodiments, the fluid diffuser (1320) may intersect a central longitudinal axis of the enclosure (1310). The fluid diffuser (1320) may be configured to distribute received fluid flow across one or more of the substrates (1330).

In some embodiments, one or more of the substrates (1330) may be configured to fill a predetermined volume of the enclosure (1310). For example, one or more of the substrates (1330) may extend radially from a central longitudinal axis of the enclosure (1310) to the holder (1350) (e.g., inner circumference) in order to increase a volume of tissue grown within the enclosure (1310). In some embodiments, a substrate (1330) may comprise one or more spacing features (e.g., spacer, protrusion) configured to maintain a predetermined distance between substrate surfaces (e.g., different turns of a substrate, different parallel plates). For example, as described in more detail with respect to FIGS. 16F and 16G, a substrate may comprise a set of spaced-apart protrusions configured to contact another portion of the substrate and which otherwise maintain a predetermined distance between substrate surfaces.

Figure 13D:
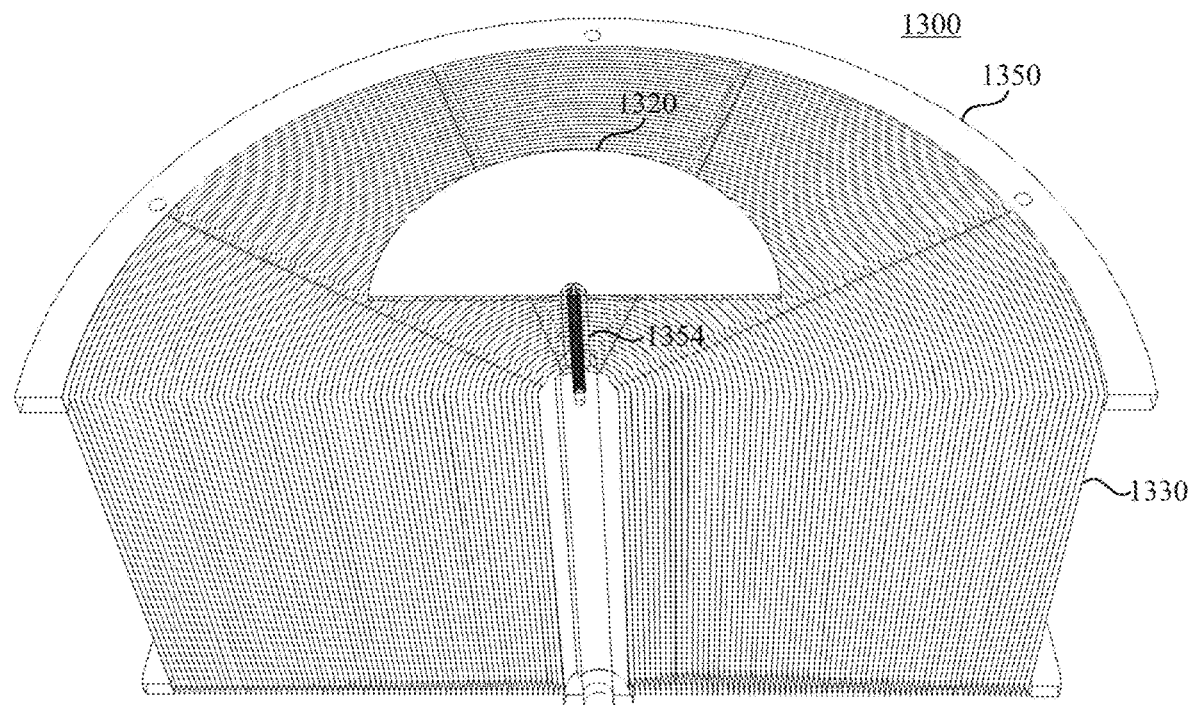
FIG. 13D is an illustrative cross-sectional perspective view of the apparatus shown in FIG. 13A.
Figure 13E:
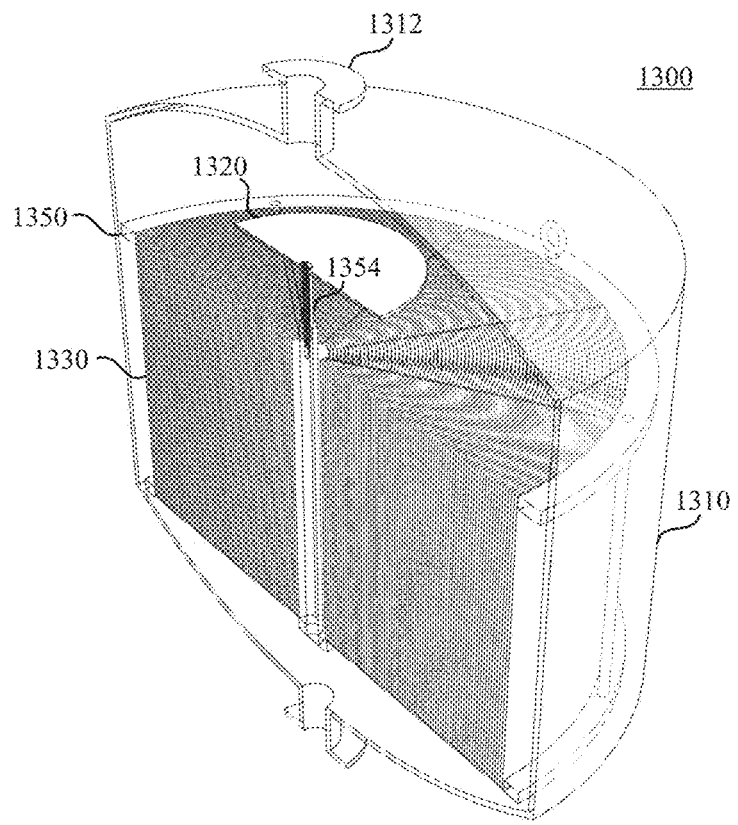
FIG. 13E is another illustrative cross-sectional perspective view of the apparatus shown in FIG. 13A.

FIGS. 13D and FIG. 13E are cross-sectional perspective views of the apparatus (1300). In some embodiments, fluid may be configured to flow downward from the fluid diffuser and into the spaces between the turns of the substrate (1330). For example, a rolled substrate (1330) may define a plurality of parallel fluid channels. In some embodiments, the fluid diffuser (1320) may be coupled to a proximal end of one or more of the substrates (1330). In some embodiments, the fluid diffuser (1320) may be configured to releasably engage to a spacer (1354) of the holder (1350) so as to be at least partially disposed in the cavity (1316). For example, the fluid diffuser (1320) may be slidably and releasably engaged to the holder (1350), thereby aiding maintenance and sterilization of the apparatus (1300). In some embodiments, a collector (not shown) may be coupled to a distal end of the plurality of substrates (1330). In some embodiments, one or more substrates (1330) may be configured to releasably engage to the enclosure (1330). For example, one or more substrates (1330) may be slidably and releasably engaged to the holder (1350), thereby aiding maintenance and sterilization of the one or more substrates (1330). In some embodiments, a longitudinal axis of the substrate (1330) may be parallel to a longitudinal axis of the enclosure (1310).

Figure 13F:
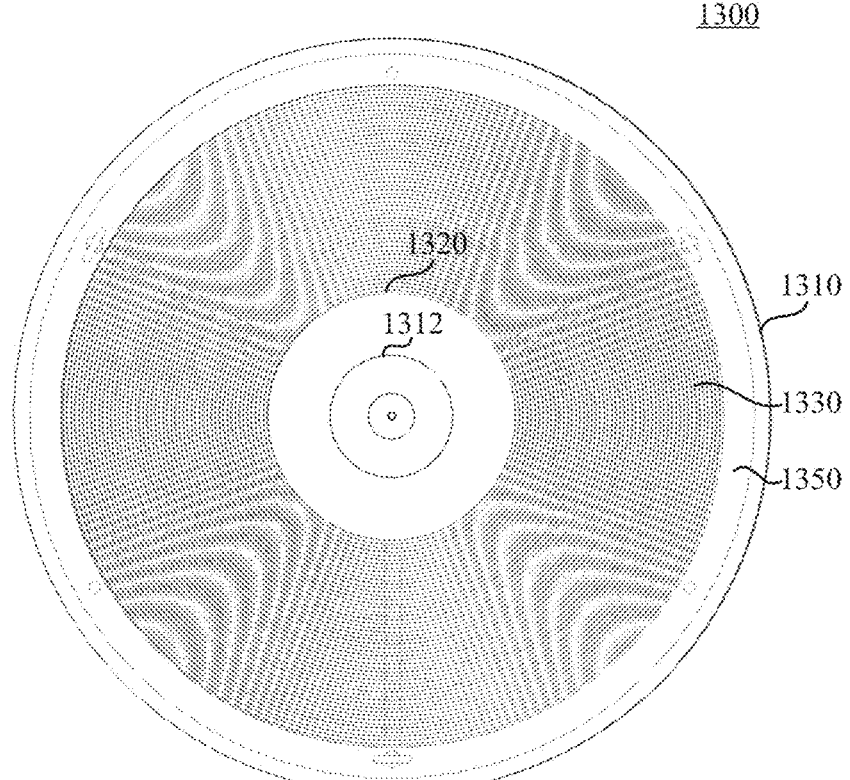
FIG. 13F is an illustrative plan view of the apparatus shown in FIG. 13A.

FIG. 13F is a plan view of the apparatus (1300). In some embodiments, the fluid diffuser (1320) may comprise a diameter less than a diameter of one or more of the substrate (1330) and holder (1350). In some embodiments, the fluid diffuser (1320) may be configured to regulate a fluid flow rate over one or more substrates (1330) of the apparatus (1310). For example, a fluid diffuser (1320) may be configured to receive a fluid and output a substantially uniform and laminar flow to each substrate of the plurality of substrates. In some embodiments, the fluid diffuser (1320) may be coupled to the enclosure and/or one or more of the substrates. The fluid diffuser (1320) may be configured to distribute fluid to the substrate in a predetermined flow pattern. For example, the fluid diffuser may be configured to enable a substantially uniform or laminar flow across a diameter of the substrate. As described in more detail herein, a fluid diffuser may comprise a tapered surface. In some embodiments, a ratio of a dimension (e.g., diameter) of the fluid diffuser to a dimension of the substrate is between about 3:4 and about 1:1, and between about 1,000:1 and about 1:1, including all values and sub-ranges in-between. Additionally or alternatively, the fluid diffuser may comprise one or more openings. For example, a plurality of openings may be substantially equally spaced apart.

In some embodiments, the fluid diffuser may be radially symmetric. In some embodiments, the cavity comprises a headspace, and the fluid diffuser is disposed within the headspace of the enclosure. In some embodiments, a longitudinal axis of the fluid diffuser may be substantially perpendicular to the substrate. In some embodiments, the fluid diffuser and the substrate comprise a predetermined spacing. In some embodiments, the predetermined spacing is up to about 20 cm.

In some embodiments, the fluid diffuser may be radially symmetric. In some embodiments, the cavity comprises a headspace, and the fluid diffuser is disposed within the headspace of the enclosure. In some embodiments, a longitudinal axis of the fluid diffuser may be substantially perpendicular to the substrate. In some embodiments, the fluid diffuser and the substrate comprise a predetermined spacing. In some embodiments, the predetermined spacing may be up to about 20 cm. In some embodiments, the fluid diffuser may comprise polytetrafluoroethylene (PTFE).

FIG. 14A is a plan view of a flat fluid diffuser (1400) comprising a flat disc shape. The fluid diffuser (1400) may comprise a diameter less than a circumference of an inner diameter of the enclosure. FIG. 14B is a perspective view of the fluid diffuser (1400) shown in FIG. 14A. In some embodiments, the fluid diffuser may comprise a one or more openings (see FIGS. 15D and 18B) configured to allow the passage of liquid (e.g., growth media) through the fluid diffuser (1400). That is, the openings may extend through a thickness of the fluid diffuser. The openings may be configured to distribute fluid flow more evenly to one or more substrates disposed beneath the fluid diffuser. For example, each opening may comprise a diameter of about 30 µm, thus allowing the passage of growth media through the fluid diffuser. In some embodiments, the fluid diffuser (1400) may be perpendicular to one or more of the substrates.

FIGS. 14C and 14D are respective side and perspective views of fluid diffuser (1400) and holder (1410). In some embodiments, the holder (1410) may lie along a central longitudinal axis of an enclosure (not shown for the sake of clarity). The configuration of the fluid diffuser (1400) may reduce material build-up, fouling due to clogging, and aid sterilization while configured to output a substantially uniform and laminar flow to a plurality of substrates. For example, fluid may be configured to flow over the top and bottom surfaces of the fluid diffuser (1400). The shape of the fluid diffuser (1400) is circular in FIGS. 14A-14D, but may be any shape. In some variations, a fluid diffuser and substrate may be spaced apart by up to about 20 cm.

Figure 15A:
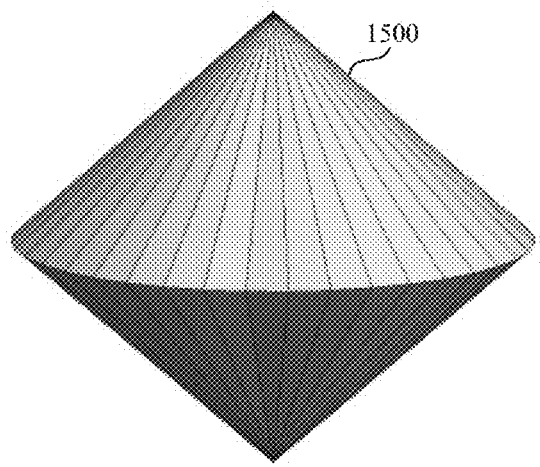
FIGS. 15A, 15B, 15C, and 15D are illustrative perspective views of exemplary embodiments of a fluid diffuser.
Figure 15B:
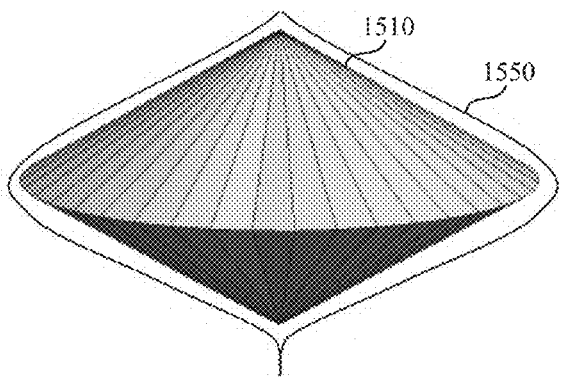
Figure 15C:
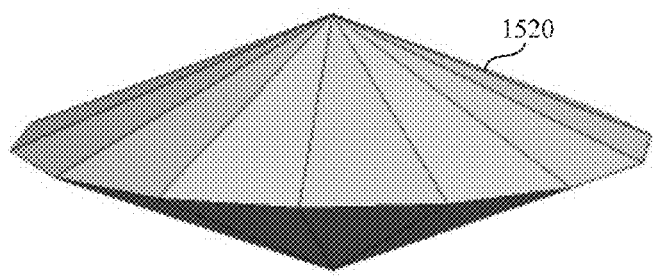

FIGS. 15A-15C are perspective views of variations of an angled fluid diffuser (1500, 1510, 1520) comprising a bicone shape. A bicone (e.g., dicone) may refer to a three-dimensional surface of revolution of a rhombus around one of its axes of symmetry. That is, a bicone may define a structure generated by joining two congruent right circular cones base-to-base. In some embodiments, a bicone may comprise circular symmetry and orthogonal bilateral symmetry. The fluid diffusers (1500, 1510, 1520) depicted in FIGS. 15A-15C illustrate different heights and diameters. The fluid diffuser (1500, 1510, 1520) may comprise a diameter less than a circumference of an inner diameter of the enclosure. In some variations, the bicone may comprise a single portion or a plurality of portions.

In some embodiments, the fluid diffuser (1500, 1510, 1520) may comprise a cone angle of between about 90 degrees and about 170 degrees. Each cone of the bicone may comprise the same or different cone angles. That is, each cone of the bicone may have the same or different heights.

A larger cone allows the fluid diffuser (400) to have a smaller height, and thus may reduce a volume of empty space between an inlet and a plurality of substrates.

In some embodiments, the configuration of openings in the fluid diffuser may comprise a symmetric pattern. For example, the each opening may comprise a substantially same diameter and the spacing between adjacent openings may be substantially the same. In some embodiments, the openings may extend across substantially an entire side of the fluid diffuser.

FIG. 15B illustrates one variation of fluid flow (1550) over the fluid diffuser (1510). Fluid may be configured to flow over substantially an entire surface area of the fluid diffuser (1510). That is, fluid may be configured to flow over the topside and underside of a bicone shaped fluid diffuser. As fluid flows over a perimeter (e.g., circumferential) edge of a fluid diffuser, fluid will flow along the underside of the fluid diffuser through adhesion. Adhesion is the intermolecular attractive force between molecules of a different kind or phase. An example of adhesion is the phenomenon of water wetting a solid surface. Intermolecular forces between the water and the solid surface cause the wetting. However, as fluid flows over the underside, the fluid may drop from the fluid diffuser due to gravity and fall radially over a diameter of the substrate. For example, fluid may flow over a substrate in a radially symmetric manner. A radially symmetric fluid diffuser enables substantially equal paths for fluid flow, which may enable a substantially uniform distribution of fluid over one or more of the substrates.

In some embodiments, an apparatus for preparing a meat product may comprise an enclosure defining a cavity, a substrate arranged within the cavity and configured to support growth of the meat product, and a fluid diffuser comprising a tapered surface and configured to distribute fluid to the substrate in a predetermined flow pattern.

In some embodiments, the tapered surface may comprise one or more of a concave shape, conical shape, frustum shape, steps, and flared shape. In some embodiments, the tapered surface may be angled up to about 80 degrees relative to the substrate. In some embodiments, the fluid diffuser may comprise a bicone.

In some embodiments, the bicone may comprise a first surface and a second surface opposing the first surface. The first surface may be configured to receive the fluid and the second surface may be configured to receive the fluid from the first surface and distribute the fluid to the substrate. In some embodiments, the fluid diffuser may be configured to enable a substantially uniform or laminar flow across a diameter of the substrate. In some embodiments, the fluid diffuser may comprise one or more openings. In some embodiments, the one or more openings may comprise a plurality of openings substantially equally spaced apart. In some embodiments, the fluid diffuser is radially symmetric. In some embodiments, the cavity may comprise a headspace, and the fluid diffuser may be disposed within the headspace of the enclosure. In some embodiments, a longitudinal axis of the fluid diffuser may be substantially perpendicular to the substrate. In some embodiments, the fluid diffuser and the substrate may comprise a predetermined spacing. In some embodiments, the predetermined spacing may be up to about 20 cm.

Figure 15D:
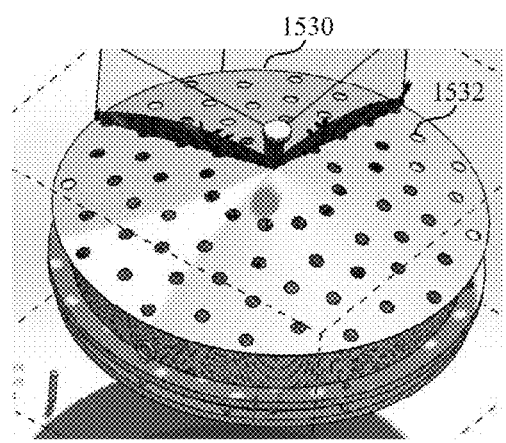

FIG. 15D is a plan view of a fluid diffuser (1530) comprising a conical (e.g., single cone) shape. The fluid diffuser (1530) may comprise one or more openings (1532) configured to allow the passage of liquid (e.g., growth media) through the fluid diffuser (1530). For example, the openings may be substantially equally spaced apart. In some embodiments, each opening (1532) may comprise a predetermined diameter. For example, the diameter of an opening (1532) may be the same or vary as a function of distance from a center of the fluid diffuser (1530). In some embodiments, the fluid diffuser (1500) may be perpendicular to one or more of the substrates. For example, fluid may be configured to flow over the top surface and through the openings (1532) of the fluid diffuser (1500).

The amount of meat product prepared by the apparatuses described herein corresponds to the number and surface area of the substrates of an apparatus. For example, one or more substrates may be configured to generate a commercial-scale quantity of edible meat product.

Figure 16A:
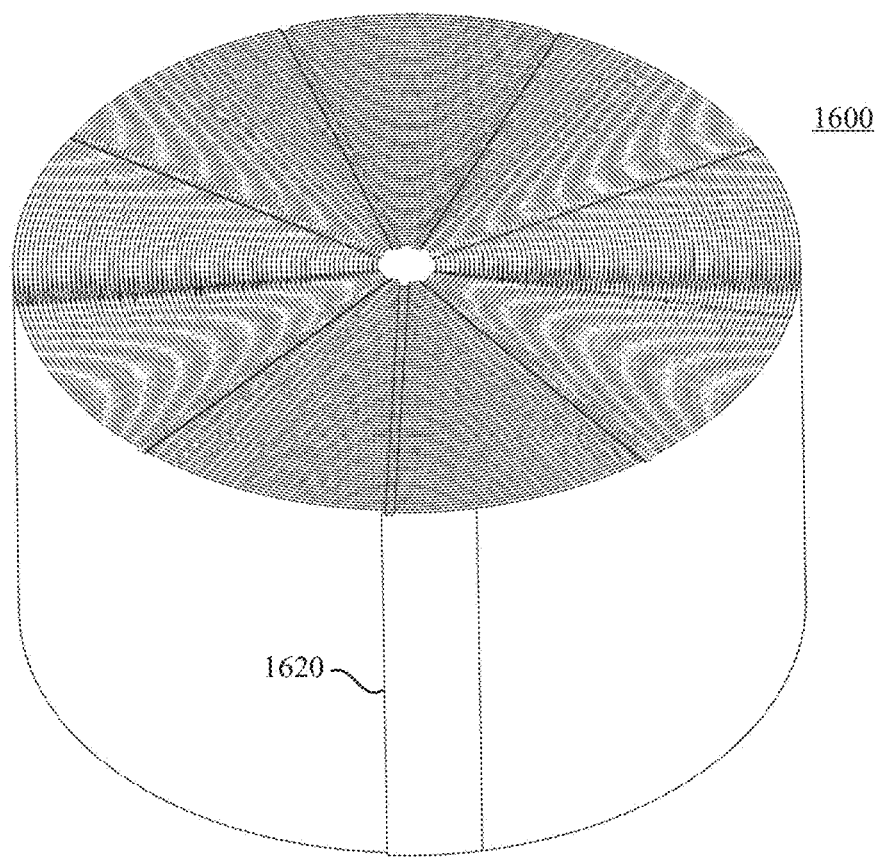
FIG. 16A is an illustrative perspective view of an exemplary embodiment of a substrate.
Figure 16B:
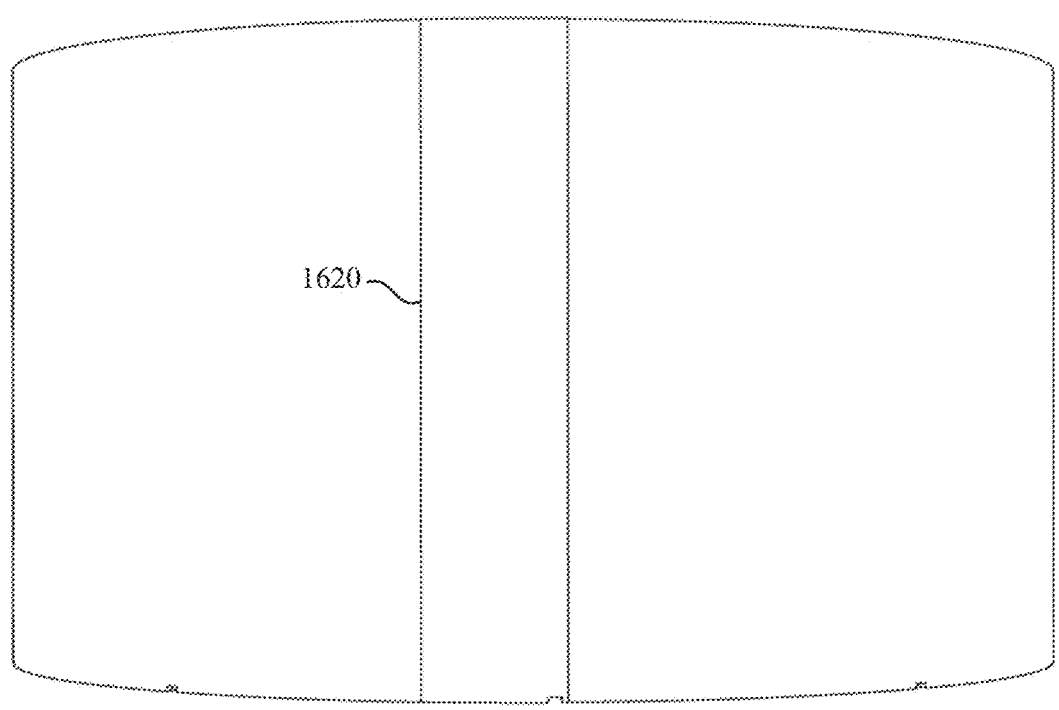
FIG. 16B is an illustrative side view of the substrate shown in FIG. 16A.
Figure 16C:
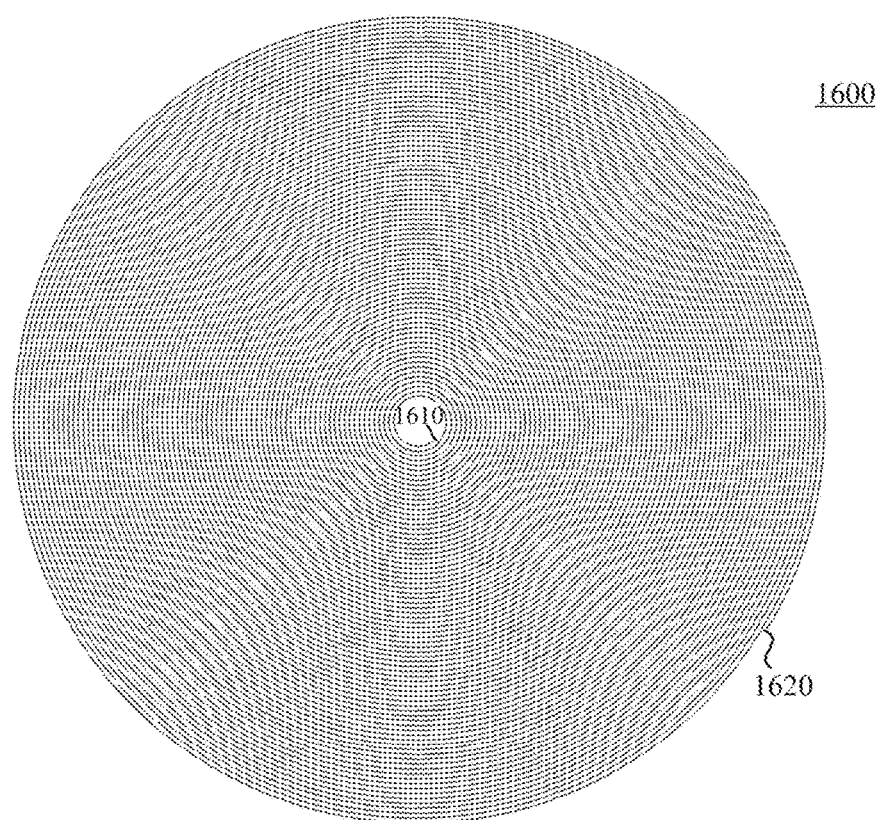
FIG. 16C is an illustrative plan view of the substrate shown in FIG. 16A.
Figure 16D:
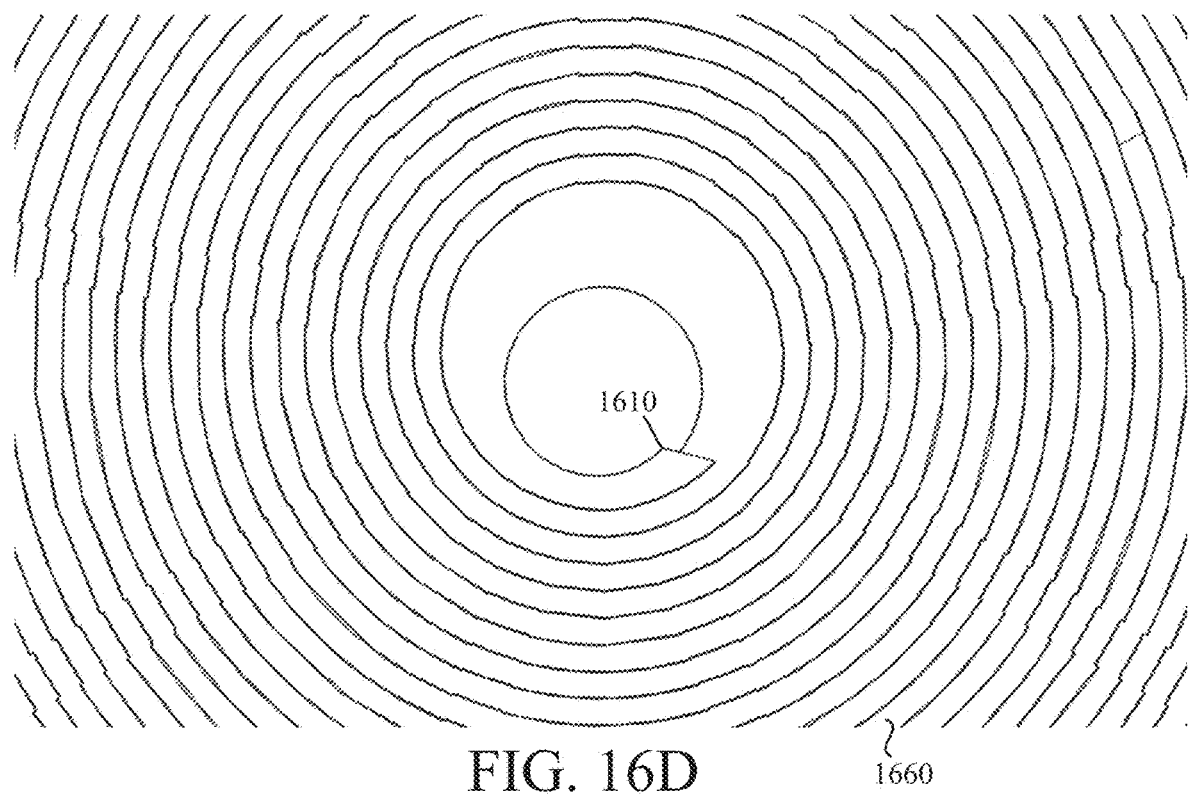
FIG. 16D is an illustrative detailed plan view of the substrate shown in FIG. 16C.
Figure 16E:
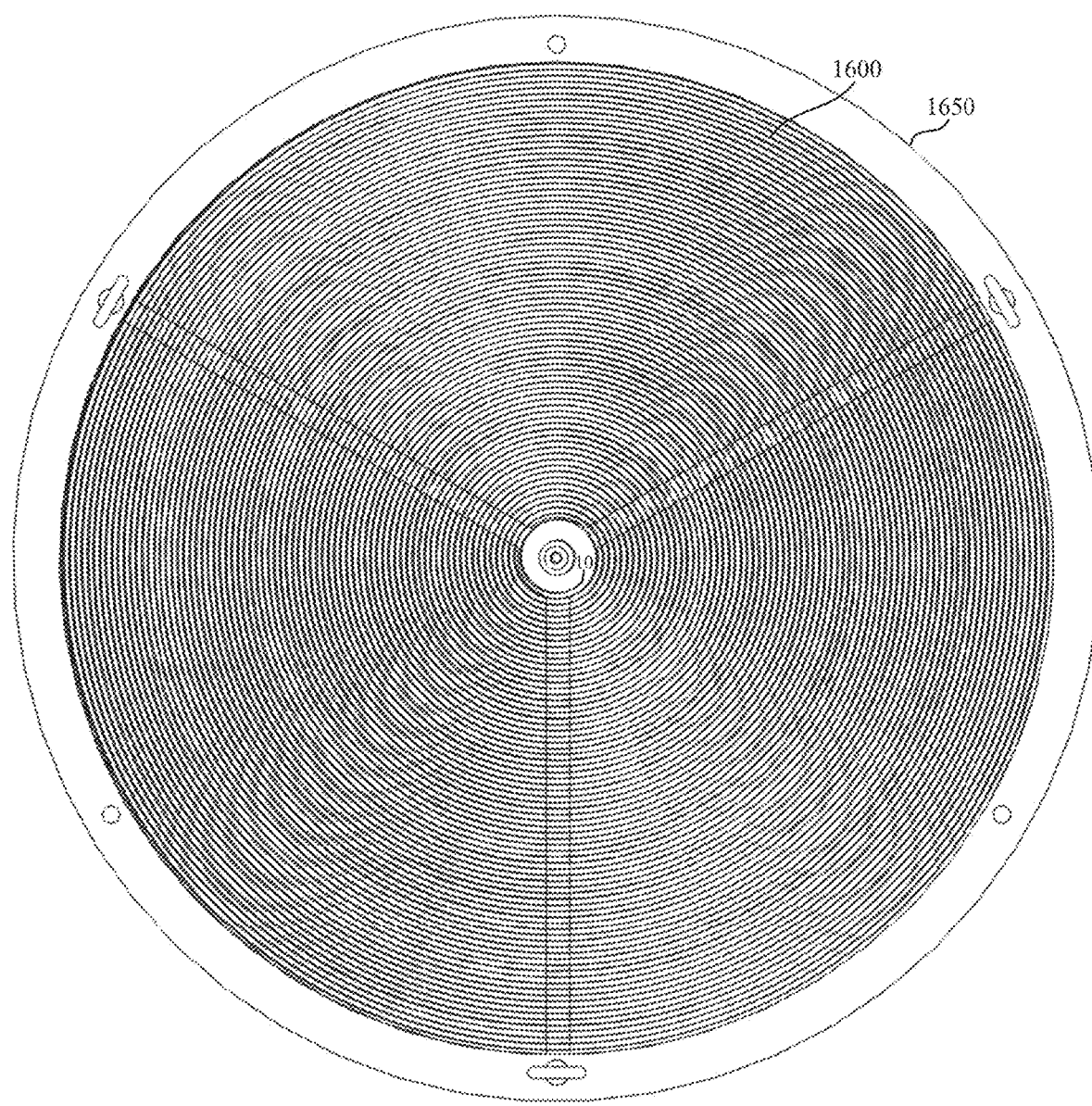
FIG. 16E is an illustrative plan view of the substrate shown in FIG. 16A disposed in an enclosure.
Figure 16F:
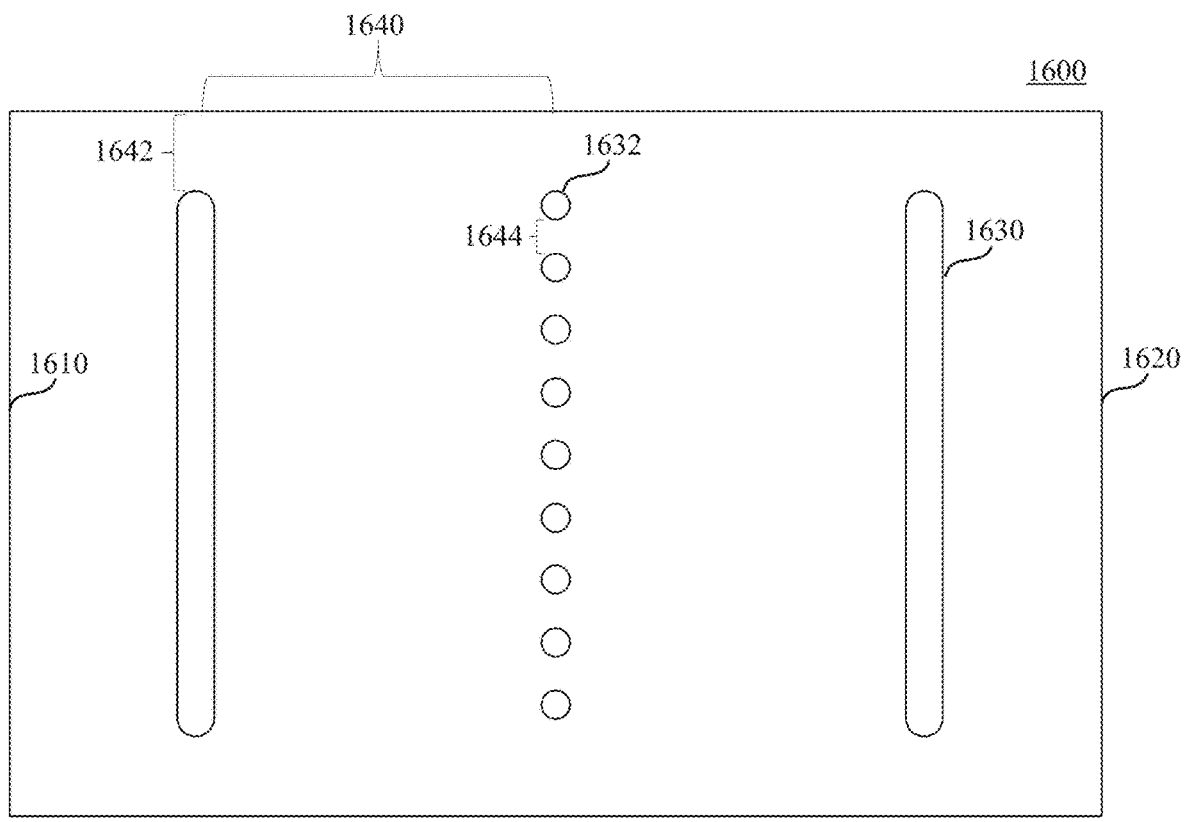
FIG. 16F is an illustrative schematic diagram of an exemplary embodiment of a substrate.

FIG. 16A is a perspective view of a substrate (1600). FIG. 16B is a side view of the substrate (1600). FIG. 16C is a plan view and FIG. 16D is a detailed plan view of the substrate (1600). FIG. 16E is a plan view of the substrate disposed in an enclosure. FIG. 16F is a schematic diagram of a spacer of a substrate. In some embodiments, an apparatus for preparing a meat product may comprise one or more substrates (1600) configured to promote the culture of one or more cells on a surface thereon to form a meat product. In some embodiments, one or more of the substrates (1600) may be removable from a corresponding apparatus such that they may be cleaned or maintained and re-used. Additionally or alternatively, one or more substrates may be sterilized within the apparatus itself. In some embodiments, one or more of the substrates (1600) may be planar and may be substantially parallel to each other. In some embodiments, the apparatus may comprise a single substrate or a plurality of substrates. In some embodiments, the substrate may be configured to releasably engage to the enclosure. For example, a plurality of substrates may be coupled (e.g., attached) to each other in or more configurations (e.g., end-to-end, spaced apart, overlapping). One or more fasteners may be used to couple adjacent substrates to each other.

In some embodiments, a substrate (1600) may comprise a rolled configuration comprising a plurality (e.g., two, three, four, five, or more) of layers (e.g., turns, rotations) that are rolled (e.g., wrapped around) about a longitudinal axis (e.g., central axis). When in the rolled configuration, the substrate (1600) may have a generally cylindrical shape having a circular or ellipsoidal cross-sectional shape. For example, the rolled substrate (1600) may comprise an elliptic cylinder (e.g., cylinder having an elliptical cross-section).

The substrate (1600) may comprise more than one rotation about a predetermined axis. That is, the substrate (1600) may be curved more than 360 degrees about the predetermined axis. For example, the substrate may comprise a plurality of turns about the predetermined axis. In some embodiments, the substrate (1600) may be curved around a longitudinal axis of the enclosure. For example, the substrate (1600) may be arranged (e.g., disposed) within a cavity of the enclosure and aligned to a central longitudinal axis of the enclosure.

In some embodiments, the substrate (1600) may comprise an inner end (1610) (e.g., innermost portion of rolled substrate, proximal end) and an outer end (1620) (e.g., outermost portion of rolled substrate, distal end). For example, FIG. 16D illustrates an inner end (1610) of the substrate (1600) that may define the beginning or center of the substrate (1600), and FIG. 16A illustrates an outer end (1620) of the substrate (1600) that may define an end or last layer of the substrate (1600). The rolled substrate (1600) may comprise one or more turns or rotations such that the substrate overlaps itself. A rolled substrate (1600) as described herein may allow for increased surface area for support and growth of adherent tissue sheets. Furthermore, a rolled substrate (1600) may comprise a geometry having increased rigidity relative to a flat substrate (e.g., plate). In some embodiments, the substrate (1600) may comprise an outer diameter of at least about 5 cm. In some embodiments, the substrate (1600) may comprise a height of up to about 20 cm, 50 cm, 80 cm, and about 100 cm, including all values and sub-ranges in-between.

In some embodiments, the substrate may be manufactured by stamping one or more protrusions on a thin sheet of metal comprising a spring temper. The substrate may be configured to be rolled and placed within an enclosure where it will naturally expand and self-space to fill a cavity of the enclosure. In some embodiments, the substrate may be removably coupled to an enclosure. That is, the substrate may not be fixed to or attached to the enclosure.

In some embodiments, the rolled substrate(s) may be aligned in the direction of the fluid flow. For example, the substrate(s) and corresponding fluid channels may be oriented (e.g., perpendicular, off-axis) relative to a ground surface. In some embodiments, the apparatus may comprise a plurality of fluid channels (1660). For example, the rolled substrate (1600) may define the plurality of fluid channels (1660) between the adjacent turns (e.g., in the spaces between proximate layers of the substrate (1600)). Each fluid channel (1660) may be associated with at least one turn of the substrate (1600) in that a fluid channel (1660) comprises the space between sequential turns. For example, adjacent turns of the substrate (1600) may comprise a predetermined spacing. Fluid may be configured to flow in one direction (e.g., higher elevation to lower elevation) through the plurality of fluid channels (1660). For example, each layer of the substrate (1600) may be separated by a predetermined spacing (e.g., gap) through which fluid may be perfused such that the meat product may be grown on the substrate (1600). In some embodiments, the plurality of fluid channels (1660) are substantially curved (e.g., concentric) and parallel to each other. In some embodiments, each fluid channel (1660) may have a width between about 0.3 mm and about 5.0 cm, including all values and sub-ranges in-between.

In some embodiments, an apparatus for preparing a meat product may comprise an enclosure as described herein and a substrate (1600) arranged within a cavity of the enclosure where the substrate (1600) comprises a spiral and a surface configured to support growth of the meat product. For example, a substrate (1600) may allow for high-density growth of meat products. In some embodiments, the substrate (1600) may be configured to grow the meat product on one or opposite sides of the substrate. In some embodiments, a substrate (1600) may comprise dimensions including a width between about 10 cm and about 300 cm, and a length between about 10 cm and about 200 m, including all values and sub-ranges in-between. In some embodiments, a plurality of substrates (1600) may include up to about 10,000,000 substrates, including all values and sub-ranges in-between. In some embodiments, the substrate may comprise one or more of stainless steel, a ceramic, and a polymer.

In some embodiments, an enclosure may comprise a plurality of rolled (e.g., spiral) substrates (1600) each rolled about a respective axis. For example, a primary rolled substrate having a first diameter may be disposed in the center of an enclosure and a set of secondary rolled substrates having a second diameter smaller than the first diameter may be disposed around a circumference of the primary rolled substrate. As another example, a set of rolled substrates may be arranged in parallel lines within a cavity of an enclosure. That is, an axis of each of the rolled substrates may be non-intersecting and in parallel.

In some embodiments, the substrate (1600) may comprise a thickness of at least about 1 μm. The rigidity of a rolled substrate (1600) due to its spiral shape may allow a corresponding reduction in thickness of the substrate (1600), thereby enabling additional turns of the substrate within a predetermined volume. In some embodiments, each turn of a substrate may be separated by a predetermined distance configured to promote growth of a comestible meat product and allow fluid flow though the substrate (1600). For example, a predetermined distance between adjacent turns of a substrate may be at least about 0.8 mm.

In some embodiments, a single spiral may comprise a plurality of substrates. For example, a substrate may comprise a first substrate portion and a second substrate portion formed separately from the first substrate portion. An end of the first substrate portion may be proximate to an end of the second substrate portion. In some embodiments, the end of the first substrate portion may be coupled to the end of the second substrate portion. For example, the end of first substrate portion is overlapped with the end of the second substrate portion. Alternatively, a fastener may be configured to couple the ends of each substrate portion without the portions contacting each other.

In some embodiments, the substrate may comprise one or more features (e.g., spacers, protrusions) configured to maintain a predetermined spacing between adjacent layers of a substrate. In some embodiments, a substrate may comprise a plurality of protrusions configured to self-space the rolled substrate arranged within an enclosure. In some embodiments, one or more of the protrusions may comprise a generally linear shape. One or more of the protrusions may be stamped into the surface of the substrate. The protrusions may be configured to enable tissue sheets to grow between the spaced-apart protrusions. For example, protrusions having a linear shape may promote growth of tissue sheets having corresponding linear edges. In some embodiments, linear protrusions may aid separation of the tissue sheet from the substrate with reduced tearing and/or damage to the tissue. In some embodiments, one or more protrusions may have a height of at least about 0.8 mm. Adjacent protrusions may comprise a predetermined spacing along the surface of the substrate between about 2 cm and about 8 cm, including all values and sub-ranges in-between.

Figure 16G:
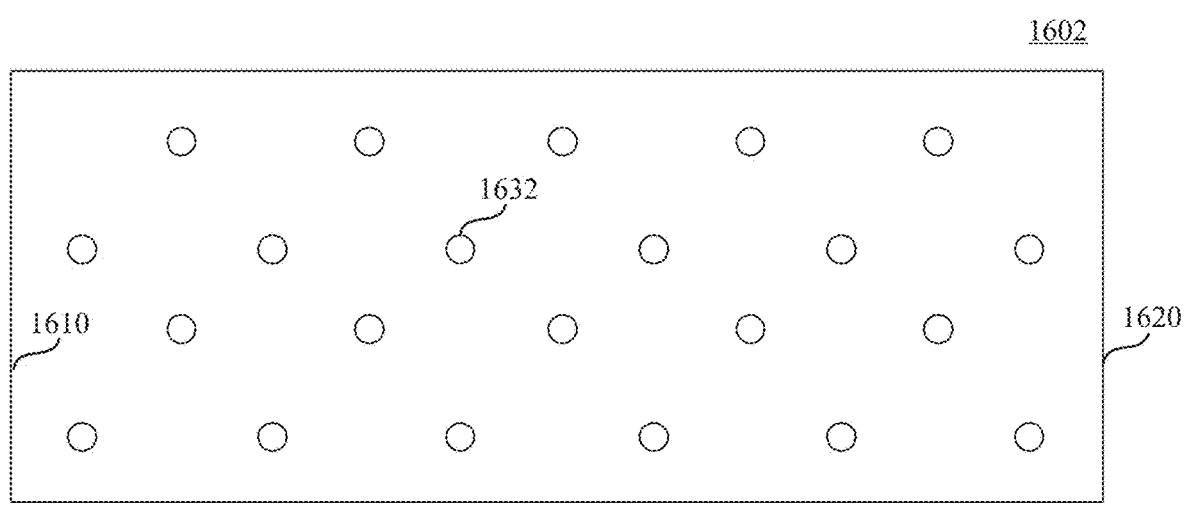
FIG. 16G is an illustrative schematic diagram of another exemplary embodiment of a substrate.

FIGS. 16F and 16G are plan views of a surface of substrate (1600, 1602) comprising a set of spacers (1630, 1632). In some embodiments, the substrates (1600, 1602) may comprise an inner end (1610) and an outer end (1620). The spacers (1630) may be one or more of elongate and rounded in shape. Additionally or alternatively, the spacers (1632) may be generally one or more of circular, spherical, cylindrical, semi-spherical, ovoid, elliptical, combinations thereof, and the like.

Figure 2A:
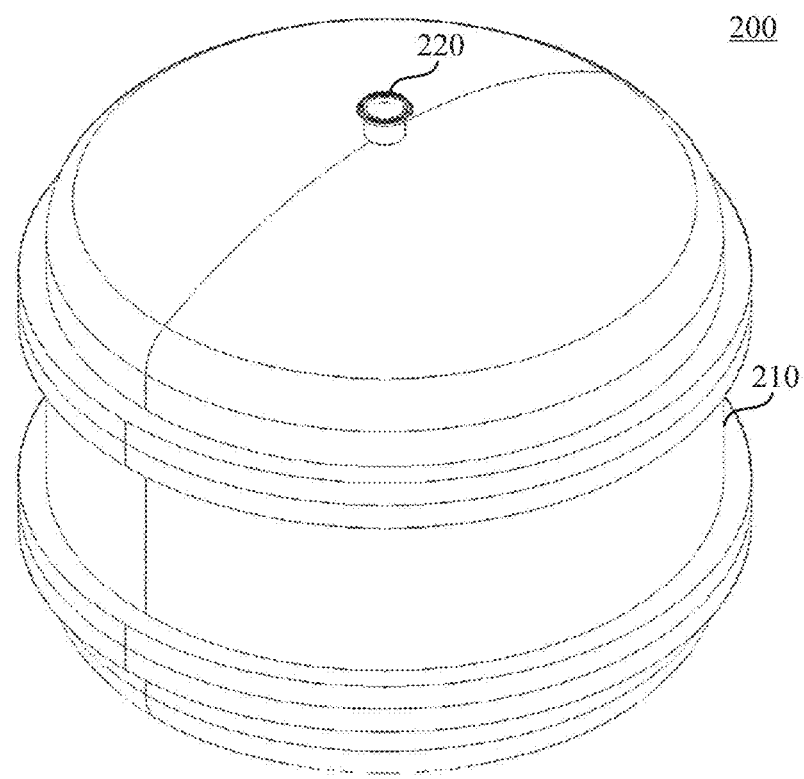
FIG. 2A is an illustrative perspective view of an exemplary embodiment of an apparatus for preparing a meat product.
Figure 2B:
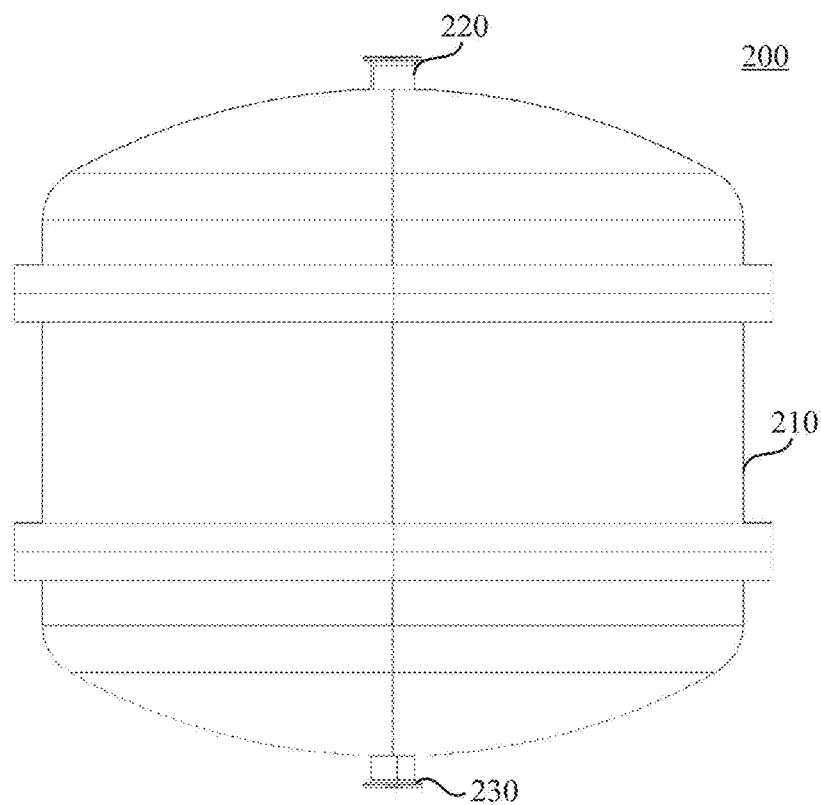
FIG. 2B is an illustrative side view of the apparatus shown in FIG. 2A.
Figure 2C:
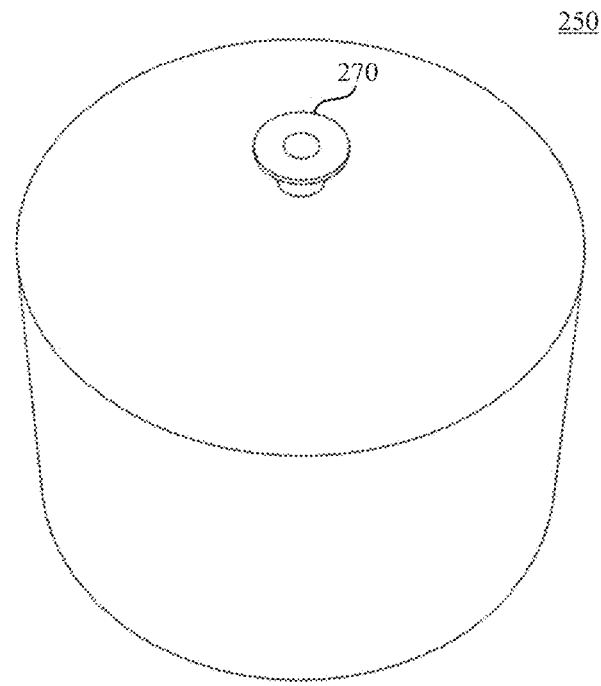
FIG. 2C is another exemplary embodiment of an apparatus for preparing a meat product.
Figure 2D:
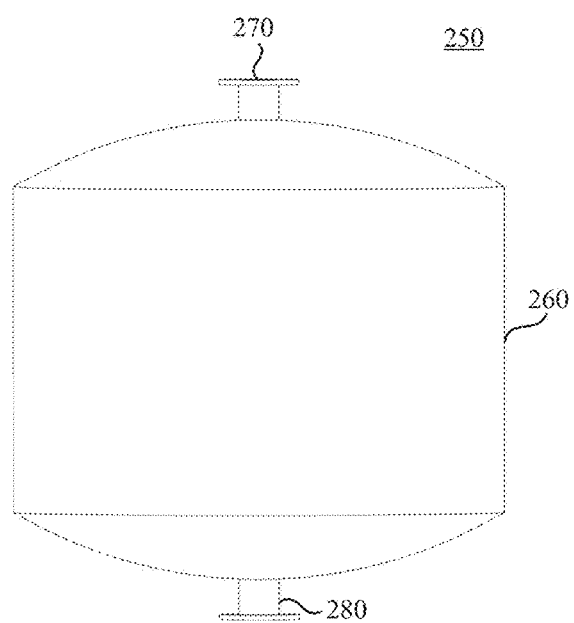
FIG. 2D is an illustrative side view of the apparatus shown in FIG. 2C.
Figure 2E:
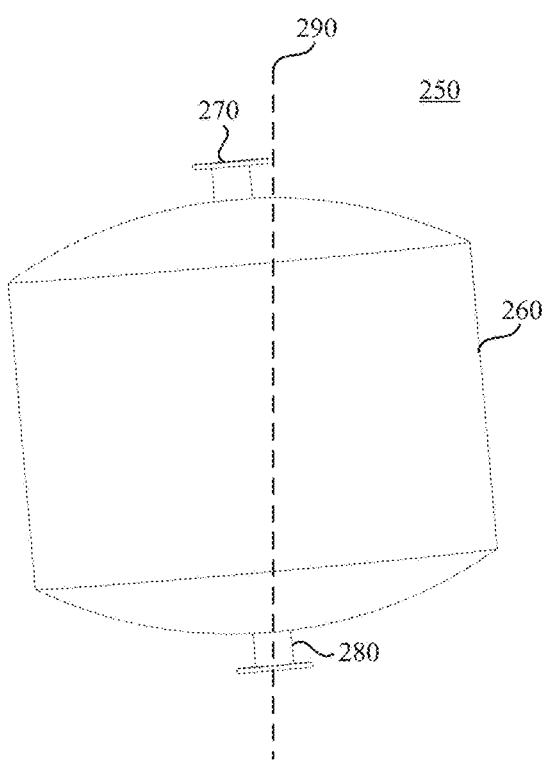
FIG. 2E is another illustrative side view of the apparatus shown in FIG. 2C.

In some embodiments, one or more of the substrate and enclosure may be angled relative to a ground surface in order to promote cell adhesion and tissue growth on the substrate. For example, an enclosure may be configured to be placed on a ground surface and a substrate of the enclosure may define a longitudinal axis having an acute angle relative to the ground surface. FIG. 2E depicts an enclosure (260) at an angle relative to a longitudinal axis (290). Similarly, a substrate (not shown) within the enclosure (260) may be at an acute angle relative to the longitudinal axis (290). In some embodiments, the acute angle may be at least about 85 degrees. Therefore, the surface of the substrate facing away from the ground surface may be configured to support growth of the meat product. In some embodiments, a substrate at a slight angle may both support the adhesion and growth of cells on the substrate and promote laminar fluid flow.

Figure 18A:
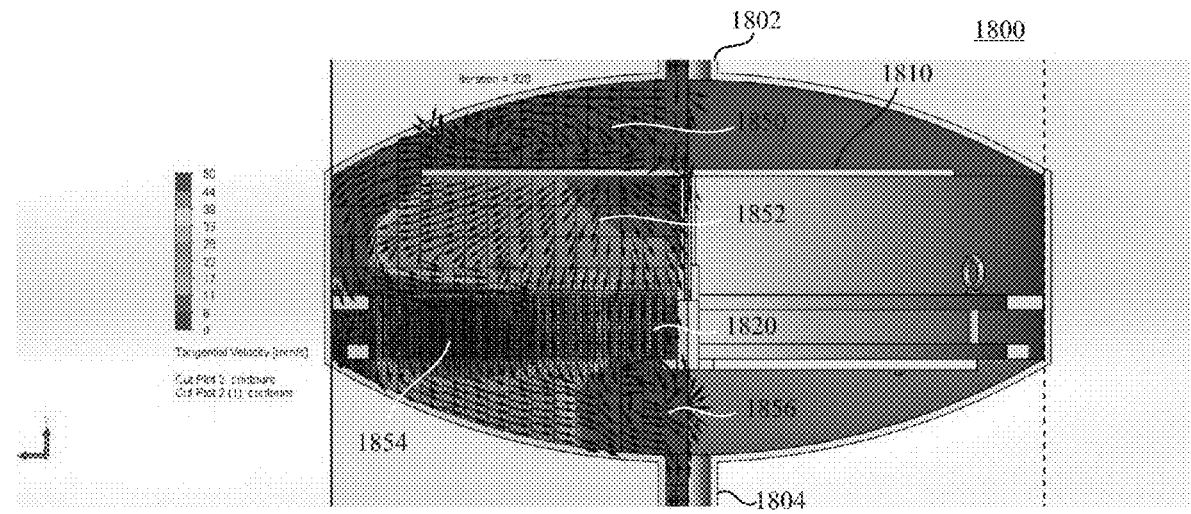
FIGS. 18A, 18B, 18C, 18D, and 18E are illustrative cross-sectional side views of fluid flow through an exemplary embodiment of an apparatus for preparing a meat product.
Figure 18B:
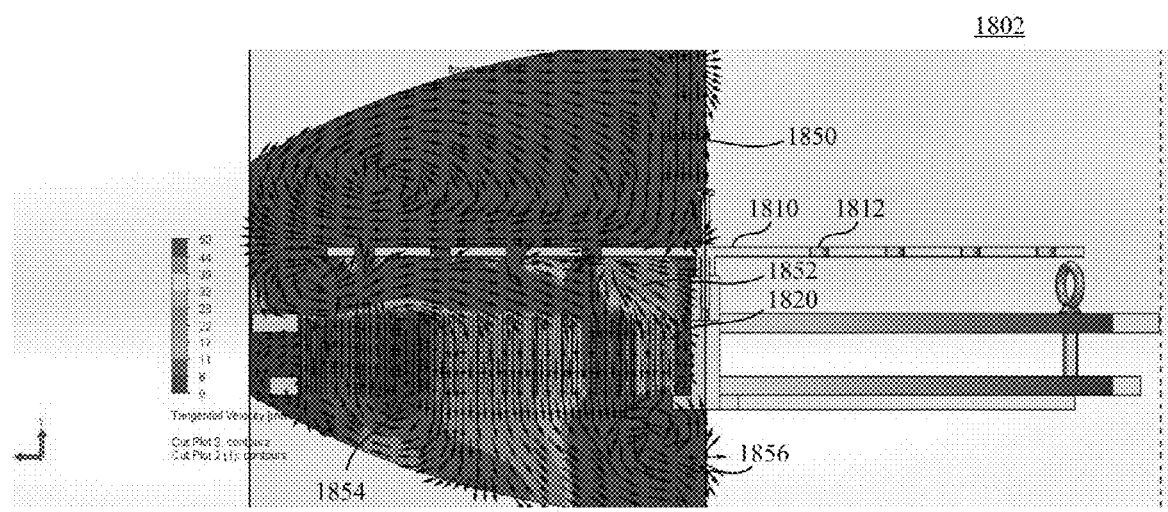
Figure 18C:
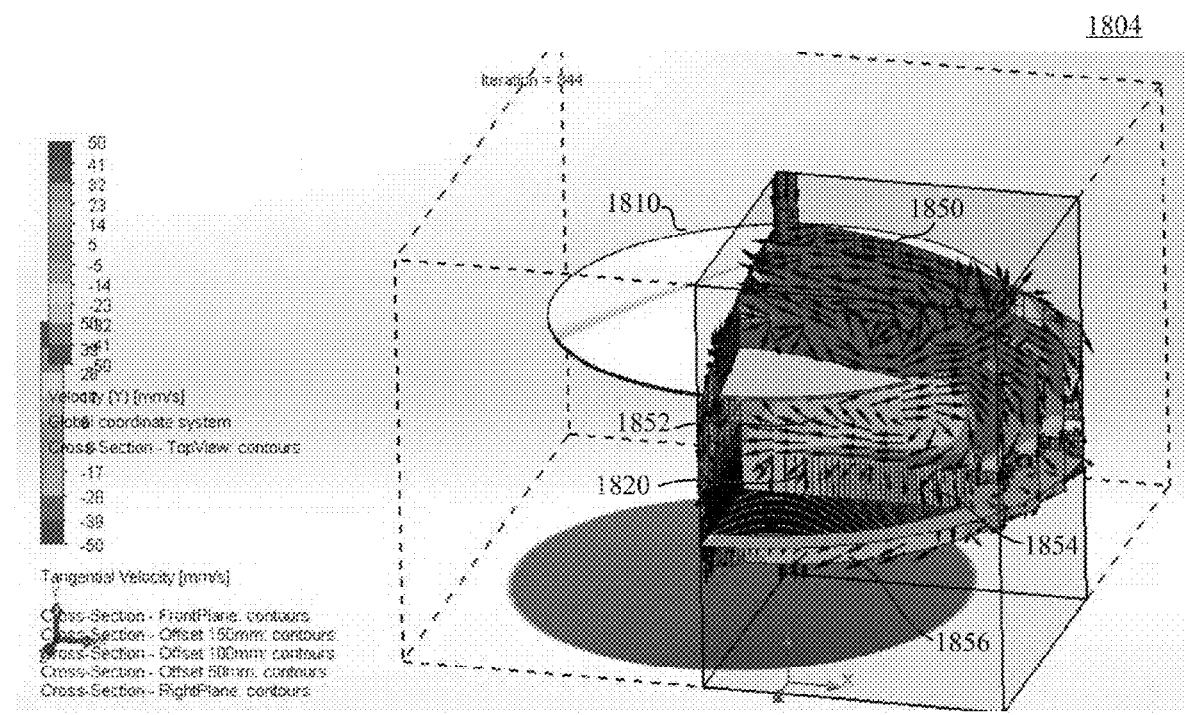

FIGS. 18A-18E are fluid flow vector diagram (1800, 1802, 1804, 1806, 1808) through an apparatus for preparing a meat product as described herein. FIG. 18A illustrates fluid flow velocity (1800) for a cross-sectional image of an apparatus comprising a fluid diffuser (1810) and a rolled substrate (1820). Fluid enters into the apparatus through an inlet (1802) at a relatively high velocity in a non-uniform and non-laminar (1850) manner. The fluid diffuser (1810) receives the fluid and diffuses (e.g., regulates, conditions) the fluid flow (1852) such that the rolled substrates (1820) receive a substantially uniform and laminar fluid flow (1854), thereby allowing consistent cell growth across each layer (e.g., turn) of the substrate (1820). Fluid flow may be generally regular and symmetrically dispersed across the layers of the substrate (1820). For example, FIG. 18C illustrates a perspective view of fluid flow (1804) over a conical fluid diffuser (1810) and through a rolled substrate (1820). Turning back to FIG. 18A, the fluid (1856) passes through the fluid channels between adjacent layers of the substrate (1820) and then through an outlet (1856) of the enclosure (1820). In some embodiments, the system may be configured to maintain a flow rate sufficient to reduce back pressure in the apparatus.

Figure 18D:
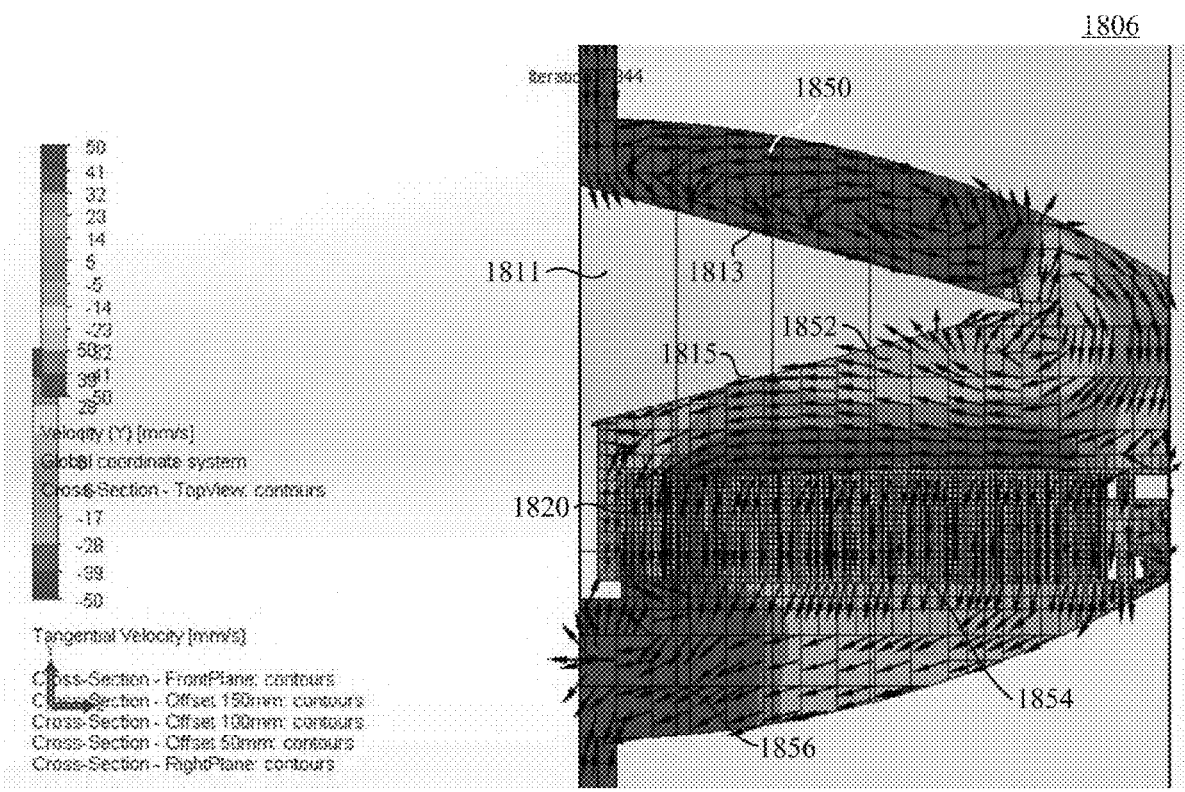
Figure 18E:
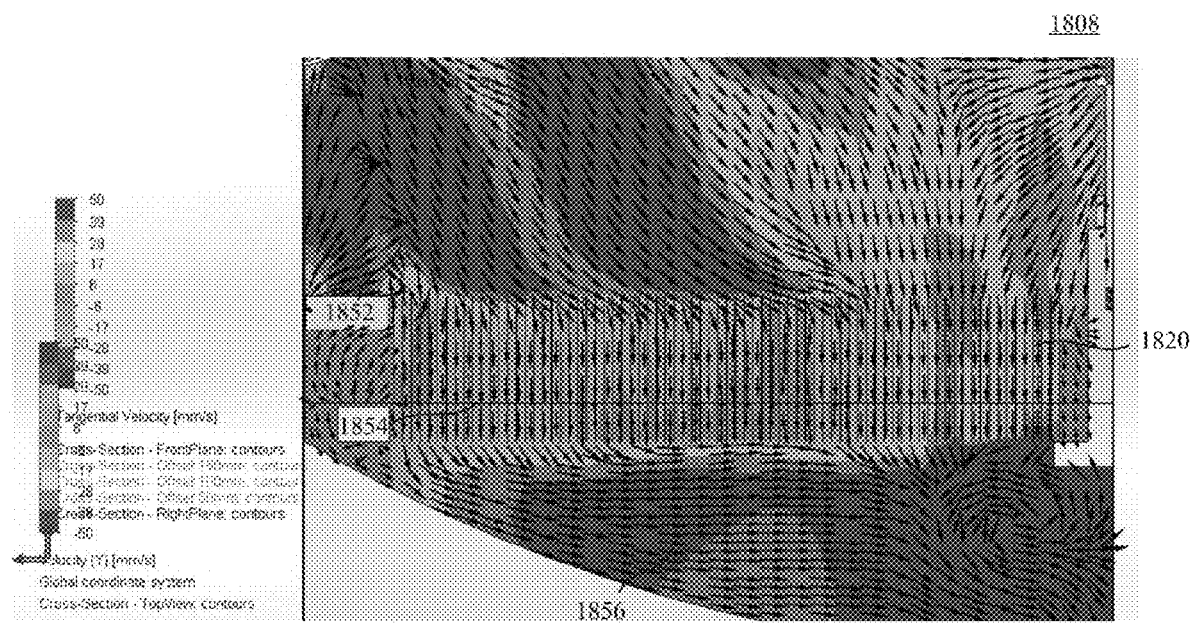

FIG. 18B is a detailed cross-sectional image of fluid flow velocity (1802) for a rolled substrate and a fluid diffuser (1810) comprising a plurality of openings (1812). FIG. 18D is another cross-sectional image of fluid flow velocity (1806) for a bicone fluid diffuser (1811). The fluid diffuser (1811) is configured to allow fluid flow (1850) over a first tapered portion (e.g., upper cone) (1813) and fluid flow (1852) over a second tapered portion (e.g., lower cone) (1815). For example, fluid (1852) may flow sequentially flow over the first tapered portion (1813) followed by the second tapered portion (1815) through adhesion. As fluid flows over the underside (e.g., second tapered portion (1815)) of the bicone diffuser (1811), fluid may drop onto to the substrate (1820) due to gravity. In some embodiments, fluid may flow over the substrate (1820) in a radially symmetric manner. FIG. 18E is a detailed cross-sectional image of fluid flow velocity (1808) through the substrate (1820).

III. METHODS

Also provided herein are methods for preparing a meat product described herein. The methods described here allow for generation and separation of a meat product within an apparatus. In some embodiments, a population of cells are disposed over a substrate to grow the cells into a meat product (e.g., cell sheet). The meat product may be detached from the substrate after the cells reach predetermined growth requirements such as size, maturity, and the like. For example, the meat product may be separated from a substrate in a substantially intact and/or contemporaneous manner using fluid flow. The apparatuses described herein to generate the meat product may further be sterilized for reuse.

Generally, the methods described here include contacting the substrate with a population of cells for a predetermined amount of time. Growth media may be delivered to the cells to promote one or more of cell growth, cell differentiation or maintenance of an undifferentiated cell state. For example, a population of cells may be grown on a surface of any of the substrates described herein. The cells mechanically interact and grow on the surface of the substrate to form a continuous cell sheet. A plurality of substrates may allow the generation and collection of a plurality of cell sheets. The cells grown on the substrate may be detached as an unbroken (e.g., continuous) meat product (e.g., cell sheet) and/or in predetermined sections. In some embodiments, the cells grown on the substrate are detached in a plurality of randomly sized sections. Although substantially planar substrates are described and illustrated herein, the substrates include non-planar substrates such as a curved substrate. For example, a fluid flow over a substrate may apply a predetermined shear force to separate the meat product from the substrate.

Figure 19:
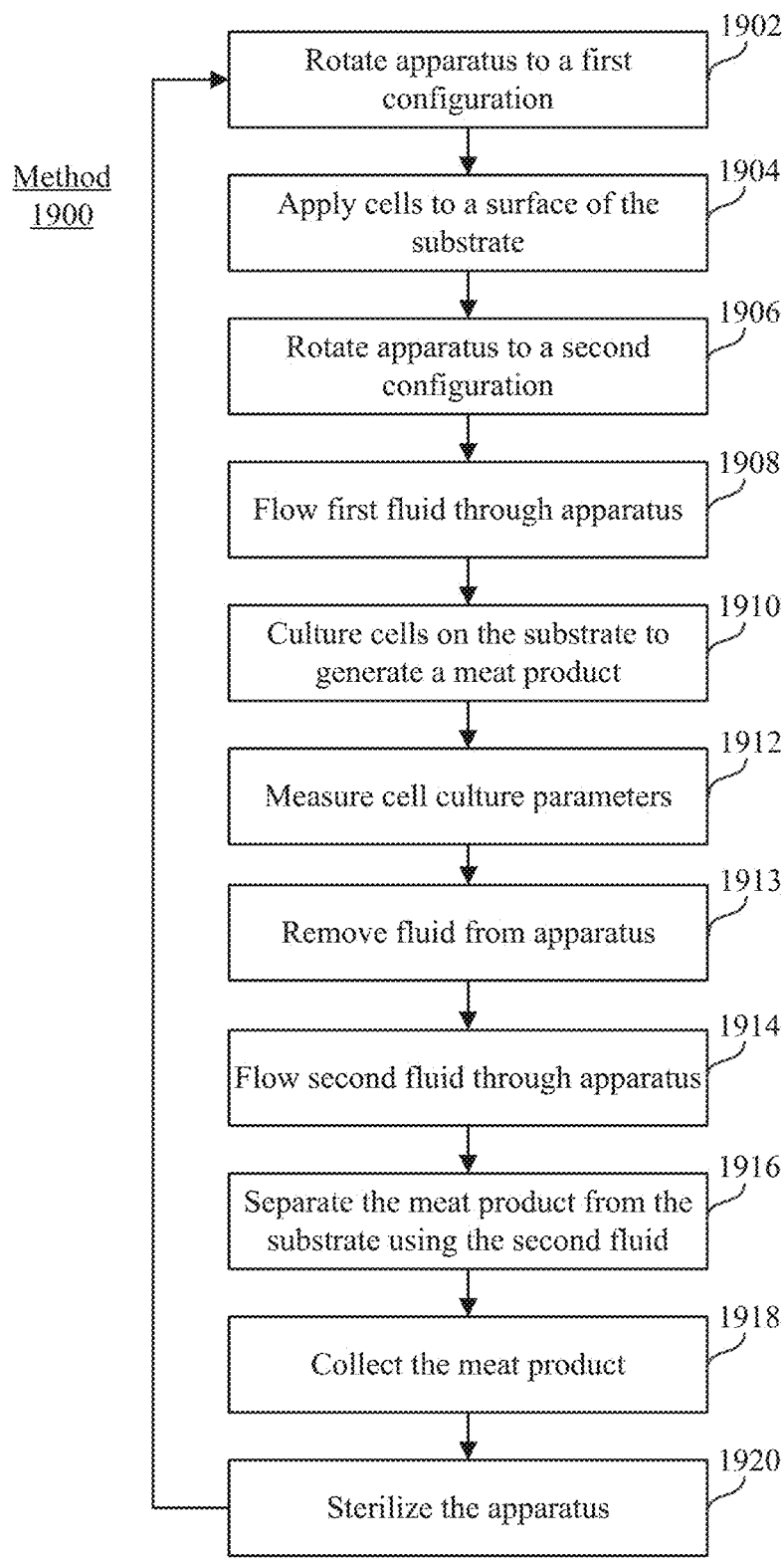
FIG. 19 is an illustrative flowchart of an exemplary method for preparing a meat product using an apparatus of the disclosure.

FIG. 19 is a flowchart that generally describes a method (1900) of preparing a meat product using any of the apparatuses described herein. The process optionally includes rotating an apparatus to a first configuration (1902). In some embodiments, the substrate may be rotated parallel to a ground surface. Cells are applied to a surface of the substrate (1309). In some embodiments, at least about 500 cells/cm$^2$ are applied to the substrates. In some embodiments, between about 5,000 cells/cm$^2$ and about 1,000,000 cells/cm$^2$, including all values and sub-ranges in-between, are applied over the substrates until they attach to a surface of the substrate.

For example, the first configuration, referred to above, may be configured to allow a first side of one or more substrates to be seeded by a plurality of cells such that the cells settle by gravity and adhere and/or attach to the first side of the substrate. For example, cells suspended in fluid media may be flowed over substantially the entire surface area of the substrate. For a flat substrate, the substrate may be positioned (e.g., rotated) to be parallel to a ground surface. In some of these embodiments, the first configuration of the apparatus may further allow a second side (e.g., the opposite side) of one or more substrates to be seeded by a plurality of cells, thereby seeding cells onto substantially an entire surface area of the substrate.

In some embodiments, a substrate may be rolled as shown in FIGS. 16A-16D. The rolled substrate may be disposed within a cavity of an apparatus. For example, the rolled substrate may be placed within the cavity and allowed to self-expand to be held in pace within the apparatus.

In some embodiments, the outer surfaces of the substrate may be wetted to prepare the substrate for cell seeding. For example, a coating of growth media may be applied to the outer surface of the substrate. The apparatus may be optionally filled with growth media and then removed. A set of cells are then placed over each region of a substrate.

After seeding the substrate, the cells are cultured to grow a meat product. The apparatus may be rotated to a second configuration (1906). For example, the second configuration may be configured for fluid flow of the cells over one or more substrates. In some embodiments, the substrate may be aligned substantially perpendicular to a ground surface. For example, a plurality of substrates are arranged in a parallel plate configuration where the substrates are perpendicular to a ground surface, thereby allowing fluid to flow in the spaces between the substrates. The cells are adhered to the substrate such that they overcome the force of gravity and remain on the substrate. In some embodiments, the substrate may be disposed at an acute angle relative to ground.

A first fluid comprising growth media may be flowed through the apparatus (1908). In some embodiments, the system may be configured to continuously culture the cells for a predetermined period of time, such as at least 1 day. In some embodiments, the first fluid in the apparatus may be recirculated at a rate of up to about 3.0 meters per second. In some embodiments, the first fluid flows through the apparatus from a first elevation to a second elevation lower than the first elevation. This configuration may promote complete circulation of fluid through the apparatus. In some embodiments, the first fluid comprises a planar flow over the substrate to provide a non-tortuous flow path that further promotes consistent cell growth across the substrate and complete exchange of the first fluid.

In some embodiments, the fluid may be distributed to the substrate in a predetermined flow pattern. For example, the predetermined flow pattern may comprise a substantially uniform or laminar flow across a diameter of the substrate.

The cells on the substrate are cultured by the first fluid to generate a meat product (1910). Therefore, a comestible meat product may be grown on a substrate. In some embodiments, culturing the cells comprises providing a substantially uniform and laminar first fluid to the substrate, thereby providing consistent and optimized cell growth over all surfaces of the substrate. The first fluid may comprise different compositions for different growth stages of the meat product. In some embodiments, the first fluid may flow in a generally downward direction over the substrate. Additionally or alternatively, the first fluid may flow in a generally upward direction over the substrate.

In some embodiments, the meat product may be held together by an extracellular matrix secreted by the cells and/or cell-to-cell interactions. In some embodiments, the cells comprise one or more of myoblasts, mesangioblasts, myofibroblasts, mesenchymal stem cells, hepatocytes, fibroblasts, pericytes, adipocytes, epithelial, chondrocytes, osteoblasts, osteoclasts, pluripotent cells, somatic stem cells, and endothelial cells. In some embodiments, the cells comprise one or more cells from livestock, poultry, game, and aquatic animal species.

The meat product may have a thickness (e.g., height) of at least about 1 µm. For example, the meat product has a thickness in a range between about 1 µm and about 5 mm, between about 100 µm and about 1 mm, between about 200 µm and about 500 µm, and between about 300 µm and about 800 µm, including all values and sub-ranges in-between.

One or more of the apparatus, cells, and fluid may be measured to monitor the growth of the meat product (1912). For example, one or more sensors may be configured to monitor one or more of the fluid, cell sheet, apparatus, fluid pump, and fluid source. In some embodiments, sensor measurements may be used to modify one or more fluid parameters such as fluid flow rate and fluid composition. Furthermore, sensor measurements may be output to a user to allow the process to be monitored. Sensor measurements may include, but are not limited to, pH, dissolved gas concentration, osmolality, nutrient concentration, waste concentration, ion concentration, oxygen concentration, temperature, and the like. In some embodiments, the apparatus for preparing a meat product may comprise a temperature range between about 4° C. and about 40° C., a pH between about 6.6 and about 7.8, a dissolved oxygen between about 2% and about 120%, including all values and sub-ranges in-between.

Once growth of the meat product has reached predetermined criteria, the meat product may be separated from the substrate for collection. In some embodiments, a second fluid may be flowed through the apparatus (1914). The meat product may be separated from the substrate using the second fluid (1916). When sufficient shear force may be applied to the meat product by the second fluid having a predetermined rate, the meat product will separate from the substrate. In some embodiments, the second fluid may comprise non-laminar, turbulent flow. For example, the second fluid may comprise gas and liquid (e.g., bubbling gas in liquid) configured to generate a turbulent fluid and/or a periodic fluid flow pattern to aid separation of the meat product from the substrate. In some embodiments, the second fluid may comprise a saline solution (e.g., 0.2-0.9% saline solution). In some embodiments, the second fluid may be regulated by a second fluid diffuser (e.g., spray ball) configured to separate the meat product from one or more substrates. In some variations, the comestible meat product may be separated from the substrate by directing a fluid at a predetermined angle with respect to the substrate. The predetermined angle may be between about 10 degrees and about parallel to the substrate. In some embodiments, a separator may be configured to output fluid from one or more fluid nozzles to direct fluid towards the substrate at a predetermined angle. In some embodiments, the separator may be configured to rotate about a predetermined axis when the fluid is directed at the meat product. The fluid may comprise a linear velocity between about 0.003 m/sec and about 3.0 m/sec. The fluid may comprise a flow path comprising an angle of up to about 120 degrees.

In some embodiments, the meat product may be detached as a substantially continuous, and/or whole, multi-layered piece. That is, the substrate and second fluid enables intact and/or contemporaneous release of the meat product from the substrate. The meat product need not be detached as a single piece, and may detach in predetermined portions rather than detach and break apart in an uncontrolled, arbitrary manner. In some embodiments, the meat product may be detached in a plurality of separable sections (e.g., 2 or more pieces).

In some embodiments, separation of the meat product from the substrate may be performed using a plurality of mechanisms. For example, separation of the meat product from the substrate may comprise one or more of fluidic, spontaneous, chemical, electrical, optical, thermal, and mechanical detachment by inducing contraction and/or relaxation of the cells. For example, one or more buffers or enzymatic solutions contact the cells to induce detachment from the substrate. In some embodiments, one or more of a volume and rate of fluid flow through a fluid channel may be increased to detach the meat product. For example, fluid flow may be increased between adjacent substrates in a parallel plate configuration to fluidically separate the meat product from the substrate. In some variations, fluid may be removed from the apparatus prior to separating the comestible meat product from the substrate. As another example, second fluid including air bubbles flows over the surface of a substrate, thereby creating turbulent flow configured to apply a shear force sufficient to detach a cell sheet from the substrate. In some embodiments, the second fluid has a higher viscosity than the first fluid, which may increase the interfacial shear stress applied to the cell sheet, thereby facilitating cell sheet detachment. In some embodiments, the second fluid may have the same composition as the first fluid.

The meat product may be separated from the substrate and then collected within or outside an apparatus. In some embodiments, the separated meat product may be collected (1918). In some embodiments, a substantially whole meat product may be released at a predetermined time (e.g., controlled, reduced, extended), with substantially little cell sheet remaining attached to the substrate or broken off. Additionally or alternatively, the meat product may be detached in a set of separable sections. For example, the substrate may be configured to allow a meat product grown on a substrate to be detached in a plurality of sections (e.g., 2 or more pieces). The meat product may be collected internally or externally of an apparatus for preparing a meat product. In some embodiments, the meat product may comprise a volume between about 0.0001 m$^3$ and about 0.1 m$^3$.

The apparatus may be sterilized (1920) for reuse to at least reduce waste and cost. For example, the apparatus may be steam sterilized before culturing and separating another meat product on the substrate. In some embodiments, the apparatus may be disassembled. For example, at least one of the substrates, fluid diffuser, and collector may be detached from the apparatus. In some embodiments, the substrates, fluid diffuser, and collector comprise flat and thin surfaces configured to drain freely, without joints or internal surfaces (e.g., internal void, spaces) that may otherwise trap debris. The linear fluid channels also aid sterilization.

IV. EXAMPLES

As described herein, the systems, apparatuses, and methods provided herein are useful to control the characteristics of growth, adhesion, release, and/or retention of cultured cells (e.g., cell sheets) to prepare a meat product. Table 1 (below) lists the amounts of meat product produced for different cell species and cell types for different durations using the systems and apparatuses described herein.

TABLE 1

| Experiment # | Species Cultivated | Culture Duration (days) | Meat Produced (grams) |
|---|---|---|---|
| 1 | Duck | 12 | 165 |
| 2 | Duck | 13 | 230 |
| 3 | Chicken | 14 | 299 |
| 4 | Chicken | 17 | 958 |

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Although the foregoing implementations has, for the purposes of clarity and understanding, been described in some detail by of illustration and example, it will be apparent that certain changes and modifications may be practiced, and are intended to fall within the scope of the appended claims. Additionally, it should be understood that the components and characteristics of the substrates described herein may be used in any combination, and the methods described herein may comprise all or a portion of the elements described herein. The description of certain elements or characteristics with respect to a specific figure are not intended to be limiting or nor should they be interpreted to suggest that the element cannot be used in combination with any of the other described elements.

In addition, any combination of two or more such features, structure, systems, articles, materials, kits, steps and/or methods, disclosed herein, if such features, structure, systems, articles, materials, kits, steps and/or methods are not mutually inconsistent, is included within the inventive scope of the present disclosure. Moreover, some embodiments disclosed herein may be distinguishable from the prior art for specifically lacking one or more features, elements, and functionality found in a reference or combination of references (i.e., claims directed to such embodiments may include negative limitations).

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

We claim:

1. A method of growing a cell mass, comprising:
   a) grown the cell mass on a substrate of an apparatus, wherein the substrate: is spiral in shape or perpendicular to a ground surface or planar and oriented to the ground surface at an angle of 85°-90°; and
   b) separating the cell mass from the substrate in a continuous sheet of cells held together by one or more of cell-to-cell interactions and extracellular matrix generated by the cells.

2. The method of claim 1, wherein the substrate is angled at 85° relative to the ground surface.

3. The method of claim 1, wherein the substrate is curved around a longitudinal axis.

4. The method of claim 3, wherein the substrate is angled relative to the longitudinal axis by 5 or more degrees.

5. The method of claim 3, wherein growing the cell mass includes delivering fluid substantially parallel to the longitudinal axis.

6. The method of claim 1, further comprising delivering fluid between adjacent substrates.

7. The method of claim 1, wherein separating the cell mass comprises directing fluid at an angle relative to the substrate.

8. The method of claim 7, further comprising removing the fluid from the apparatus prior to separating the cell mass from the substrate.

9. The method of claim 1, further comprising delivering fluid through a fluid diffuser.

10. The method of claim 9, wherein the fluid diffuser is configured to deliver a substantially uniform or laminar flow across a surface of the substrate.

11. The method of claim 9, wherein the fluid diffuser comprises one or more openings.

12. The method of claim 9, wherein delivering the fluid includes distributing the fluid to the substrate in a predetermined flow pattern using a tapered surface of the fluid diffuser.

13. The method of claim 12, wherein the tapered surface comprises a conical shape.

14. The method of claim 1, wherein the substrate includes one or more channels, one or more grooves, one or more recessions, or a combination thereof.

15. The method of claim 1, wherein the substrate includes a coating to improve cell behavior including adhesion, proliferation, differentiation, and maturation.

16. The method of claim 1, wherein the substrate is textured, coated, porous, circular, nested, comprised of a plurality of turns, or some combination thereof.

17. The method of claim 1, wherein the substrate comprises a three-dimensional lattice.

18. The method of claim 1, wherein the cell mass comprises a comestible, cell-based meat product.

19. The method of claim 1, wherein the cell mass comprises bovine, porcine, ovine, caprine, poultry, aquatic cells, or some combination thereof.

* * * * *